United States Patent [19]

Buckley et al.

[11] Patent Number: 5,468,857
[45] Date of Patent: Nov. 21, 1995

[54] FUNGICIDES

[75] Inventors: Alan J. Buckley, Oldham Lancs; Michael G. Huchings, Prestwich; Ian Ferguson, Todmorden; Kevin Beautement, Berkshire; John M. Clough, Buckinghamshire; Patrick J. Crowley, Berkshire; Christopher R. A. Godfrey, Berkshire; Paul J. deFraine, Berkshire; Vivienne M. Anthony, Berkshire; Stephen P. Heaney, Berkshire, all of England

[73] Assignee: Imperial Chemical Industries PLC, London, England

[21] Appl. No.: 191,163

[22] Filed: Feb. 3, 1994

Related U.S. Application Data

[62] Division of Ser. No. 242,760, Sep. 9, 1988, Pat. No. 5,334,748.

[30] Foreign Application Priority Data

| | | | |
|---|---|---|---|
| Sep. 9, 1987 | [GB] | United Kingdom | 8721221 |
| Sep. 15, 1987 | [GB] | United Kingdom | 8721706 |
| Jan. 22, 1988 | [GB] | United Kingdom | 8801485 |
| Mar. 17, 1988 | [GB] | United Kingdom | 8806317 |
| Jun. 21, 1988 | [GB] | United Kingdom | 8814734 |

[51] Int. Cl.$^6$ .............................................. C07D 239/02
[52] U.S. Cl. ..................... 544/298; 544/49; 544/179; 544/194; 544/216; 544/219; 544/224; 544/283; 544/330; 544/408; 546/146; 546/152; 546/290; 546/297; 548/132; 548/133; 548/146; 548/190; 548/206; 548/356.1; 549/29; 549/475; 549/480; 549/543

[58] Field of Search ..................... 544/298, 408, 544/219, 224, 283, 330, 49, 179, 194, 216; 546/146, 152, 290, 297; 548/132, 133, 146, 190, 206, 356.1; 549/29, 475, 543, 480

[56] References Cited

U.S. PATENT DOCUMENTS 4,709,078  11/1987  Schirmer et al. .................... 560/60

FOREIGN PATENT DOCUMENTS 0178826  4/1986  European Pat. Off. .
0203608  12/1986  European Pat. Off. .

*Primary Examiner*—Paul J. Killos
*Attorney, Agent, or Firm*—Cushman Darby & Cushman

[57] ABSTRACT

Fungicidal compounds of the formula (I):

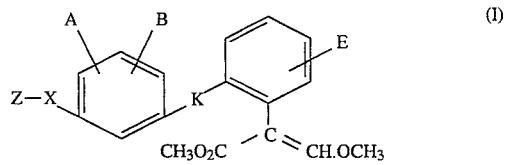

and stereoisomers thereof, wherein K is oxygen or sulphur; Z is optionally substituted aryl or optionally substituted heteroaryl; X is a specified linking group; and A, B and E, which may be the same or different, are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; except that when Z is unsubstituted phenyl and X and K are oxygen, A, B and E are not all hydrogen.

13 Claims, No Drawings

FUNGICIDES

This is a division of application Ser. No. 07/242,760, filed Sep. 9, 1988, now U.S. Pat. No. 5,334,748.

This invention relates to derivatives of propenoic acid useful as fungicides, to processes for preparing them, to fungicidal compositions containing them, and to methods of using them to combat fungi, especially fungal infections of plants.

EP-A-0178826 describes fungicidal derivatives of propenoic acid and lists the compound (E)-methyl 2-[2-(3-phenoxyphenoxy)phenyl]-3-methoxypropenoate.

The present invention provides a compound having the formula (I):

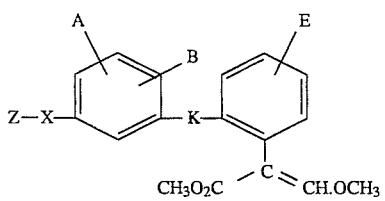

and stereoisomers thereof, wherein K is oxygen or sulphur; Z is optionally substituted aryl or optionally substituted heteroaryl; X is O, $S(O)_n$, $NR^4$, $CR^1R^2$, $CHR^9$, CO, $CR^1(OR^2)$, $C=CR^1R^2$, $CHR^1CHR^2$, $CR^1=CR^2$, $CHR^1CR^2=CH$, $C=C$, $OCHR^1$, $CHR^1O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, CO.CO, $COCHR^1$, $COCHR^1O$, $CHR^1CO$, $CHOH.CHR^1$, $CHR^1.CHOH$,

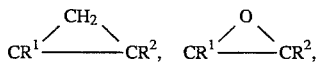

$CONR^4$, $OCONR^4$, $NR^4CO$, $CSNR^4$, $OCS.NR^4$, $SCO.NR^4$, $NR^4CO_2$, $NR^4CS$, $NR^4CSO$, $NR^4COS$, $NR^4CONR^4$, $S(O)_nNR^4$, $NR^4S(O)_n$, $CS_2$, $S_2C$, CO.S, SCO, N=N, $N=CR^1$, $CR^1=N$, $CHR^1CHR^2CH(OH)$, $CHR^1OCO$, $CHR^1SCO$, $CHR^1NR^4CO$, $CHR^1NR^4CONR^4$, $CHR^1CHR^2CO$, $O.N=CR^1$, $CHR^1O.N=CR^2$, $CO.OCR^1R^2$, $CHR^1CHR^2CHR^3$, $OCHR^1CHR^2$, $(CH_2)_mO$, $CHR^1OCHR^2$, $CHR^1CHR^2O$, $OCHR^1CHR^2O$, $S(O)_nCHR^1CHR^2$, $CHR^1S(O)_nCHR^2$, $CHR^1CHR^2S(O)_n$, $CR^1=NNR^4$, $NR^4N=CR^1$, $CHR^1CONR^2$, $CHR^1OCO.NR^2$, $CH=CHCH_2O$, $COCHR^1CHR^2O$, or $(R^5)_2P^+CHR^2Q^-$; A, B and E, which may be the same or different are H, hydroxy, halo, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; $R^9$ is substituted phenyl $Q^-$ is a halide anion; n is 0, 1 or 2 and m is 3, 4 or 5; except that when Z is unsubstituted phenyl and X and K are oxygen, A, B and E are not all hydrogen.

Of particular interest are those compounds in which X is O, especially when Z is optionally substituted heteroaryl, S, $SO_2$, NH, $NCH_3$, $NCOCH_3$, $CH(C_6H_5)$, CH(OH), CH=CH, $OCH_2$, $CH_2O$, $CH(CH_3)O$, $S(O)CH_2$, $S(O)_2CH_2$, $SO_2O$, $CO.CH_2O$ or $CO_2CH_2$ and, more particularly, O, $CH_2O$, $OCH_2$, $SO_2O$ or CH(OH).

The compounds of the invention contain at least one carbon-carbon double bond, and are sometimes obtained in the form of mixtures of geometric isomers. However, these mixtures can be separated into individual isomers, and this invention embraces such isomers, and mixtures thereof in all proportions including those which consist substantially of the (Z)-isomer and those which consist substantially of the (E)-isomer.

The individual isomers which result from the unsymmetrically substituted double bond of the propenoate group are identified by the commonly used terms "E" and "Z". These terms are defined according to the Cahn-Ingold-Prelog system which is fully described in the literature (see, for example, J. March, "Advanced Organic Chemistry", 3rd edition, Wiley-Interscience, page 109 et seq).

Usually one isomer is more active fungicidally than the other, the more active isomer usually being the one wherein the groups —$CO_2CH_3$ and —$OCH_3$ are on opposite sides of the olefinic bond of the propenoate group (the (E)-isomer). These (E)-isomers form a preferred embodiment of the invention.

The substituent Z in compound (I) is optionally substituted aryl or optionally substituted heteroaryl. Where valency allows, each of the optionally substituted groups aryl or heteroaryl can carry up to 5 substitutents. The term "aryl" includes phenyl in particular, and naphthyl. The term "heteroaryl" includes 5- and 6-membered heterocyclic groups containing one or more of each of the heteroatoms O, S and N (preferably S or N), fused benzenoid and heteroaromatic ring systems, and, in each case, the corresponding N-oxides. Examples of heteroaryl groups which Z may be are pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4 -triazolyl, thienyl, furyl, pyrrolyl, thiazolyl, oxadiazolyl, quinolinyl, isoquinolinyl, quinoxalinyl, benzothienyl, benzoxazolyl and benzthiazolyl and, where appropriate, the corresponding N-oxides. Substituents which may be present in the optionally substituted aryl and heteroaryl moieties include one or more of the following; halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo($C_{1-4}$)alkyl (especially trifluoromethyl), halo($C_{1-4}$)alkoxy (especially trifluoromethoxy), $C_{1-4}$ alkylthio (especially methylthio), hydroxy($C_{1-4}$)alkyl, $C_{1-4}$-alkoxy($C_{1-4}$)alkyl, $C_{3-6}$cycloalkyl, $C_{3-6}$ cycloalkyl($C_{1-4}$)alkyl, optionally substituted aryl (especially optionally substituted phenyl), optionally substituted heteroaryl (especially optionally substituted pyridinyl or pyrimidinyl), optionally substituted aryloxy (especially optionally substituted phenoxy), optionally substituted heteroaryloxy (especially optionally substituted pyridinyloxy or pyrimidinyloxy), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$)alkyl (especially optionally substituted pyridinyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridinylethenyl or pyrimidinylethenyl), optionally substituted aryl ($C_{1-4}$)alkoxy (especially optionally substituted benzyloxy), optionally substituted heteroaryl($C_{1-4}$)alkoxy (especially optionally substituted pyridinyl- or pyrimidinyl($C_{1-4}$)alkoxy), optionally substituted aryloxy($C_{1-4}$)alkyl(especially phenoxymethyl), optionally substituted heteroaryloxy($C_{1-4}$)alkyl (especially optionally substituted pyridinyloxy- or pyrimidinyloxy($C_{1-4}$)alkyl), acyloxy, including $C_{1-4}$ alkanoyloxy (especially acetyloxy) and benzoyloxy, cyano, thiocyanato, nitro, —NR'R", —NHCOR', —NHCONR'R", —CONR'R", —COOR', —OSO₂R', —SO₂R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Substituents which may be present in the aryl or heteroaryl rings of any of the foregoing substituents and in the phenyl ring of $R^5$ include one or more of the following; halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$-alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzyloxy, cyano, thiocyanato, nitro, —NR'R", —NHCOR', —NHCONR'R", —CONR'R", —COOR', —OSO₂R', —SO₂R', —COR', —CR'=NR" or —N=CR'R" in which R' and R" have the meanings given above.

When any of the substituents A, B and E are $C_{1-4}$-alkyl or $C_{1-4}$ alkoxy, the alkyl moiety can be in the form of straight or branched chains, that is, the moiety may be methyl, ethyl, n- or iso-propyl, or n-, sec-, iso- or t-butyl. Other references herein to $C_{1-4}$ alkyl and $C_{1-4}$ alkoxy carry the same meaning. $C_{2-4}$ Alkenyl groups can be in the form of straight or branched chains and, where appropriate, may have either the (E)- or (Z)-configuration. Examples of such groups are vinyl, allyl, —C(CH₃):CH₂, and (E)- and (Z)-crotyl.

The substituents A and B are preferably in the 4- and 5-positions of the phenyl ring, and the substituent E is preferably a small group or a single atom such as hydrogen or halogen. Usually, E and one or both of A and B will be hydrogen.

In one aspect, the invention includes a compound having the formula (Ia):

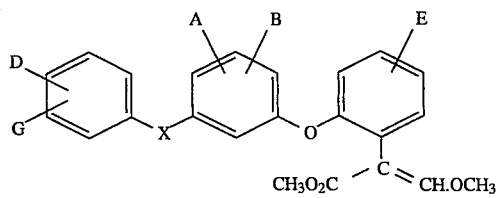

(Ia)

wherein X is O, S(O)$_n$ in which n is 0, 1 or 2, NH, NCH₃, NCH₂CH₃, NCOCH₃, NCH(CH₃)₂, CH₂, CH(CH₃), C(CH₃)₂, CO, C=CH₂, C=C(CH₃)₂, CH₂CH₂, CH(CH₃)CH₂, CH₂CH(CH₃), (E)-CH=CH, (Z)-CH=CH, (E)-C(CH₃)=C(CH₃), C=C, OCH₂, OCH(CH₃), (CH₂)$_p$O in which p is an integer of 1 to 5, CH(CH₃)O, SCH₂, SCH(CH₃), S(O)CH₂, S(O)CH(CH₃), S(O)₂CH₂, S(O)₂CH(CH₃), CH₂S, CH(CH₃)S, CH₂S(O), CH(CH₃)S(O), CH₂S(O)₂, CH(CH₃)S(O)₂, NHCH₂, N(CH₃)CH₂, N(COCH₃)CH₂, NHCH(CH₃), N(CH₃)CH(CH₃), N(COCH₃)CH(CH₃), CH₂NH, CH₂N(CH₃), CH₂N(COCH₃), CH(CH₃)NH, CH(CH₃)N(CH₃), CH(CH₃)N(COCH₃), CO₂, O₂C, SO₂O, OSO₂, CO.CO, COCH₂, COCH(CH₃), CH₂CO, CH(CH₃)CO, CH(OH)CH₂, CH(OH)CH(CH₃), CH₂CH(OH), CH(CH₃)CH(OH), CONH, CON(CH₃), CON(CH₂CH₃), CON(CHO), CON(COCH₃), NHCO, N(CH₃)CO, N(CH₂CH₃)CO, N(CHO)CO, N(COCH₃)CO, CSN(CH₃), CSNH, NHCS, N(CH₃)CS, SO₂NH, SO₂N(CH₃), NHSO₂, N(CH₃)SO₂, N(CH₂CH₃)SO₂, CS₂, S₂C, COS, SCO, (E)-N=N, (E)-N=CH, (E)-N=C(CH₃), (E)-CH₂=N, (E)-C(CH₃)=N, CH₂CH₂CH₂, CH(CH₃)CH₂CH₂, CH₂CH(CH₃)CH₂, CH₂CH₂CH(CH₃), OCH₂CH₂, CH₂OCH₂, SCH₂CH₂, S(O)CH₂CH₂, S(O)₂CH₂CH₂, CH₂SCH₂, CH₂S(O)CH₂, CH₂S(O)₂CH₂, CH₂CH₂S, CH₂CH₂S(O), CH₂CH₂S(O)₂, (E)-CH=NNH, (E)-C(CH₃)=NNH, (E)-CH= NN(CH₃), (E)-NHN=CH, (E)-NHN=C(CH₃), (E)-N(CH₃)N=CH, CH₂CONH, CH(CH₃)CON(CH₃), (E)-CH=CHCH₂O, COCH₂CH₂O,

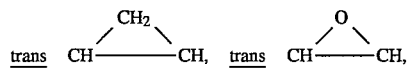

CH(C₆H₅), COCH₂O, CH(OH), CO₂CH₂, (C₆H₅)₂P⁺CH₂Br⁻, CH₂OCO, CH₂NHCO, CH₂SCO, OCH₂O, OCH₂CH₂O, S(O)CH₂O, COCH(CH₃)O, (E)-CH₂ON=CH, (Z)-CH₂ON=CH, CH₂CH₂CH(OH), (E)-CH₂CH=CH, C(CH₃)(OH), CH₂OSO₂, CH₂NHCO.NH, OCO.NH, NHCO.NH or CH₂OCO.NH; A is H, hydroxy, halo, $C_{1-4}$ alkyl, $C_{1-4}$ alkoxy, trifluoromethyl, nitro, cyano, acetyl or phenoxy; B and E are H or halo; D is H, hydroxy, halo, $C_{1-4}$ alkyl, $C_{1-4}$ alkoxy, nitro, cyano, halo($C_{1-4}$)alkyl (especially trifluoromethyl), halo($C_{1-4}$)alkoxy (especially trifluoromethoxy), phenyl phenoxy, NHCOR⁶, NHSO₂R⁶, NR⁷R⁸, CO₂R⁷, wherein R⁶ is $C_{1-4}$ alkyl (especially methyl) or phenyl and R⁷ and R⁸ are independently H or $C_{1-4}$ alkyl, or CH₃O₂C.C=CH.OCH₃; and G is H, halo, $C_{1-4}$ alkyl, $C_{1-4}$ alkoxy or nitro; or D and G, when they are adjacent, join to form a benzene or pyridine ring; provided that when A, B, D, E and G are all H, X is not O. More particularly, it includes a compound having the formula (Ia) wherein X is O, S(O)$_n$ in which n is 0, 1 or 2, CH₂, CH₂CH₂, OCH₂, (CH₂)$_p$O in which p is an integer of 1 to 5, OCH₂O, OCH₂CH₂O, CH(OH), CO, CO₂, O₂C, COS, SCO, CO₂CH₂, SO₂O, (E)-CH=CH, (Z)-CH=CH, (E)-CH=CHCH₂O, CH(CH₃)O, SCH₂, SCH₂O, S(O)CH₂, S(O)CH₂O, S(O)₂CH₂, CONH, NH, NCH₃, CH₂NH, N(CH₃)CH₂, NHCO, CH₂OCO.NH, NCOCH₃, NHSO₂, (E)-N=N, (Z)-N=N, (E)-N=CH, (E)-N(CH₃)N=CH, (E)-CH₂ON=N, (Z)-CH₂ON=CH, CH(C₆H₅), COCH₂O, COCH(CH₃)O, CH₂OCO, CH₂NHCO, CH₂SCO or (C₆H₅)₂P⁺CH₂Br⁻; A is H, hydroxy, halo, $C_{1-4}$ alkyl, $C_{1-4}$ alkoxy, acetyl or phenoxy; B and E are both H; D is H, hydroxy, halo, $C_{1-4}$ alkyl, $C_{1-4}$ alkoxy, nitro, cyano, trifluoromethyl, trifluoromethoxy, phenyl, phenoxy, amino or CH₃O₂C.C=CH.OCH₃; and G is H, halo, $C_{1-4}$ methyl, nitro; or D and G, when they are adjacent, join to form a benzene or pyridine ring; provided that when A, B, D, E and G are all H, X is not O.

In another aspect, the invention includes a compound having the formula (Ib):

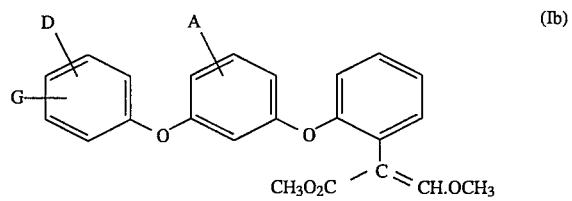

(Ib)

wherein D and G are independently halo, $C_{1-4}$ alkyl, $C_{1-4}$ alkoxy, trifluoromethyl, nitro, cyano, phenyl, phenoxy, NHCOR⁶, NHSO₂R⁶ and NR⁷R⁸ in which R⁶ to R⁸ have the meanings given above; and A is halo, $C_{1-4}$ alkyl, $C_{1-4}$ alkoxy, trifluoromethyl, nitro, cyano, acetyl or phenoxy.

Particularly favoured compounds of the formula (Ib) are those in which D is hydrogen, G is 2- or 3-chloro, 3-bromo, 2- or 4-methoxy, 3- or 4-nitro, 2- or 3-cyano or 3- or 4-phenoxy and A is hydrogen or D and G are both hydrogen and A is 4- or 6-bromo or 4- or 6-acetyl.

In yet another aspect, the invention includes a compound having the formula (Ic):

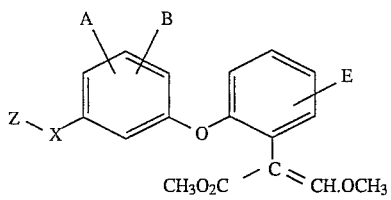

wherein Z is pyridinyl, pyrimidinyl, triazinyl, pyrazinyl, pyridazinyl, quinolinyl, benzoxazolyl, benzthiazolyl, thienyl, quinoxalinyl, thiazolyl, isoquinolinyl, quinazolinyl, purinyl, oxazolyl, thiadiazolyl, oxadiazolyl, furyl, pyrrolyl or thienopyrimidinyl, each optionally substituted with halo, $C_{1-4}$ alkyl, $C_{1-4}$ alkoxy, $C_{1-4}$ alkylthio, halo($C_{1-4}$)alkyl (especially trifluoromethyl), cyano, nitro, $COOR^7$, phenyl phenoxy, $C_{1-4}$ alkanoyl and $CONR^7R^8$ in which $R^7$ and $R^8$ are independently H or $C_{1-4}$ alkyl; and N-oxides thereof; X is O, S, NH, N($CH_3$), $SO_2O$, $CH_2$, $CH_2CH_2$, $OCH_2$, $CH_2O$, CH(OH), CONH or CO; A and B are independently H, halo, $C_{1-4}$ alkyl, $C_{1-4}$ alkoxy, cyano, nitro, halo($C_{1-4}$)alkyl (especially trifluoromethyl) or halo($C_{1-4}$)alkoxy, (especially trifluoromethoxy); and E is H or halo.

More particularly, it includes a compound having the formula (Ic) wherein X is O,S, $OCH_2$, $SO_2O$, $CH_2$, $CH_2O$, CONH or CON($CH_3$); Z is pyridin-2-yl, pyrimidin-2-yl, pyrimidin-4-yl, pyrimidin-5-yl, pyrazin-2-yl, pyridazin-3-yl, 1,3,5-triazin-2-yl, thien-2-yl, pyrrol-2-yl, quinolin-2-yl, quinoxalin-2-yl, 1,2,4-triazol-1-yl, thiazol-4-yl, benzthiazol-2-yl, or benzoxazol-2-yl, each optionally substituted with halogen, trifluoromethyl, $C_{1-4}$ alkyl, $C_{1-4}$ alkoxy, cyano or nitro, and N-oxides thereof and A, B and E are all H.

In still yet another aspect, the invention includes a compound having the formula (Id):

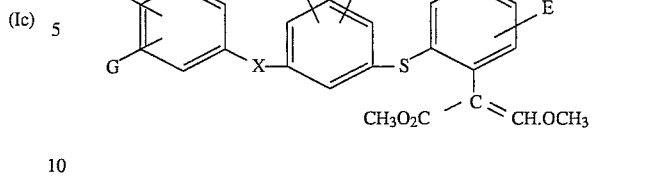

wherein X, A, B, D, E and G have the meanings given for the compound (Ia) and also wherein X is O and A, B, D and E are all H.

Compounds having the formula (Id) of particular interest are those wherein X is O, $CH_2O$ or $SO_2O$ and A, B, D, E and G are all H or D is 2- or 4-nitro.

In still yet another aspect, the invention includes a compound having the formula (Ie):

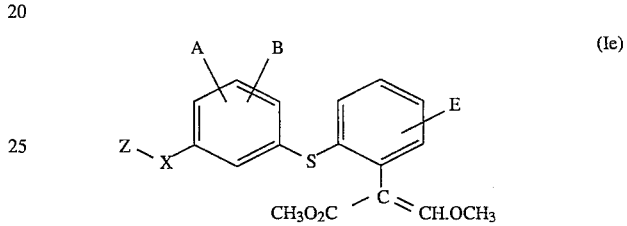

wherein Z, X, A, B and E have the meanings given for the compound (Ic). Compounds having the formula (Ie) of particular interest are those wherein Z is pyrimidin-2-yl or pyrimidin-5-yl, X is O and A, B and E are all H.

The invention is illustrated by the compounds listed in Tables I, II, III and IV which follow. Throughout Tables I, II, III and IV the methyl 3-methoxypropenoate group has the (E)-configuration.

TABLE I

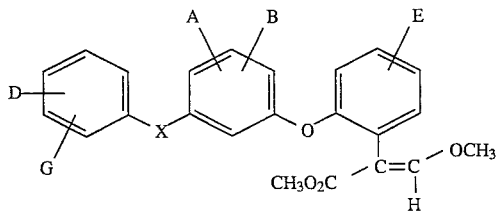

| Compound No. | X | D | G | A | B | E | Olefinic+ | Melting Point (°C.) |
|---|---|---|---|---|---|---|---|---|
| 1 | S | H | H | H | H | H | 7.42 | Gum |
| 2 | SO | H | H | H | H | H | Obscured | Gum |
| 3 | $SO_2$ | H | H | H | H | H | Obscured | Wax |
| 4 | NH | H | H | H | H | H | 7.44 | Wax |
| 5 | $NCH_3$ | H | H | H | H | H | 7.44 | Gum |
| 6 | $NCH_2CH_3$ | H | H | H | H | H | | |
| 7 | $NCOCH_3$ | H | H | H | H | H | 7.39 | 50–54 |
| 8 | $NCH(CH_3)_2$ | H | H | H | H | H | | |
| 9 | $CH_2$ | H | H | H | H | H | 7.47 | Gum |
| 10 | $CH(CH_3)$ | H | H | H | H | H | | |
| 11 | $C(CH_3)_2$ | H | H | H | H | H | | |
| 12 | CO | H | H | H | H | H | 7.47 | Gum |
| 13 | $C:CH_2$ | H | H | H | H | H | | |
| 14 | $C:C(CH_3)_2$ | H | H | H | H | H | | |
| 15 | $CH_2CH_2$ | H | H | H | H | H | 7.49 | Gum |
| 16 | $CH(CH_3)CH_2$ | H | H | H | H | H | | |
| 17 | $CH_2CH(CH_3)$ | H | H | H | H | H | | |
| 18 | (E)-CH:CH | H | H | H | H | H | 7.49 | Gum |

TABLE I-continued

| | | | | | | | | |
|---|---|---|---|---|---|---|---|---|
| 19 | (E)-C(CH$_3$):C(CH$_3$) | H | H | H | H | H | | |
| 20 | C:C | H | H | H | H | H | | |
| 21 | OCH$_2$ | H | H | H | H | H | 7.46 | Gum |
| 22 | OCH(CH$_3$) | H | H | H | H | H | | |
| 23 | CH$_2$O | H | H | H | H | H | 7.44 | 84 |
| 24 | CH(CH$_3$)O | H | H | H | H | H | 7.39 | 99–102 |
| 25 | SCH$_2$ | H | H | H | H | H | 7.47 | Gum |
| 26 | SCH(CH$_3$) | H | H | H | H | H | | |
| 27 | S(O)CH$_2$ | H | H | H | H | H | 7.48 | 82–86 |
| 28 | S(O)CH(CH$_3$) | H | H | H | H | H | | |
| 29 | S(O)$_2$CH$_2$ | H | H | H | H | H | 7.48 | 140–144 |
| 30 | S(O)$_2$CH(CH$_3$) | H | H | H | H | H | | |
| 31 | CH$_2$S | H | H | H | H | H | | |
| 32 | CH(CH$_3$)S | H | H | H | H | H | | |
| 33 | CH$_2$S(O) | H | H | H | H | H | | |
| 34 | CH(CH$_3$)S(O) | H | H | H | H | H | | |
| 35 | CH$_2$S(O)$_2$ | H | H | H | H | H | | |
| 36 | CH(CH$_3$)S(O)$_2$ | H | H | H | H | H | | |
| 37 | NHCH$_2$ | H | H | H | H | iH | | |
| 38 | N(CH$_3$)CH$_2$ | H | H | H | H | H | 7.44 | Gum |
| 39 | N(COCH$_3$)CH$_2$ | H | H | H | H | H | | |
| 40 | NHCH(CH$_3$) | H | H | H | H | H | | |
| 41 | N(CH$_3$)CH(CH$_3$) | H | H | H | H | H | | |
| 42 | N(COCH$_3$)CH(CH$_3$) | H | H | H | H | H | | |
| 43 | CH$_2$NH | H | H | H | H | H | | |
| 44 | CH$_2$N(CH$_3$) | H | H | H | H | H | | |
| 45 | CH$_2$N(COCH$_3$) | H | H | H | H | H | | |
| 46 | CH(CH$_3$)NH | H | H | H | H | H | | |
| 47 | CH(CH$_3$)N(CH$_3$) | H | H | H | H | H | | |
| 48 | CH(CH$_3$)N(COCH$_3$) | H | H | H | H | H | | |
| 49 | CO$_2$ | H | H | H | H | H | 7.46 | 94–95 |
| 50 | O$_2$C | H | H | H | H | H | 7.47 | Oil |
| 51 | SO$_2$O | H | H | H | H | H | 7.40 | Gum |
| 52 | OSO$_2$ | H | H | H | H | H | | |
| 53 | CO.CO | H | H | H | H | H | | |
| 54 | COCH$_2$ | H | H | H | H | H | | |
| 55 | COCH(CH$_3$) | H | H | H | H | H | | |
| 56 | CH$_2$CO | H | H | H | H | H | | |
| 57 | CH(CH$_3$)CO | H | H | H | H | H | | |
| 58 | CH(OH)CH$_2$ | H | H | H | H | H | | |
| 59 | CH(OH)CH(CH$_3$) | H | H | H | H | H | | |
| 60 | CH$_2$CH(OH) | H | H | H | H | H | | |
| 61 | CH(CH$_3$)CH(OH) | H | H | H | H | H | | |
| 62 | CONH | H | H | H | H | H | 7.46 | Gum |
| 63 | CON(CH$_3$) | H | H | H | H | H | | |
| 64 | CCN(CH$_2$CH$_2$CH$_3$) | H | H | H | H | H | | |
| 65 | CON(CHO) | H | H | H | H | H | | |
| 66 | CON(COCH$_3$) | H | H | H | H | H | | |
| 67 | NHCO | H | H | H | H | H | 7.40 | Gum |
| 68 | N(CH$_3$)CO | H | H | H | H | H | | |
| 69 | N(CH$_2$CH$_3$)CO | H | H | H | H | H | | |
| 70 | N(CHO)CO | H | H | H | H | H | | |
| 71 | N(COCH$_3$)CO | H | H | H | H | H | | |
| 72 | CSN(CH$_3$) | H | H | H | H | H | | |
| 73 | CSNH | H | H | H | H | H | | |
| 74 | NHCS | H | H | H | H | H | | |
| 75 | N(CH$_3$)CS | H | H | H | H | H | | |
| 76 | SO$_2$NH | H | H | H | H | H | | |
| 77 | SO$_2$N(CH$_3$) | H | H | H | H | H | | |
| 78 | NHSO$_2$ | H | H | H | H | H | 7.43 | Oil |
| 79 | N(CH$_3$)SO$_2$ | H | H | H | H | H | | |
| 80 | N(CH$_2$CH$_3$)SO$_2$ | H | H | H | H | H | | |
| 81 | CS$_2$ | H | H | H | H | H | | |
| 82 | S$_2$C | H | H | H | H | H | | |
| 83 | COS | H | H | H | H | H | 7.38 | 87–91 |
| 84 | SCO | H | H | H | H | H | 7.50 | Gum |
| 85 | (E)-N:N | H | H | H | H | H | | |
| 86 | (E)-N:CH | H | H | H | H | H | | |
| 87 | (E)-N:C(CH$_3$) | H | H | H | H | H | 7.49 or 7.50 | Gum |
| 88 | (E)-CH:N | H | H | H | H | H | | |
| 89 | (E)-C(CH$_3$):N | H | H | H | H | H | | |
| 90 | CH$_2$CH$_2$CH$_2$ | H | H | H | H | H | | |
| 91 | CH(CH$_3$)CH$_2$CH$_2$ | H | H | H | H | H | | |
| 92 | CH$_2$CH(CH$_3$)CH$_2$ | H | H | H | H | H | | |
| 93 | CH$_2$CH$_2$CH(CH$_3$) | H | H | H | H | H | | |
| 94 | OCH$_2$CH$_2$ | H | H | H | H | H | | |
| 95 | CH$_2$OCH$_2$ | H | H | H | H | H | | |
| 96 | CH$_2$CH$_2$O | H | H | H | H | H | 7.48 | Oil |
| 97 | SCH$_2$CH | H | H | H | H | H | | |

TABLE I-continued

| | | | | | | | | |
|---|---|---|---|---|---|---|---|---|
| 98 | S(O)CH$_2$CH$_2$ | H | H | H | H | H | | |
| 99 | S(O)$_2$CH$_2$CH$_2$ | H | H | H | H | H | | |
| 100 | CH$_2$SCH$_2$ | H | H | H | H | H | | |
| 101 | CH$_2$S(O)CH$_2$ | H | H | H | H | H | | |
| 102 | CH$_2$S(O)$_2$CH$_2$ | H | H | H | H | H | | |
| 103 | CH$_2$CH$_2$S | H | H | H | H | H | | |
| 104 | CH$_2$CH$_2$S(O) | H | H | H | H | H | | |
| 105 | CH$_2$CH$_2$S(O)$_2$ | H | H | H | H | H | | |
| 106 | (E)-CH:NNH | H | H | H | H | H | | |
| 107 | (E)-C(CH$_3$):NNH | H | H | H | H | H | | |
| 108 | (E)-CH:NN(CH$_3$) | H | H | H | H | H | | |
| 109 | (E)-NHN:CH | H | H | H | H | H | | |
| 110 | (E)-NHN:C(CH$_3$) | H | H | H | H | H | | |
| 111 | (E)-N(CH$_3$)N:CH | H | H | H | H | H | 7.50 | 121.5–123.5 |
| 112 | CH$_2$CONH | H | H | H | H | H | | |
| 113 | CH(CH$_3$)CON(CH$_3$) | H | H | H | H | H | | |
| 114 | CH(CH$_3$)CON(CH$_3$) | H | H | H | H | H | | |
| 115 | (E)-CH:CHCH$_2$O | H | H | H | H | H | 7.47 | Gum |
| 116 | COCH$_2$CH$_2$O | H | H | H | H | H | | |
| 117 | trans CH—CH (CH$_2$) | H | H | H | H | H | | |
| 118 | trans CH—CH (O) | H | H | H | H | H | | |
| 119 | O | 2-Cl | H | H | H | H | 7.48 | 51–54 |
| 120 | O | 3-Cl | H | H | H | H | 7.48 | Gum |
| 121 | O | 4-Cl | H | H | H | H | | |
| 122 | O | 2-F | H | H | H | H | 7.50 | Gum |
| 123 | O | 3-F | H | H | H | H | 7.51 | Gum |
| 124 | O | 4-F | H | H | H | H | 7.35 | Gum |
| 125 | O | 2-CH$_3$ | H | H | H | H | 7.51 | Gum |
| 126 | O | 3-CH$_3$ | H | H | H | H | 7.49 | Gum |
| 127 | O | 4-CH$_3$ | H | H | H | H | 7.49 | Gum |
| 128 | O | 2-CH$_3$O | H | H | H | H | 7.46 | Gum |
| 129 | O | 3-CH$_3$O | H | H | H | H | 7.48 | Gum |
| 130 | O | 4-CH$_3$O | H | H | H | H | 7.48 | Gum |
| 131 | O | 2-CH$_2$ | H | H | H | H | 7.47 | Gum |
| 132 | O | 3-NO$_2$ | H | H | H | H | 7.49 | Gum |
| 133 | O | 4-NO$_2$ | H | H | H | H | 7.44 | 67–71 |
| 134 | O | 2-CN | H | H | H | H | 7.51 | 108–110 |
| 135 | O | 3-CN | H | H | H | H | 7.51 | Gum |
| 136 | O | 4-CN | H | H | H | H | | |
| 137 | O | 2-Br | H | H | H | H | | |
| 138 | O | 3-Br | H | H | H | H | 7.48 | Gum |
| 139 | O | 4-Br | H | H | H | H | | |
| 140 | O | 2-CF$_3$ | H | H | H | H | | |
| 141 | O | 3-CF$_3$ | H | H | H | H | 7.49 | Oil |
| 142 | O | 4-CF$_3$ | H | H | H | H | | |
| 143 | O | 2-C$_6$H$_5$O | H | H | H | H | 7.46 | Gum |
| 144 | O | 3-C$_6$H$_5$O | H | H | H | H | 7.48 | Gum |
| 145 | O | 4-C$_6$H$_5$O | H | H | H | H | 7.50 | Gum |
| 146 | O | 2-CH$_3$CH$_2$O | H | H | H | H | | |
| 147 | O | 3-CH$_3$CH$_2$O | H | H | H | H | | |
| 148 | O | 4-CH$_3$CH$_2$O | H | H | H | H | | |
| 149 | O | 2-C$_6$H$_5$ | H | H | H | H | | |
| 150 | O | 3-C$_6$H$_5$ | H | H | H | H | 7.50 | Gum |
| 151 | O | 4-C$_6$H$_5$ | H | H | H | H | | |
| 152 | O | 2-Cl | 3-Cl | H | H | H | | |
| 153 | O | 2-Cl | 4-Cl | H | H | H | | |
| 154 | O | 2-Cl | 5-Cl | H | H | H | | |
| 155 | O | 2-Cl | 6-Cl | H | H | H | | |
| 156 | O | 3-Cl | 4-Cl | H | H | H | | |
| 157 | O | 3-Cl | 5-Cl | H | H | H | 7.53 | Gum |
| 158 | O | 2-Cl | 3-CH$_3$O | H | H | H | | |
| 159 | O | 2-Cl | 4-CH$_3$O | H | H | H | | |
| 160 | O | 2-Cl | 5-CH$_3$O | H | H | H | | |
| 161 | O | 2-Cl | 6-CH$_3$O | H | H | H | | |
| 162 | O | 3-Cl | 4-CH$_3$O | H | H | H | | |
| 163 | O | 3-Cl | 5-CH$_3$O | H | H | H | | |
| 164 | O | 2-CH$_3$O | 3-Cl | H | H | H | | |
| 165 | O | 2-CH$_3$O | 4-Cl | H | H | H | | |
| 166 | O | 2-CH$_3$O | 5-Cl | H | H | H | | |
| 167 | O | 3-CH$_3$O | 4-Cl | H | H | H | | |
| 168 | O | ⊕ | ⊕ | H | H | H | | |
| 169 | O | ⊕ | ⊕ | H | H | H | | |

TABLE I-continued

| | | | | | | | | |
|---|---|---|---|---|---|---|---|---|
| 170 | O | H | H | 2-F | H | H | | |
| 171 | O | H | H | 4-F | H | H | 7.51 | Gum |
| 172 | O | H | H | 5-F | H | H | | |
| 173 | O | H | H | 6-F | H | H | | |
| 174 | O | H | H | 4-Cl | H | H | | |
| 175 | O | H | H | 5-Cl | H | H | 7.41 | Gum |
| 176 | O | H | H | 4-CH$_3$ | H | H | | |
| 177 | O | H | H | 5-CH$_3$ | H | H | 7.47 | Gum |
| 178 | O | H | H | 4-CH$_3$O | H | H | | |
| 179 | O | H | H | 5-CH$_3$O | H | H | 7.42 | Gum |
| 180* | O | H | H | 4-Br | H | H | 7.47 | Gum |
| 181 | O | H | H | 5-Br | H | H | | |
| 182 | O | H | H | 4-CF$_3$ | H | H | | |
| 183 | O | H | H | 5-CF$_3$ | H | H | | |
| 184 | O | H | H | 4-NO$_2$ | H | H | | |
| 185 | O | H | H | 5-NO$_2$ | H | H | | |
| 186 | O | H | H | 4-CN | H | H | | |
| 187 | O | H | H | 5-CN | H | H | | |
| 188 | O | H | H | 4-F | 5-F | H | | |
| 189 | O | H | H | 4-Cl | 5-Cl | H | | |
| 190 | O | H | H | 4-F | 5-Cl | H | | |
| 191 | O | H | H | 4-Cl | 5-F | H | | |
| 192 | O | H | H | 4-CH$_3$O | 5-Cl | H | | |
| 193 | O | H | H | 4-CH$_3$O | 5-F | H | | |
| 194 | O | H | H | H | H | 5-F | | |
| 195 | O | H | H | H | H | 6-Cl | | |
| 196 | (E)-N:N | H | H | 4-CH$_3$O | H | H | | |
| 197 | (E)-N:N | H | H | 4-CH$_3$CH$_2$O | H | H | | |
| 198 | CH$_2$O | 2-Cl | H | H | H | H | | |
| 199 | CH$_2$O | 3-Cl | H | H | H | H | | |
| 200 | CH$_2$O | 4-Cl | H | H | H | H | | |
| 201 | CH$_2$O | 2-F | H | H | H | H | | |
| 202 | CH$_2$O | 3-F | H | H | H | H | | |
| 203 | CH$_2$O | 4-F | H | H | H | H | | |
| 204 | CH$_2$O | 2-CH$_3$ | H | H | H | H | 7.25 | 108–110 |
| 205 | CH$_2$O | 3-CH$_3$ | H | H | H | H | 7.24 | Gum |
| 206 | CH$_2$O | 4-CH$_3$ | H | H | H | H | 7.40 | 88–90 |
| 207 | CH$_2$O | 2-CH$_3$O | H | H | H | H | | |
| 208 | CH$_2$O | 3-CH$_3$O | H | H | H | H | 7.39 | Gum |
| 209 | CH$_2$O | 4-CH$_3$O | H | H | H | H | | |
| 210 | CH$_2$O | 2-NO$_2$ | H | H | H | H | | |
| 211 | CH$_2$O | 3-NO$_2$ | H | H | H | H | | |
| 212 | CH$_2$O | 4-NO$_2$ | H | H | H | H | 7.42 | 109 |
| 213 | CH$_2$O | 2-CN | H | H | H | H | | |
| 214 | CH$_2$O | 3-CN | H | H | H | H | 7.41 | 89–92.5 |
| 215 | CH$_2$O | 4-CN | H | H | H | H | | |
| 216 | CH$_2$O | 2-Br | H | H | H | H | 7.41 | 78–80 |
| 217 | CH$_2$O | 3-Br | H | H | H | H | 7.45 | Gum |
| 218 | CH$_2$O | 4-Br | H | H | H | H | 7.4 | 86–88.5 |
| 219 | CH$_2$O | 2-CF$_3$ | H | H | H | H | | |
| 220 | CH$_2$O | 3-CF$_3$ | H | H | H | H | obscured | Gum |
| 221 | CH$_2$O | 4-CF$_3$ | H | H | H | H | | |
| 222 | CH$_2$O | 2-C$_6$H$_5$O | H | H | H | H | | |
| 223 | CH$_2$O | 3-C$_6$H$_5$O | H | H | H | H | | |
| 224 | CH$_2$O | 4-C$_6$H$_5$O | H | H | H | H | | |
| 225 | CH$_2$O | 2-CH$_3$CH$_2$O | H | H | H | H | | |
| 226 | CH$_2$O | 3-CH$_3$CH$_2$O | H | H | H | H | | |
| 227 | CH$_2$O | 4-CH$_3$CH$_2$O | H | H | H | H | | |
| 228 | CH$_2$O | 2-C$_6$H$_5$ | H | H | H | H | | |
| 229 | CH$_2$O | 3-C$_6$H$_5$ | H | H | H | H | | |
| 230 | CH$_2$O | 4-C$_6$H$_5$ | H | H | H | H | obscured | Gum |
| 231 | CH$_2$O | 2-Cl | 3-Cl | H | H | H | | |
| 232 | CH$_2$O | 2-Cl | 4-Cl | H | H | H | | |
| 233 | CH$_2$O | 2-Cl | 5-Cl | H | H | H | | |
| 234 | CH$_2$O | 2-Cl | 6-Cl | H | H | H | | |
| 235 | CH$_2$O | 3-Cl | 4-Cl | H | H | H | | |
| 236 | CH$_2$O | 3-Cl | 5-Cl | H | H | H | | |
| 237 | CH$_2$O | 2-Cl | 3-CH$_3$O | H | H | H | | |
| 238 | CH$_2$O | 2-Cl | 4-CH$_3$O | H | H | H | | |
| 239 | CH$_2$O | 2-Cl | 5-CH$_3$O | H | H | H | | |
| 240 | CH$_2$O | 2-Cl | 6-CH$_3$O | H | H | H | | |
| 241 | CH$_2$O | 3-Cl | 4-CH$_3$O | H | H | H | | |
| 242 | CH$_2$O | 3-Cl | 5-CH$_3$O | H | H | H | | |
| 243 | CH$_2$O | 2-CH$_3$O | 3-Cl | H | H | H | | |
| 244 | CH$_2$O | 2-CH$_3$O | 4-Cl | H | H | H | | |
| 245 | CH$_2$O | 2-CH$_3$O | 5-Cl | H | H | H | | |
| 246 | CH$_2$O | 3-CH$_3$O | 4-Cl | H | H | H | | |
| 247 | CH$_2$O | ⊕ | ⊕ | H | H | H | 7.42 | 100–102.5 |
| 248 | CH$_2$O | ⊕ | ⊕ | H | H | H | 7.42 | 102–106 |

TABLE I-continued

| | | | | | | | | |
|---|---|---|---|---|---|---|---|---|
| 249 | CH₂O | H | H | 2-F | H | H | | |
| 250 | CH₂O | H | H | 4-F | H | H | | |
| 251 | CH₂O | H | H | 5-F | H | H | | |
| 252 | CH₂O | H | H | 6-F | H | H | | |
| 253 | CH₂O | H | H | 4-Cl | H | H | | |
| 254 | CH₂O | H | H | 5-Cl | H | H | | |
| 255 | CH₂O | H | H | 4-CH₃ | H | H | | |
| 256 | CH₂O | H | H | 5-CH₃ | H | H | | |
| 257 | CH₂O | H | H | 4-CH₃O | H | H | | |
| 258 | CH₂O | H | H | 5-CH₃O | H | H | | |
| 259 | CH₂O | H | H | 4-Br | H | H | | |
| 260 | CH₂O | H | H | 5-Br | H | H | | |
| 261 | CH₂O | H | H | 4-CF₃ | H | H | | |
| 262 | CH₂O | H | H | 5-CF₃ | H | H | | |
| 263 | CH₂O | H | H | 4-NO₂ | H | H | | |
| 264 | CH₂O | H | H | 5-NO₂ | H | H | | |
| 265 | CH₂O | H | H | 4-CN | H | H | | |
| 266 | CH₂O | H | H | 5-CN | H | H | | |
| 267 | CH₂O | H | H | 4-F | 5-F | H | | |
| 268 | CH₂O | H | H | 4-Cl | 5-Cl | H | | |
| 269 | CH₂O | H | H | 4-F | 5-Cl | H | | |
| 270 | CH₂O | H | H | 4-Cl | 5-F | H | | |
| 271 | CH₂O | H | H | 4-CH₃O | 5-Cl | H | | |
| 272 | CH₂O | H | H | 4-CH₃O | 5-F | H | | |
| 273 | CH₂O | H | H | H | H | 5-F | | |
| 274 | CH₂O | H | H | H | H | 6-Cl | | |
| 275 | O | 4-NH.COCH₃ | H | H | H | H | | |
| 276 | O | 4-NH.SO₂C₆H₅ | H | H | H | H | | |
| 277 | O | 4-NH.COC₆H₅ | H | H | H | H | | |
| 278 | O | 4-NH.SO₂CH₃ | H | H | H | H | | |
| 279 | O | 4-N(CH₃)₂ | H | H | H | H | | |
| 280 | SO₂O | 4-NH.COCH₃ | H | H | H | H | | |
| 281 | SO₂O | 3-NO₂ | 4-Cl | H | H | H | | |
| 282 | (E)-N:N | 4-Cl | H | 4-HO | H | H | 7.38 | 143–144 |
| 283 | SO₂O | 2-Cl | H | H | H | H | 7.37 | Gum |
| 284 | SO₂O | 3-Cl | H | H | H | H | 7.45 | Gum |
| 285 | SO₂O | 4-Cl | H | H | H | H | 7.45 | 53–59 |
| 286 | SO₂O | 2-F | H | H | H | H | | |
| 287 | SO₂O | 3-F | H | H | H | H | | |
| 288 | SO₂O | 4-F | H | H | H | H | 7.45 | Gum |
| 289 | SO₂O | 2-CH₃ | H | H | H | H | | |
| 290 | SO₂O | 3-CH₃ | H | H | H | H | 7.34 | Gum |
| 291 | SO₂O | 4-CH₃ | H | H | H | H | 7.38 | 70–76 |
| 292 | SO₂O | 2-CH₃O | H | H | H | H | | |
| 293 | SO₂O | 3-CH₃O | H | H | H | H | | |
| 294 | SO₂O | 4-CH₃O | H | H | H | H | 7.39 | 96–97 |
| 295 | SO₂O | 2-NO₂ | H | H | H | H | 7.40 | Gum |
| 296 | SO₂O | 3-NO₂ | H | H | H | H | 7.41 | 90–93.5 |
| 297 | SO₂O | 4-NO₂ | H | H | H | H | | |
| 298 | SO₂O | 2-CN | H | H | H | H | | |
| 299 | SO₂O | 3-CN | H | H | H | H | | |
| 300 | SO₂O | 4-CN | H | H | H | H | | |
| 301 | SO₂O | 2-Br | H | H | H | H | | |
| 302 | SO₂O | 3-Br | H | H | H | H | | |
| 303 | SO₂O | 4-Br | H | H | H | H | | |
| 304 | SO₂O | 2-CF₃ | H | H | H | H | | |
| 305 | SO₂O | 3-CF₃ | H | H | H | H | | |
| 306 | SO₂O | 4-CF₃ | H | H | H | H | | |
| 307 | SO₂O | 2-C₆H₅O | H | H | H | H | | |
| 308 | SO₂O | 3-C₆H₅O | H | H | H | H | | |
| 309 | SO₂O | 4-C₆H₅O | H | H | H | H | | |
| 310 | SO₂O | 2-CH₃CH₂O | H | H | H | H | | |
| 311 | SO₂O | 3-CH₃CH₂O | H | H | H | H | | |
| 312 | SO₂O | 4-CH₃CH₂O | H | H | H | H | | |
| 313 | SO₂O | 2-C₆H₅ | H | H | H | H | | |
| 314 | SO₂O | 3-C₆H₅ | H | H | H | H | | |
| 315 | SO₂O | 4-C₆H₅ | H | H | H | H | | |
| 316 | SO₂O | 2-Cl | 3-Cl | H | H | H | | |
| 317 | SO₂O | 2-Cl | 4-Cl | H | H | H | | |
| 318 | SO₂O | 2-Cl | 5-Cl | H | H | H | 7.53 | Gum |
| 319 | SO₂O | 2-Cl | 6-Cl | H | H | H | | |
| 320 | SO₂O | 3-Cl | 4-Cl | H | H | H | | |
| 321 | SO₂O | 3-Cl | 5-Cl | H | H | H | | |
| 322 | SO₂O | 2-Cl | 3-CH₃O | H | H | H | | |
| 323 | SO₂O | 2-Cl | 4-CH₃O | H | H | H | | |
| 324 | SO₂O | 2-Cl | 5-CH₃O | H | H | H | | |
| 325 | SO₂O | 2-Cl | 6-CH₃O | H | H | H | | |
| 326 | SO₂O | 3-Cl | 4-CH₃O | H | H | H | | |
| 327 | SO₂O | 3-Cl | 5-CH₃O | H | H | H | | |

TABLE I-continued

| | | | | | | | | |
|---|---|---|---|---|---|---|---|---|
| 328 | SO₂O | 2-CH₃O | 3-Cl | H | H | H | | |
| 329 | SO₂O | 2-CH₃O | 4-Cl | H | H | H | | |
| 330 | SO₂O | 2-CH₃O | 5-Cl | H | H | H | | |
| 331 | SO₂O | 3-CH₃O | 4-Cl | H | H | H | | |
| 332 | SO₂O | ⊕ | ⊕ | H | H | H | 7.34 | Gum |
| 333 | SO₂O | ⊕ | ⊕ | H | H | H | 7.35 | 98–100 |
| 334 | SO₂O | H | H | 2-F | H | H | | |
| 335 | SO₂O | H | H | 4-F | H | H | | |
| 336 | SO₂O | H | H | 5-F | H | H | | |
| 337 | SO₂O | H | H | 6-F | H | H | | |
| 338 | SO₂O | H | H | 4-Cl | H | H | | |
| 339 | SO₂O | H | H | 5-Cl | H | H | | |
| 340 | SO₂O | H | H | 4-CH₃ | H | H | | |
| 341 | SO₂O | H | H | 5-CH₃ | H | H | | |
| 342 | SO₂O | H | H | 4-CH₃ | H | H | | |
| 343 | SO₂O | H | H | 5-CH₃ | H | H | | |
| 344 | SO₂O | H | H | 4-Br | H | H | | |
| 345 | SO₂O | H | H | 5-Br | H | H | | |
| 346 | SO₂O | H | H | 4-CF₃ | H | H | | |
| 347 | SO₂O | H | H | 5-CF₃ | H | H | | |
| 348 | SO₂O | H | H | 4-NO₂ | H | H | | |
| 349 | SO₂O | H | H | 5-NO₂ | H | H | | |
| 350 | SO₂O | H | H | 4-CN | H | H | | |
| 351 | SO₂O | H | H | 5-CN | H | H | | |
| 352 | SO₂O | H | H | 4-F | 5-F | H | | |
| 353 | SO₂O | H | H | 4-Cl | 5-Cl | H | | |
| 354 | SO₂O | H | H | 4-F | 5-Cl | H | | |
| 355 | SO₂O | H | H | 4-Cl | 5-F | H | | |
| 356 | SO₂O | H | H | 4-CH₃O | 5-Cl | H | | |
| 357 | SO₂O | H | H | 3-CH₃O | 5-F | H | | |
| 358 | SO₂O | H | H | H | H | 5-F | | |
| 359 | SO₂O | H | H | H | H | 6-Cl | | |
| 360 | CH(C₆H₅) | H | H | H | H | H | 7.44 | Gum |
| 361 | O | 3-Cl | H | 4-Cl | H | H | | |
| 362 | O | 3-CH₃O | 4-Cl | 5-F | H | H | | |
| 363 | CH₂O | 4-F | H | 5-CH₃O | H | H | | |
| 364 | SO₂O | 3-CH₃ | H | 4-F | H | H | | |
| 365⊕ | O | H | H | 4-CH₃CO | H | H | 7.43 | 90–92 |
| 366⊕ | O | H | H | 6-CH₃CO | H | H | 7.48 | 82–85 |
| 367* | O | H | H | 6-Br | H | H | 7.45 | Gum |
| 368 | O | H | H | 5-C₆H₅O | H | H | 7.46 | Gum |
| 369 | SO₂O | 3-NH₂ | H | H | H | H | 7.43 | 88–92 |
| 370 | COCH₂O | H | H | H | H | H | 7.47 | 49–52 |
| 371 | OCH₂ | 4-CH₃O | H | H | H | H | 7.49 | 66–69 |
| 372 | OCH₂ | 3-CH₃O | H | H | H | H | 7.47 | Gum |
| 373 | OCH₂ | 3-CN | H | H | H | H | 7.48 | 71–75 |
| 374 | OCH₂ | 4-CN | H | H | H | H | 7.48 | Gum |
| 375 | OCH₂ | 4-NO₂ | H | H | H | H | 7.48 | 108–110 |
| 376 | OCH₂ | 2-Cl | H | H | H | H | 7.46 | 83–87 |
| 377 | OCH₂ | 2-CH₃O | H | H | H | H | 7.48 | Gum |
| 378 | OCH₂ | 2-CN | H | H | H | H | 7.47 | 95–10 |
| 379 | (E)-N:N | 4-Cl | H | 4-CH₃O | H | H | obscured | 61 |
| 380 | CH(OH) | H | H | H | H | H | 7.45 | Gum |
| 381 | OCH₂ | 2-NO₂ | H | H | H | H | 7.48 | Gum |
| 382 | OCH₂ | 3-NO₂ | H | H | H | H | 7.48 | Gum |
| 383 | OCH₂ | 3-Br | H | H | H | H | 7.47 | Oil |
| 384 | OCH₂ | 3-Cl | H | H | H | H | 7.40 | Oil |
| 385 | OCH₂ | 3-C₆H₅O | H | H | H | H | 7.47 | Oil |
| 386 | OCH₂ | 4-Cl | H | H | H | H | 7.47 | 72–76 |
| 387 | S(O)CH₂ | 4-Cl | H | H | H | H | 7.42 | 105–11 |
| 388 | S(O)₂CH₂ | 4-Cl | H | H | H | H | 7.47 | 126–130.5 |
| 389 | OCH₂ | 2-Br | H | H | H | H | 7.46 | 87.5–9 |
| 390 | O | 2-NO₂ | 4-NO₂ | H | H | H | 7.46 | 54–57 |
| 391 | O | 2-Me | 3-Me | H | H | H | 7.50 | Gum |
| 392 | O | 2-Me | 4-Me | H | H | H | 7.51 | Gum |
| 393 | O | 2-Me | 5-Me | H | H | H | 7.50 | Gum |
| 394 | O | 2-Me | 6-Me | H | H | H | 7.50 | Gum |
| 395 | O | 3-Me | 4-Me | H | H | H | 7.50 | Gum |
| 396 | O | 3-Me | 5-Me | H | H | H | 7.51 | Wax |
| 397 | OCH₂ | 4-Br | H | H | H | H | 7.47 | Oil |
| 398 | CO₂CH₂ | H | H | H | H | H | 7.47 | Gum |
| 399 | SCH₂ | 2-Cl | H | H | H | H | 7.47 | 74–78 |
| 400 | SCH₂ | 4-NO₂ | H | H | H | H | 7.48 | Gum |
| 401 | S(O)CH₂ | 2-Cl | H | H | H | H | 7.60 | Gum |
| 402 | S(O)₂CH₂ | 2-Cl | H | H | H | H | 7.59 | Gum |
| 403 | (E/Z)-CH=CH* | 4-NO₂ | H | H | H | H | 7.49 | Gum |
| 404 | Ph₂⁺PCH₂Br⁻ | H | H | H | H | H | 7.40 | 176–177 |
| 405 | CH₂O | 4-tert-C₄H₉ | H | H | H | H | 7.31 | Gum |
| 406 | CH₂OCO | H | H | H | H | H | 7.46 | Gum |

TABLE I-continued

| | | | | | | | | |
|---|---|---|---|---|---|---|---|---|
| 407 | CH₂NHCO | H | H | H | H | H | 7.41 | Gum |
| 408 | CH₂SCO | H | H | H | H | H | 7.45 | Gum |
| 409 | O₂C | 3-NO₂ | H | H | H | H | 7.50 | Gum |
| 410 | OCH₂O | 4-Cl | H | H | H | H | 7.47 | Oil |
| 411 | S(O)CH₂O | H | H | H | H | H | 7.47 | Oil |
| 412 | COCH(CH₃)O | H | H | H | H | H | 7.45 | Oil |
| 413 | (E)-CH₂ON:CH | H | H | H | H | H | 7.49 | Gum |
| 414 | (Z)-CH₂ON:CH | H | H | H | H | H | 7.46 | Gum |
| 415 | (CH₂)₃O | H | H | H | H | H | 7.48 | Oil |
| 416 | (CH₂)₄O | H | H | H | H | H | 7.47 | Oil |
| 417 | (CH₂)₅O | H | H | H | H | H | 7.48 | Oil |
| 418 | (E)-N:N | 4-OH | H | H | H | H | 7.50 | Oil |
| 419 | (E)-N:N | 4-CH₃O | H | H | H | H | 7.49 | Gum |
| 420 | CO.NH | 2-Br | H | H | H | H | 7.49 | Foam |
| 421 | CO.NH | 3-Br | H | H | H | H | 7.47 | Foam |
| 422 | CO.NH | 3-CH₃O | H | H | H | H | 7.48 | Foam |
| 423 | OCH₂CH₂O | H | H | H | H | H | 7.45 | Gum |
| 424 | SO₂O | ⊕ | ⊕ | H | H | H | 7.29 | Gum |
| 425 | SCH₂O | H | H | H | H | H | 7.47 | Oil |
| 426 | CH₂O | 2-(CH₃O₂C—C=CH.OCH₃) | H | H | H | H | 7.40 or 7.52 | Gum |
| 427 | SO₂O | 4-CF₃ | H | H | H | H | obscured | Gum |
| 428 | SO₂O | 2-CH₃O₂C | H | H | H | H | 7.41 | Gum |
| 429 | CH₂CH₂CH(OH) | H | H | H | H | H | | |
| 430 | (E)-CH₂CH=CH | H | H | H | H | H | | |
| 431 | C(CH₃)(OH) | H | H | H | H | H | | |
| 432 | CH(OH) | 2-Cl | H | H | H | H | | |
| 433 | CH(OH) | 4-Cl | H | H | H | H | | |
| 434 | CH(OH) | 2-CH₃O | H | H | H | H | | |
| 435 | CH(OH) | 3-CF₃ | H | H | H | H | | |
| 436 | CH(OH) | 3-CN | H | H | H | H | | |
| 437 | CH(OH) | 4-NO₂ | H | H | H | H | | |
| 438 | CH₂OSO₂ | H | H | H | H | H | | |
| 439 | CH₂NHCO.NH | H | H | H | H | H | | |
| 440 | CH₂NH | H | H | H | H | H | | |
| 441 | OCO.NH | H | H | H | H | H | | |
| 442 | NHCO.NH | H | H | H | H | H | | |
| 443 | CH₂OCO.NH | H | H | H | H | H | 7.47 | Gum |
| 444 | SO₂NH | 4-Br | H | H | H | H | | |
| 445 | CH₂NH | 3-CH₃ | H | H | H | H | | |

TABLE I - FOOTNOTES:
⁺Chemical shift of singlet from olefinic proton on beta-methoxypropenoate group (p.p.m from tetramethylsilane).
Solvent: CDCl₃ unless otherwise stated.
Substituents D and G join to form a fused ring. Thus compound numbers 168, 169, 247, 248, 332 and 333 are:

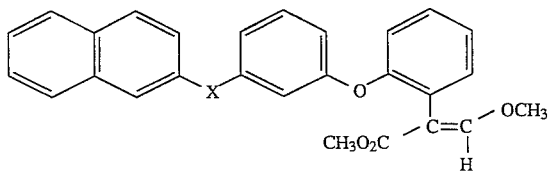

| X | COMPOUND NO |
|---|---|
| O | 168 |
| CH₂O | 247 |
| SO₂O | 332 |

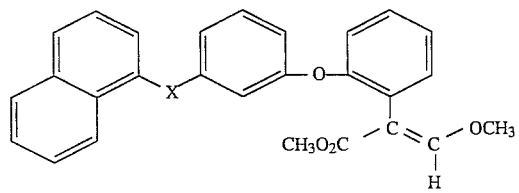

| X | COMPOUND NO |
|---|---|
| O | 169 |
| CH₂O | 248 |
| SO₂O | 333 |

And Compound No. 424 is:

TABLE I-continued

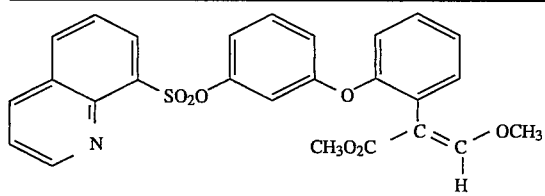

*, ⊕ Indicate, in each case, that structural assignment may be reversed. Thus the characterising data attributed to Compound No. 180 may, in fact, be that for Compound No. 367 and vice versa. The same applies to Compound Nos. 365 and 366.
≠ (E):(Z) ratio = 85:15 (see Example 20).
Ph is phenyl.

TABLE II

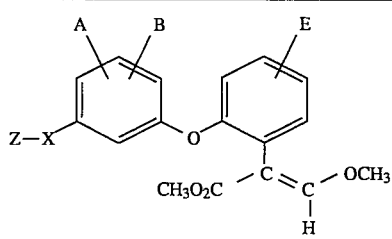

| Compound No. | Z | X | A | B | E | Olefinic[+] | Melting Point (°C.) |
|---|---|---|---|---|---|---|---|
| 1 | Pyridin-2-yl | O | H | H | H | 7.48 | Gum |
| 2 | Pyridin-2-yl | S | H | H | H | | |
| 3 | Pyridin-2-yl | N(CH₃) | H | H | H | | |
| 4 | Pyridin-2-yl | SO₂O | H | H | H | | |
| 5 | Pyridin-2-yl | CH₂CH₂ | H | H | H | | |
| 6 | Pyridin-2-yl | OCH₂ | H | H | H | 7.48 | Gum |
| 7 | Pyridin-2-yl | CH₂O | H | H | H | | |
| 8 | Pyridin-3-yl | O | H | H | H | 7.48 | Gum |
| 9 | Pyridin-3-yl | S | H | H | H | | |
| 10 | Pyridin-3-yl | N(CH₃) | H | H | H | | |
| 11 | Pyridin-3-yl | SO₂O | H | H | H | | |
| 12 | Pyridin-3-yl | CH₂CH₂ | H | H | H | | |
| 13 | Pyridin-3-yl | OCH₂ | H | H | H | | |
| 14 | Pyridin-3-yl | CH₂O | H | H | H | | |
| 15 | Pyridin-4-yl | O | H | H | H | 7.48 | Gum |
| 16 | Pyridin-4-yl | S | H | H | H | | |
| 17 | Pyridin-4-yl | N(CH₃) | H | H | H | | |
| 18 | Pyridin-4-yl | SO₂O | H | H | H | | |
| 19 | Pyridin-4-yl | CH₂CH₂ | H | H | H | | |
| 20 | Pyridin-4-yl | OCH₂ | H | H | H | | |
| 21 | PYridin-4-yl | CH₂O | H | H | H | | |
| 22 | Pyrimidin-2-yl | O | H | H | H | 7.38 | Gum |
| 23 | Pyrimidin-2-yl | S | H | H | H | 7.49 | Gum |
| 24 | Pyrimidin-4-yl | N(CH₃) | H | H | H | | |
| 25 | Pyrimidin-4-yl | SO₂O | H | H | H | | |
| 26 | Pyrimidin-5-yl | CH₂CH₂ | H | H | H | | |
| 27 | Pyrimidin-5-yl | CH₂O | H | H | H | | |
| 28 | 1,2,4-Triazin-3-yl | OCH₂ | H | H | H | | |
| 29 | 1,3,5-Triazin-2-yl | O | H | H | H | | |
| 30 | Pyrazin-2-yl | O | H | H | H | 7.49 | Gum |
| 31 | Pyrazin-2-yl | S | H | H | H | | |
| 32 | Pyrazin-2-yl | N(CH₃) | H | H | H | | |
| 33 | Pyrazin-2-yl | SO₂O | H | H | H | | |
| 34 | Pyrazin-2-yl | CH₂O | H | H | H | | |
| 35 | Pyridazin-3-yl | O | H | H | H | 7.49 | Gum |
| 36 | Pyridazin-3-yl | S | H | H | H | | |
| 37 | Pyridazin-3-yl | SO₂O | H | H | H | | |
| 38 | Quniolin-2-yl | O | H | H | H | 7.43 | 109–110 |
| 39 | Quinolin-2-yl | CH₂O | H | H | H | | |
| 40 | Quinolin-3-yl | O | H | H | H | | |
| 41 | Quinolin-3-yl | SO₂O | H | H | H | | |
| 42 | Benzoxazol-2-yl | O | H | H | H | | |
| 43 | Benzoxazol-2-yl | S | H | H | H | | |
| 44 | Benzoxazol-2-yl | N(CH₃) | H | H | H | | |
| 45 | Benzoxazol-2-yl | SO₂O | H | H | H | | |
| 46 | Benzthiazol-2-yl | CH₂CH₂ | H | H | H | | |

TABLE II-continued

| Compound No. | Z | X | A | B | E | Olefinic+ | Melting Point (°C.) |
|---|---|---|---|---|---|---|---|
| 47 | Benzthiazol-2-yl | OCH₂ | H | H | H | 7.49 | Gum |
| 48 | Benzthiazol-2-yl | CH₂O | H | H | H | | |
| 49 | Thien-2-yl | CH₂O | H | H | H | | |
| 50 | Thien-2-yl | CH₂CH₂ | H | H | H | | |
| 51 | Thien-3-yl | O | H | H | H | | |
| 52 | Thien-2-yl | SO₂O | H | H | H | 7.40 | Gum |
| 53 | 5-CF₃-Pyridin-2-yl | O | H | H | H | 7.49 | Oil |
| 54 | 5-CF₃-Pyridin-2-yl | S | H | H | H | | |
| 55 | 5-CF₃-Pyridin-2-yl | CH₂O | H | H | H | | |
| 56 | 3-F-Pyridin-2-yl | O | H | H | H | | |
| 57 | 3-Cl-Pyridin-2-yl | O | H | H | H | | |
| 58 | 4-Br-Pyridin-2-yl | O | H | H | H | | |
| 59 | 5-CH₃-Pyridin-2-yl | O | H | H | H | | |
| 60 | 6-CH₃O-Pyridin-2-yl | O | H | H | H | | |
| 61 | 2-F-Pyridin-3-yl | O | H | H | H | | |
| 62 | 3-CF₃-Pyridin-4-yl | O | H | H | H | | |
| 63 | 4,6-di-F-Pyridin-2-yl | O | H | H | H | | |
| 64 | 3-NO₂-5-CF₃-Pyridin-2-yl | O | H | H | H | | |
| 65 | 5-(CH₃O₂C)-Pyridin-2-yl | O | H | H | H | | |
| 66 | 3-CH₃-Pyridin-2-yl | O | H | H | H | | |
| 67 | 4-CH₃-Pyridin-2-yl | O | H | H | H | | |
| 68 | 6-CH₃-Pyridin-2-yl | O | H | H | H | | |
| 69 | 5-(CN)-Pyridin-2-yl | O | H | H | H | 7.49 | Gum |
| 70 | 3-Cl-5-(C₆H₅O)-1,3,5-triazin-2-yl | O | H | H | H | | |
| 71 | Pyridin-2-yl | O | 2-F | H | H | | |
| 72 | Pyridin-2-yl | O | 4-Cl | H | H | | |
| 73 | Pyridin-4-yl | O | 5-CH₃ | H | H | | |
| 74 | Pyridin-4-yl | O | 4-CH₃O | H | H | | |
| 75 | 5-CF₃-Pyridin-2-yl | O | 5-CN | H | H | | |
| 76 | 5-CF₃-Pyridin-2-yl | O | 4-F | 5-CH₃O | H | | |
| 77 | Pyrimidin-2-yl | O | H | H | 5-Cl | | |
| 78 | Pyrimidin-2-yl | O | H | H | 6-F | | |
| 79 | Benzoxaxol-2-yl | O | 4-CF₃O | H | 5-F | | |
| 80 | Benzoxazol-2-yl | O | 5-NO₂ | H | H | | |
| 81 | 1,2,4-Traizol-1-yl | CH₂ | H | H | H | 7.48 | Gum |
| 82 | 1,2,3-Triazol-1-yl | CH₂ | H | H | H | | |
| 83 | Benzthiazol-2-yl | O | H | H | H | 7.38 | Gum |
| 84 | 3-Chloroquinoxalin-2-yl | O | H | H | H | 7.50 | 117–119 |
| 85 | Pyrimidin-2-yl | OCH₂ | H | H | H | 7.49 | Oil |
| 86 | 3,5-di-Cl-1,3,5-triazin-2-yl | O | H | H | H | 7.52 | Gum |
| 87 | Pyrimidin-5-yl | O | H | H | H | 7.47 | Oil |
| 88 | 3-Cl,5-(CH₃O)-1,3,5-triazin-2-yl | O | H | H | H | 7.50 | Gum |
| 89 | 6-Cl-Pyrimidin-4-yl | O | H | H | H | 7.49 | Oil |
| 90 | 5-Br-Pyrimidin-2-yl | O | H | H | H | 7.48 | Gum |
| 91 | 5-Cl-Pyrimidin-2-yl | O | H | H | H | 7.48 | Oil |
| 92 | Pyrimidin-4-yl | O | H | H | H | 7.48 | Oil |
| 93 | 2,6-Di-CH₃O-Pyrimidin-4-yl | O | H | H | H | 7.48 | Oil |
| 94 | 2-Cl-6-CH₃-Pyrimidin-4-yl | O | H | H | H | 7.50 | 113–118 |
| 95 | 2,6-Di-Cl-Pyrimidin-4-yl | O | H | H | H | 7.50 | 113–115 |
| 96 | 2,5,6-Tri-Cl-Pyrimidin-4-yl | O | H | H | H | 7.49 | Gum |
| 97 | 2-Cl-Pyrimidin-4-yl | O | H | H | H | * | Oil |
| 98 | 2-CH₃-Thiazol-4-yl | CH₂O | H | H | H | 7.48 | Oil |
| 99 | Benzoxazol-2-yl | OCH₂ | H | H | H | 7.50 | Gum |
| 100 | Pyrazin-2-yl | OCH₂ | H | H | H | 7.49 | Gum |
| 101 | 6-Cl-Pyrazin-2-yl | OCH₂ | H | H | H | 7.49 | Gum |

TABLE II-continued

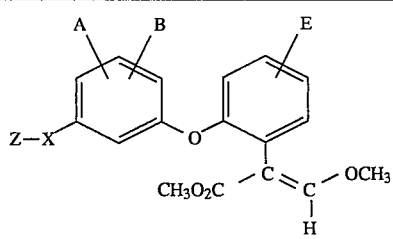

| Compound No. | Z | X | A | B | E | Olefinic+ | Melting Point (°C.) |
|---|---|---|---|---|---|---|---|
| 102 | Quinolin-2-yl | OCH$_2$ | H | H | H | 7.49 | Gum |
| 103 | 6-Cl-Pyridazin-3-yl | OCH$_2$ | H | H | H | 7.49 | Gum |
| 104 | Pyridin-4-yl, N-oxide | OCH$_2$ | H | H | H | 7.49 | Foam |
| 105 | 5-CF$_3$-Pyridin-2-yl | OCH$_2$ | H | H | H | 7.48 | Gum |
| 106 | 3-Cyanopyridin-2-yl | O | H | H | H | 7.48 | Gum |
| 107 | 5-NO$_2$-Pyridin-2-yl | O | H | H | H | 7.49 | Gum |
| 108 | Pyrimidin-2-yl | CH$_2$O | H | H | H | | |
| 109 | Pyrimidin-2-yl | SO$_2$O | H | H | H | | |
| 110 | Pyrimidin-2-yl | NH | H | H | H | | |
| 111 | Pyrimidin-2-yl | N(CH$_3$) | H | H | H | | |
| 112 | Pyrimidin-2-yl | CH$_2$ | H | H | H | | |
| 113 | Pyrimidin-2-yl | CH(OH) | H | H | H | | |
| 114 | Pyrimidin-2-yl | CH$_2$CH$_2$ | H | H | H | | |
| 115 | Pyrimidin-4-yl | O | H | H | H | | |
| 116 | Pyrimidin-4-yl | CH$_2$O | H | H | H | | |
| 117 | Pyrimidin-4-yl | OCH$_2$ | H | H | H | | |
| 118 | Pyrimidin-4-yl | NH | H | H | H | | |
| 119 | Pyrimidin-4-yl | S | H | H | H | | |
| 120 | Pyrimidin-4-yl | CH$_2$ | H | H | H | | |
| 121 | Pyrimidin-4-yl | CH(OH) | H | H | H | | |
| 122 | Pyrimidin-4-yl | CH$_2$CH$_2$ | H | H | H | | |
| 123 | Pyrimidin-5-yl | SO$_2$O | H | H | H | | |
| 124 | Pyrimidin-5-yl | OCH$_2$ | H | H | H | | |
| 125 | Pyrimidin-5-yl | NH | H | H | H | | |
| 126 | Pyrimidin-5-yl | N(CH$_3$) | H | H | H | | |
| 127 | Pyrimidin-5-yl | S | H | H | H | | |
| 128 | Pyrimidin-5-yl | CH$_2$ | H | H | H | | |
| 129 | Pyrimidin-5-yl | CH(OH) | H | H | H | | |
| 130 | 6-Chloropyridazin-3-yl | O | H | H | H | 7.50 | Gum |
| 131 | 6-Chloropyridazin-3-yl | CH$_2$O | H | H | H | | |
| 132 | 6-Chloropyridazin-3-yl | NH | H | H | H | | |
| 133 | 6-Chloropyridazin-3-yl | N(CH$_3$) | H | H | H | | |
| 134 | 6-Chloropyridazin-3-yl | CH(OH) | H | H | H | | |
| 135 | Pyridazin-4-yl | O | H | H | H | | |
| 136 | Pyridazin-4-yl | OCH$_2$ | H | H | H | | |
| 137 | Pyridazin-4-yl | NH | H | H | H | | |
| 138 | Pyridazin-4-yl | SO$_2$O | H | H | H | | |
| 139 | 1,3,5-Triazin-2-yl | NH | H | H | H | | |
| 140 | 1,3,5-Triazin-2-yl | N(CH$_3$) | H | H | H | | |
| 141 | 1,2,4-Triazin-3-yl | O | H | H | H | | |
| 142 | 1,2,4-Triazin-3-yl | NH | H | H | H | | |
| 143 | 1,2,4-Triazin-3-yl | N(CH$_3$) | H | H | H | | |
| 144 | 1,2,4-Triazin-5-yl | O | H | H | H | | |
| 145 | 1,2,4-Triazin-5-yl | NH | H | H | H | | |
| 146 | 1,2,4-Triazin-6-yl | O | H | H | H | | |
| 147 | 1,2,4-Triazin-6-yl | N(CH$_3$) | H | H | H | | |
| 148 | Pyrimin-2-yl, N-oxide | O | H | H | H | | |
| 149 | Pyrimidin-4-yl, 1-N-oxide | O | H | H | H | | |
| 150 | Pyrimidin-4-yl, 3-N-oxide | O | H | H | H | | |
| 151 | Pyridin-2-yl, N-oxide | O | H | H | H | | |
| 152 | Pyridin-3-yl, N-oxide | O | H | H | H | | |
| 153 | Pyrazin-2-yl, 1-N-oxide | O | H | H | H | | |
| 154 | Pyrazin-2-yl, 4-N-oxide | O | H | H | H | | |
| 155 | Pyridazin-3-yl, 1-N-oxide | O | H | H | H | | |
| 156 | Pyridazin-3-yl, 2-N- | O | H | H | H | | |

TABLE II-continued

| Compound No. | Z | X | A | B | E | Olefinic+ | Melting Point (°C.) |
|---|---|---|---|---|---|---|---|
| | oxide | | | | | | |
| 157 | Isoquinolin-1-yl | O | H | H | H | | |
| 158 | Isoquinolin-1-yl | NH | H | H | H | | |
| 159 | Isoquinolin-1-yl | CH$_2$O | H | H | H | | |
| 160 | Isoquinolin-1-yl | OCH$_2$ | H | H | H | | |
| 161 | Isoquinolin-1-yl | CH(OH) | H | H | H | | |
| 162 | Isoquinolin-1-yl | S | H | H | H | | |
| 163 | Isoquinolin-1-yl | SO$_2$O | H | H | H | | |
| 164 | Quinolin-4-yl | O | H | H | H | | |
| 165 | Quinolin-4-yl | NH | H | H | H | | |
| 166 | Quinolin-4-yl | CH$_2$O | H | H | H | | |
| 167 | Quinolin-4-yl | OCH$_2$ | H | H | H | | |
| 168 | Quinolin-4-yl | CH(OH) | H | H | H | | |
| 169 | Quinolin-4-yl | S | H | H | H | | |
| 170 | Quinolin-4-yl | SO$_2$O | H | H | H | | |
| 171 | Quinazolin-4-yl | O | H | H | H | | |
| 172 | Quinazolin-4-yl | NH | H | H | H | | |
| 173 | Quinazolin-4-yl | CH$_2$O | H | H | H | | |
| 174 | Quinazolin-4-yl | OCH$_2$ | H | H | H | | |
| 175 | Quinazolin-4-yl | CH(OH) | H | H | H | | |
| 176 | Quinazolin-4-yl | S | H | H | H | | |
| 177 | Quinazolin-4-yl | SO$_2$O | H | H | H | | |
| 178 | 7-Chloroquinolin-4-yl | O | H | H | H | | |
| 179 | 7-Chloroquinolin-4-yl | S | H | H | H | | |
| 180 | 7-Chloroquinolin-4-yl | NH | H | H | H | | |
| 181 | Purin-6-yl | O | H | H | H | | |
| 182 | 2-Chloropurin-6-yl | S | H | H | H | | |
| 183 | 2-Chloropurin-6-yl | NH | H | H | H | | |
| 184 | 5-NO$_2$-Thien-2-yl | OCH$_2$ | H | H | H | | |
| 185 | 5-NO$_2$-Thien-2-yl | O | H | H | H | | |
| 186 | Thiazol-2-yl | CH$_2$O | H | H | H | | |
| 187 | Thiazol-2-yl | O | H | H | H | | |
| 188 | Thiazol-2-yl | NH | H | H | H | | |
| 189 | Thiazol-4-yl | CH$_2$O | H | H | H | | |
| 190 | Thiazol-4-yl | O | H | H | H | | |
| 191 | Thiazol-4-yl | NH | H | H | H | | |
| 192 | Thiazol-5-yl | CH$_2$O | H | H | H | | |
| 193 | Thiazol-5-yl | O | H | H | H | | |
| 194 | Thiazol-5-yl | NH | H | H | H | | |
| 195 | Oxazol-2-yl | CH$_2$O | H | H | H | | |
| 196 | Oxazol-4-yl | O | H | H | H | | |
| 197 | Oxazol-5-yl | NH | H | H | H | | |
| 198 | 5-CF$_3$-1,3,4-Thiadiazol-2-yl | O | H | H | H | | |
| 199 | 5-CF$_3$-1,3,4-Thiadiazol-2-yl | OCH$_2$ | H | H | H | | |
| 200 | 4-Cl-1,2,5-Thiadiazol-3-yl | O | H | H | H | | |
| 201 | (thienopyrazine structure) | O | H | H | H | 7.49 | 115–116 |
| 202 | (thienopyrazine structure) | NH | H | H | H | | |

TABLE II-continued

Structure: Z—X—[benzene ring with A, B]—O—[benzene ring with E]—C(CO₂CH₃)=C(OCH₃)H

| Compound No. | Z | X | A | B | E | Olefinic⁺ | Melting Point (°C.) |
|---|---|---|---|---|---|---|---|
| 203 | (thieno-pyrimidine structure) | N(CH₃) | H | H | H | | |
| 204 | 4-Cl-Pyrimidin-2-yl | O | H | H | H | | |
| 205 | 4-Br-Pyrimidin-2-yl | O | H | H | H | | |
| 206 | 4-F-Pyrimidin-2-yl | O | H | H | H | | |
| 207 | 4-CH₃-Pyrimidin-2-yl | O | H | H | H | | |
| 208 | 4-CH₃O-Pyrimidin-2-yl | O | H | H | H | | |
| 209 | 4-CH₃CH₂O-Pyrimidin-2-yl | O | H | H | H | | |
| 210 | 4-NO₂-Pyrimidin-2-yl | O | H | H | H | | |
| 211 | 4-Cyano-Pyrimidin-2-yl | O | H | H | H | | |
| 212 | 4-CF₃-Pyrimidin-2-yl | O | H | H | H | | |
| 213 | 4-C₆H₅-Pyrimidin-2-yl | O | H | H | H | | |
| 214 | 4-C₆H₅O-Pyrimidin-2-yl | O | H | H | H | | |
| 215 | 5-F-Pyrimidin-2-yl | O | H | H | H | | |
| 216 | 5-CH₃-Pyrimidin-2-yl | O | H | H | H | | |
| 217 | 5-CH₃O-Pyrimidin-2-yl | O | H | H | H | | |
| 218 | 5-CH₃CH₂O-Pyrimidin-2-yl | O | H | H | H | | |
| 219 | 5-NO₂-Pyrimidin-2-yl | O | H | H | H | | |
| 220 | 5-Cyano-Pyrimidin-2-yl | O | H | H | H | | |
| 221 | 5-CF₃-Pyrimidin-2-yl | O | H | H | H | | |
| 222 | 5-C₆H₅-Pyrimidin-2-yl | O | H | H | H | | |
| 223 | 5-C₆H₅O-Pyrimidin-2-yl | O | H | H | H | | |
| 224 | 4,5-Di-Cl-Pyrimidin-2-yl | O | H | H | H | | |
| 225 | 4,6-Di-Cl-Pyrimidin-2-yl | O | H | H | H | | |
| 226 | 4-Cl-6-CH₃-Pyrimidin-2-yl | O | H | H | H | | |
| 227 | 4-Cl-5-CH₃O-Pyrimidin-2-yl | O | H | H | H | | |
| 228 | 2-F-Pyrimidin-4-yl | O | H | H | H | | |
| 229 | 2-Br-Pyrimidin-4-yl | O | H | H | H | | |
| 230 | 2-CH₃-Pyrimidin-4-yl | O | H | H | H | | |
| 231 | 2-CH₃O-Pyrimidin-4-yl | O | H | H | H | | |
| 232 | 2-CH₃CH₂O-Pyrimidin-4-yl | O | H | H | H | | |
| 233 | 2-NO₂-Pyrimidin-4-yl | O | H | H | H | | |
| 234 | 2-CH₃S-Pyrimidin-4-yl | O | H | H | H | | |
| 235 | 2-Cyano-Pyrimidin-4-yl | O | H | H | H | | |
| 236 | 2-CF₃-Pyrimidin-4-yl | O | H | H | H | | |
| 237 | 2-C₆H₅O-Pyrimidin-4-yl | O | H | H | H | | |
| 238 | 2-C₆H₅-Pyrimidin-4-yl | O | H | H | H | | |
| 239 | 6-F-Pyrimidin-4-yl | O | H | H | H | | |
| 240 | 6-Br-Pyrimidin-4-yl | O | H | H | H | | |
| 241 | 6-CH₃-Pyrimidin-4-yl | O | H | H | H | | |
| 242 | 6-CH₃O-Pyrimidin-4-yl | O | H | H | H | | |
| 243 | 6-CH₃CH₂O-Pyrimidin-4-yl | O | H | H | H | | |
| 244 | 6-NO₂-Pyrimidin-4-yl | O | H | H | H | | |
| 245 | 6-Cyano-Pyrimidin-4-yl | O | H | H | H | | |
| 246 | 6-CF₃-Pyrimidin-4-yl | O | H | H | H | | |
| 247 | 6-C₆H₅O-Pyrimidin-4-yl | O | H | H | H | | |
| 248 | 6-C₆H₅-Pyrimidin-4-yl | O | H | H | H | | |
| 249 | 5-F-Pyrimidin-4-yl | O | H | H | H | | |
| 250 | 5-Cl-Pyrimidin-4-yl | O | H | H | H | | |
| 251 | 5-Br-Pyrimidin-4-yl | O | H | H | H | | |
| 252 | 5-CH₃-Pyrimidin-4-yl | O | H | H | H | | |
| 253 | 5-CH₃O-Pyrimidin-4-yl | O | H | H | H | | |
| 254 | 5-CH₃CH₂O-Pyrimidin- | O | H | H | H | | |

TABLE II-continued

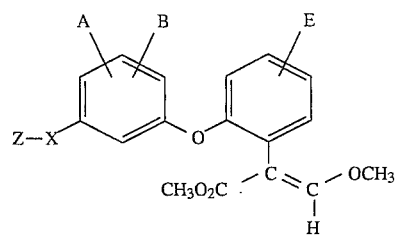

| Compound No. | Z | X | A | B | E | Olefinic+ | Melting Point (°C.) |
|---|---|---|---|---|---|---|---|
| | 4-yl | | | | | | |
| 255 | 5-NO$_2$-Pyrimidin-4-yl | O | H | H | H | | |
| 256 | 5-Cyano-Pyrimidin-4-yl | O | H | H | H | | |
| 257 | 5-CF$_3$-Pyrimidin-4-yl | O | H | H | H | | |
| 258 | 5-C$_6$H$_5$O-Pyrimidin-4-yl | O | H | H | H | | |
| 259 | 5-C$_6$H$_5$-Pyrimidin-4-yl | O | H | H | H | | |
| 260 | 2-Cl-Pyrimidin-5-yl | O | H | H | H | | |
| 261 | 2-CH$_3$-Pyrimidin-5-yl | O | H | H | H | | |
| 262 | 2-F-Pyrimidin-5-yl | O | H | H | H | | |
| 263 | 2-CH$_3$O-Pyrimidin-5-yl | O | H | H | H | | |
| 264 | 2-Cyano-Pyrimidin-5-yl | O | H | H | H | | |
| 265 | 4-CH$_3$-Pyrimidin-5-yl | O | H | H | H | | |
| 266 | 4-CH$_3$O-Pyrimidin-5-yl | O | H | H | H | | |
| 267 | 4-CF$_3$-Pyrimidin-5-yl | O | H | H | H | | |
| 268 | 2,4-di-CH$_3$-Pyrimidin-5-yl | O | H | H | H | | |
| 269 | 2-CH$_3$S-4-CH$_3$O-Pyrimidin-5-yl | O | H | H | H | | |
| 270 | Pyrrol-2-yl | CONH | H | H | H | 7.48 | Foam |
| 271 | 6-Cl-3-NO$_2$-Pyridin-2-yl and 6-Cl-5-NO$_2$-Pyridin-2-yl, 1:1 mixture | O | H | H | H | 7.50 | Gum |
| 272 | 3,6-Di-CH$_3$-Pyrazin-2-yl | O | H | H | H | 7.49 | Gum |
| 273 | 6-Cl-Pyrazin-2-yl | O | H | H | H | 7.50 | Gum |
| 274 | 6-CH$_3$O-Pyridazin-3-yl | O | H | H | H | 7.50 | Gum |
| 275 | 6-Cl-4-CH$_3$-Pyridazin-3-yl | O | H | H | H | | |
| 276 | 6-Cl-5-CH$_3$-Pyridazin-3-yl | O | H | H | H | | |
| 277 | 4-CF$_3$-Pyridin-2-yl | O | H | H | H | | |
| 278 | 6-Cyanopyridin-2-yl | O | H | H | H | | |
| 279 | 4-Cyanopyridin-2-yl | O | H | H | H | | |
| 280 | 3-(CH$_3$O$_2$C)Pyrin-2-yl | O | H | H | H | | |
| 281 | 6-C$_6$H$_5$-Pyridazin-3-yl | O | H | H | H | | |
| 282 | 2-(CH$_3$O$_2$C)-Pyridin-2-yl | O | H | H | H | | |
| 283 | 5-(CH$_3$O$_2$C)-Pyridin-3-yl | O | H | H | H | | |
| 284 | 4-CF$_2$Cl-Pyridin-2-yl | O | H | H | H | | |
| 285 | 3,5-Di-CF$_3$-Pyridin-2-yl | O | H | H | H | | |
| 286 | 6-CF$_3$-Pyridin-2-yl | O | H | H | H | | |
| 287 | 5-CF$_3$-Pyridin-3-yl | O | H | H | H | | |
| 288 | 2-Cl-Pyridin-3-yl | O | H | H | H | | |
| 289 | 2-CH$_3$O-Pyridin-3-yl | O | H | H | H | | |
| 290 | 2-Cl-Pyridin-4-yl | O | H | H | H | | |
| 291 | 2-CH$_3$O-Pyridin-4-yl | O | H | H | H | | |
| 292 | 2-Cl-Pyridin-5-yl | O | H | H | H | | |
| 293 | 2-CH$_3$O-Pyridin-5-yl | O | H | H | H | | |
| 294 | 3-CH$_3$S-Pyridin-2-yl | O | H | H | H | | |
| 295 | 4-CF$_3$O-Pyridin-2-yl | O | H | H | H | | |
| 296 | 4-CON(CH$_3$)$_2$-Pyridin-2-yl | O | H | H | H | | |
| 297 | 3-Cl-1,2,4-Oxadiazol-5-yl | O | H | H | H | | |
| 298 | 3-Cl-1,2,4-Oxadiazol-5-yl | S | H | H | H | | |
| 299 | 5-CH$_3$S-1,2,4-Oxadiazol-3-yl | O | H | H | H | | |
| 300 | Pyridin-2-yl | CH(OH) | H | H | H | | |
| 301 | Pyridin-3-yl | CH(OH) | H | H | H | | |
| 302 | Pyridin-4-yl | CH(OH) | H | H | H | | |

TABLE II-continued

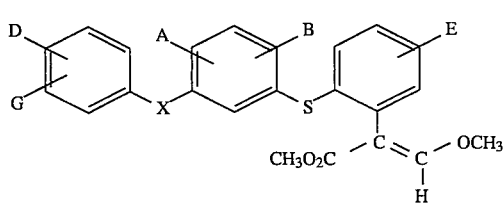

| Compound No. | Z | X | A | B | E | Olefinic[+] | Melting Point (°C.) |
|---|---|---|---|---|---|---|---|
| 303 | Pyridin-2-yl | CO | H | H | H | | |
| 304 | Pyridin-3-yl | CO | H | H | H | | |
| 305 | Pyridin-4-yl | CO | H | H | H | | |
| 306 | Thien-2-yl | CH(OH) | H | H | H | | |
| 307 | Furan-2-yl | CH(OH) | H | H | H | | |
| 308 | N-$CH_3$-Pyrrol-2-yl | CH(OH) | H | H | H | | |
| 309 | N-$CH_3$-Pyrrol-2-yl | CO | H | H | H | | |
| 310 | 6-Br-Pyridin-2-yl | $OCH_2$ | H | H | H | 7.49 | Oil |
| 311 | 4-Cl-Pyrimidin-2-yl and 2-Cl-Pyrimidin-4-yl (3:1 mixture, not necessarily respectively) | $OCH_2$ | H | H | H | 7.49 | Oil |
| 312 | 2,6-Di-F-Pyrimidin-4-yl | O | H | H | H | | |
| 313 | 2-$CH_3$S-6-$CH_3$-Pyrimidin-4-yl | O | H | H | H | 7.48 | Gum |
| 314 | 2-$CH_3$S-Pyrimidin-4-yl | O | H | H | H | | |
| 315 | N-$CH_3$-Pyrrol-2-yl | CON($CH_3$) | H | H | H | 7.47 | Gum |
| 316 | 5-$CF_3$-Pyridin-2-yl | NH | H | H | H | | |
| 317 | 2-Cl-Pyrimidin-4-yl | NH | H | H | H | | |
| 318 | 4-Cl-Pyrimidin-2-yl | NH | H | H | H | | |
| 319 | 5-$NO_2$-6-($CH_3$)$_2$N-Pyridin-2-yl | O | H | H | H | 7.48 | Gum |
| 320 | 6-Cl-4-$CH_3$-Pyridazin-3-yl and 6-Cl-5-$CH_3$-Pyridazin-3-yl (3:2 mixture, not necessarily respectively) | O | H | H | H | 7.50 | Gum |

FOOTNOTES:
[+]Chemical shift of singlet from olefinic proton on beta-methoxypropenoate group (p.p.m form tetramethylsilane).
Solvent: $CDCl_3$ unless otherwise stated.
*See Table V for carbon-13 n.m.r. data.

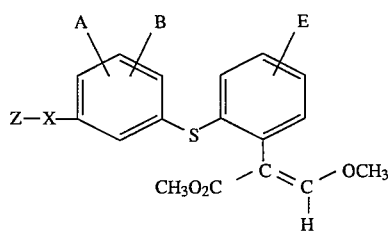

Table III comprises 446 compounds of the general structure above. The first 445 of these have all the values of X, D, G, A, B and E listed in Table I. That is, Compound Nos. 1 to 445 of Table III are the same as those of Table I except that the value of K is oxygen in Table I and sulphur in Table III. Compound No. 446 has the above structure wherein X is oxygen and A, B, D, E and G are all hydrogen. A description of the preparation of Compound No. 446 is given in Example 11.

TABLE III

| Compound No. | X | D | G | A | B | E | Olefinic[+] | Melting Point (°C.) |
|---|---|---|---|---|---|---|---|---|
| 23 | $CH_2O$ | H | H | H | H | H | 7.49 | Gum |

TABLE III-continued

| Compound No. | X | D | G | A | B | E | Olefinic[+] | Melting Point (°C.) |
|---|---|---|---|---|---|---|---|---|
| 51 | $SO_2O$ | H | H | H | H | H | 7.46 | Gum |
| 131 | O | 2-$NO_2$ | H | H | H | H | 7.48 | Gum |
| 212 | $CH_2O$ | 4-$NO_2$ | H | H | H | H | 7.49 | Gum |
| 446 | O | H | H | H | H | H | 7.48 | 48–51.5 |

Table IV comprises 320 compounds of the general structure above with all the values of Z, X, A, B and E listed in Table II. That is, compounds Nos. 1 to 320 of Table IV are the same as those of Table II except that the value of K is oxygen in Table II and sulphur in Table IV.

| Compound No. | Z | x | A | B | E | Olefinic+ | Melting Point (°C.) |
|---|---|---|---|---|---|---|---|
| 22 | Pyrimidin-2-yl | O | H | H | H | 7.49 | Gum |
| 87 | Pyrimidin-5-yl | O | H | H | H | 7.48 | Gum |

TABLE V: SELECTED PROTON NMR DATA

Table V shows selected proton n.m.r data for certain compounds described in Tables I, II, III and IV. Chemical shifts are measured in p.p.m from tetramethylsilane, and deuterochloroform was used as solvent throughout. The column headed 'frequency' refers to the operating frequency of the n.m.r spectrometer. The following abbreviations are used:

br=broad
s=singlet
d=doublet
t=triplet
q=quartet
m=multiplet

| TABLE NO. | COMPOUND NO. | FREQUENCY (MHz) | |
|---|---|---|---|
| I | 2 | 60 | 3.36(3H, s), 3.46(3H, s), 6.6–7.6(14H, m) ppm. |
| I | 7 | 60 | 1.98(3H, s), 3.48(3H, s), 3.59(3H, s), 6.6–7.3(13H, m), 7.39(1H, s) ppm. |
| I | 15 | 270 | 2.88(4H, s), 3.60(3H, s), 3.77(3H, s), 6.76–3.93 (4H, m), 7.07–7.33(9H, m), 7.49(1H, s) ppm. |
| I | 25 | 270 | 3.59(3H, s), 3.74(3H, s), 4.05(2H, s), 6.80–7.32 (13H, m), 7.47(1H, s) ppm. |
| I | 27 | 270 | 3.60(3H, s), 3.77(3H, s), 3.98(2H, q), 6.60–6.90 (4H, m), 7.10–7.30(4H, m), 7.39–7.50(5H, m), 7.48 (1H, s) ppm. |
| I | 29 | 400 | 3.59(3H, s), 3.77(3H, s), 4.26(2H, s), 6.70–6.90 (4H, m), 7.10–7.30(5H, m), 7.45–7.52(1H, m), 7.48 (1H, s), 7.60–7.70(3H, m) ppm. |
| I | 38 | 270 | 2.99(3H, s), 3.56(3H, s), 3.69(3H, s), 4.46(2H, s), 6.65–6.73(3H, t), 6.79 (1H, d), 6.85–6.95(3H, t), 7.10(1H, t), 7.16–7.29 (5H, m), 7.44(1H, s) ppm. |
| I | 62 | 270 | 3.61(3H, s), 3.78(3H, s), 6.7–7.6(11H, m), 7.46(1H, s), 7.8(3H, m) ppm. |
| I | 67 | 270 | 3.59(3H, s), 3.79(3H, s), 7.02–7.40(10H, m), 7.40 (1H, s), 7.70(2H, d), 8.32 (1H, s) ppm. |
| I | 84 | 270 | 3.60(3H, s), 3.75(3H, s), 6.97(1H, d), 7.14–7.53 (11H, m), 7.50(1H, s), 7.59(1H, d), 7.70(1H, d) ppm. |
| I | 86 | 400 | 3.60(3H, s), 3.74(3H, s) 6.99(1H, d), 7.09(1H, d), 7.12–7.41(9H, m), 7.49 (1H, s), 7.50(1H, s), 7.59 (1H, d), 8.38(1H, s) ppm. |
| I | 96 | 400 | 3.07(2H, t), 3.60(3H, s), 3.75(3H, s), 4.10(2H, t), 6.5–7.4(13H, m), 7.48 (1H, s) ppm. |
| I | 115 | 270 | 3.60(3H, s), 3.75(3H, s), 4.63(2H, d), 6.3–7.4(15H, m), 7.47(1H, s) ppm. |
| I | 119 | 270 | 3.60(3H, s), 3.76(3H, s), 6.58–6.72(3H, m), 6.96–7.32(8H, m), 7.41–7.50 (1H, m), 7.48(1H, s) ppm. |
| I | 120 | 270 | 3.60(3H, s), 3.76(3H, s), 6.62–7.36(12H, m), 7.48 (1H, s) ppm. |
| I | 122 | 90 | 3.61(3H, s), 3.77(3H, s), 6.5–6.8(3H, m), 6.9–7.4 (9H, m), 7.50(1H, s) ppm. |
| I | 123 | 90 | 3.64(3H, s), 3.79(3H, s), 6.6–6.9(2H, m), 6.9–7.5 (10H, m), 7.51(1H, s) ppm. |
| I | 125 | 90 | 2.23(3H, s), 3.61(3H, s), 3.77(3H, s), 6.5–6.8(3H, m), 6.8(3H, m), 6.8–7.5(9H,m), 7.51(1H, s) ppm. |
| I | 126 | 400 | 2.33(3H, s), 3.61(3H, s), 3.76(3H, s), 6.62–7.3 (12H, m), 7.49(1H, s) ppm. |
| I | 127 | 90 | 2.32(3H, s), 3.60(3H, s), 3.75(3H, s), 6.62–7.40 (12H, m), 7.49(1H, s) ppm. |
| I | 128 | 270 | 3.58(3H, s), 3.74(3H, s), 3.82(3H, s), 6.56–6.65 (3H, m), 6.84–7.00(4H, m), 7.06–7.28(5H, m), 7.46 (1H, s) ppm. |
| I | 130 | 60 | 3.6(3H, s), 3.75(3H, s), 3.8(3H, s), 6.57–7.3(12H, m), 7.48(1H, s) ppm. |
| I | 131 | 270 | 3.61(3H, s), 3.76(3H, s), 6.62–6.79(3H, m), 6.97–7.34(7H, m), 7.47(1H, s), 7.48–7.56(1H, m), 7.94 (1H, d) ppm. |
| I | 135 | 90 | 3.62(3H, s), 3.78(3H, s), 6.6–6.9(3H, m), 6.9–7.6 (9H, m), 7.51(1H, s) ppm. |
| I | 138 | 270 | 3.60(3H, s), 3.76(3H, s), 6.62–6.76(3H, m), 6.90–7.02(2H, m), 7.12–7.38 (7H, m), 7.48(1H, s) ppm. |
| I | 141 | 250 | 3.59(3H, s), 3.70(3H, s), 6.6–6.8(3H, m), 6.9–7.1 (1H, m), 7.1–7.5(8H, m), 7.49(1H, s) ppm. |
| I | 143 | 90 | 3.56(3H, s), 3.68(3H, s), 6.54–7.36(17H, m), 7.46 (1H, s) ppm. |
| I | 144 | 400 | 3.60(3H, s), 3.75(3H, s), 6.65–6.76(5H, m), 6.97(1H, d), 7.02(2H, d), 7.10–7.38 (9H, m), 7.48(1H, s). |
| I | 145 | 90 | 3.62(3H, s), 3.77(3H, s), 6.64–7.49(17H, m), 7.50 (1H, s) ppm. |
| I | 150 | 90 | 3.59(3H, s), 3.74(3H, s), 6.6–6.9(3H, m), 6.9–7.7 (14H, m), 7.50(1H, s) ppm. |
| I | 157 | 90 | 3.64(3H, s), 3.79(3H, s), 6.6–7.5(11H, m), 7.53 (1H, s) ppm. |
| I | 171 | 90 | 3.61(3H, s), 3.76(3H, s), 6.6–6.8(2H, m), 6.8–7.5 |

| TABLE NO. | COMPOUND NO. | FREQUENCY (MHz) | |
|---|---|---|---|
| I | 175 | 90 | (10H, m), 7.51(1H, s) ppm. 3.57(3H, s), 3.73(3H, s), 6.50(1H, t), 6.58(2H, d), 6.9–7.4(9H, m), 7.41(1H, s) ppm. |
| I | 177 | 90 | 2.25(3H, s), 3.60(3H, s), 3.76(3H, s), 6.4–6.6(3H, m), 6.9–7.4(9H, m), 7.47 (1H, s) ppm. |
| I | 179 | 90 | 3.57(3H, s), 3.68(3H, s), 3.72(3H, s), 6.20(3H, m), 6.8–7.4(9H, m), 7.42(1H, s) ppm. |
| I | 180 | 250 | 3.61(3H, s), 3.76(3H, s), 6.4–6.6(2H, m), 6.9–7.0 (3H, m), 7.07(1H, t), 7.16 (1H, t), 7.2–7.4(4H, m), 7.46(1H, d), 7.47(1H, s) ppm. |
| I | 205 | 60 | 2.11(3H, s), 3.35(3H, s), 3.40(3H, s), 4.71(2H, s), 6.2–7.2(12H, m), 7.24 (1H, s) ppm. |
| I | 206 | 90 | 2.32(3H, s), 3.55(3H, s), 3.7(3H, s), 4.9(2H, s), 6.45–7.28(12H, m), 7.40 (1H, s) ppm. |
| I | 208 | 90 | 3.54(3H, s), 3.7(3H, s), 3.77(3H, s), 6.44–7.3 (12H, m), 7.39(1H, s) ppm. |
| I | 214 | 90 | 3.56(3H, s), 3.73(3H, s), 5.0(2H, s), 6.5–7.65(12H, m), 7.41(1H, s) ppm. |
| I | 216 | 90 | 3.56(3H, s), 3.69(3H, s), 5.04(2H, s), 6.49–7.57 (12H, m), 7.41(1H, s) ppm. |
| I | 217 | 60 | 3.55(3H, s), 3.65(3H, s), 4.90(2H, s), 7.45(1H, s), 6.4–7.5(12H, m) ppm. |
| I | 218 | 90 | 3.54(3H, s), 3.7(3H, s), 4.9(2H, s), 6.42–7.48 (12H, m), 7.4(1H, s) ppm. |
| I | 220 | 60 | 3.40(3H, s), 3.49(3H, s), 4.85(2H, s), 6.2–7.5(13H, m) ppm. |
| I | 230 | 60 | 3.44(3H, s), 3.52(3H, s), 4.87(2H, s), 6.3–7.6(18H, m) ppm. |
| I | 247 | 90 | 3.5(3H, s), 3.61(3H, s), 5.07(2H, s), 6.41–7.79 (15H, m), 7.42(1H, s) ppm. |
| I | 248 | 90 | 3.56(3H, s), 3.7(3H, s), 5.4(2H, s), 6.5–8.4(15H, m), 7.42(1H, s) ppm. |
| I | 283 | 60 | 3.45(3H, s), 3.59(3H, s), 6.5–8.0(13H, m) ppm. |
| I | 284 | 60 | 3.45(3H, s), 3.57(3H, s), 6.3–7.8(13H, m) ppm. |
| I | 285 | 250 | 3.57(3H, s), 3.72(3H, s), 6.55–7.78(12H, m), 7.45 (1H, s) ppm. |
| I | 288 | 60 | 3.39(3H, s), 3.52(3H, s), 6.4–7.4(10H, m), 7.45(1H, s), 7.7–8.0(2H, m) ppm. |
| I | 290 | 60 | 2.25(3H, s), 3.43(3H, s), 3.55(3H, s), 6.4–7.7(13H, m) ppm. |
| I | 291 | 90 | 2.43(3H, s), 3.54(3H, s), 3.71(3H, s), 6.5–7.68 (12H, m), 7.38(1H, s) ppm. |
| I | 295 | 60 | 3.52(3H, s), 3.67(3H, s), 6.6–8.0(13H, m) ppm. |
| I | 296 | 90 | 3.54(3H, s), 3.72(3H, s), 6.48–8.69(12H, m), 7.41 (1H, s) ppm. |
| I | 318 | 60 | 3.59(3H, s), 3.72(3H, s), 6.7–8.0(12H, m) ppm. |
| I | 332 | 90 | 3.48(3H, s), 3.63(3H, s), 6.48–8.3(15H, m), 7.34 (1H, s) ppm. |
| I | 333 | 90 | 3.44(3H, s), 3.61(3H, s), 6.41–8.71(15H, m), 7.35 (1H, s) ppm. |
| I | 360 | 250 | 3.55(3H, s), 3.71(3H, s), 6.15(1H, s), 6.48–7.39 (14H, m), 7.44(1H, s) ppm. |
| I | 367 | 250 | 3.56(3H, s), 3.70(3H, s), 6.5–6.7(2H, m), 6.95(3H, t), 7.12(2H, q), 7.2–7.4 (4H, m), 7.45(1H, s), 7.48 (1H, d) ppm. |
| I | 368 | 90 | 3.57(3H, s), 3.73(3H, s), 6.33(3H, s), 6.9–7.5(14H, m), 7.46(1H, s) ppm. |
| I | 369 | 60 | 3.5(3H, s), 3.6(3H, s), 4.1(2H, br s), 6.6–7.3 (12H, m), 7.43(1H, s) ppm. |
| I | 370 | 90 | 3.6(3H, s), 3.76(3H, s), 5.24(2H, s), 6.51–8.04 (13H, m), 7.47(1H, s) ppm. |
| I | 371 | 400 | 3.60(3H, s), 3.75(3H, s), 3.76(3H, s), 4.95(2H, s), 6.80–6.94(6H, m), 7.03 (1H, s), 7.08–7.16(2H, q), 7.24–7.30(3H, m), 7.49 (1H, s) ppm. |
| I | 373 | 270 | 3.60(3H, s), 3.76(3H, s), 5.02(2H, s), 6.88–6.96 (2H, d), 6.98–7.40(10H, m), 7.48(1H, s) ppm. |
| I | 374 | 270 | 3.61(3H, s), 3.76(3H, s), 5.05(2H, s), 6.76–7.60 (m), 7.48(s) ppm. |
| I | 376 | 270 | 3.59(3H, s), 3.73(3H, s), 5.08(2H, s), 6.84–6.96 (4H, m), 7.04–7.40(8H, m), 7.46(1H, s) ppm. |
| I | 377 | 400 | 3.59(3H, s), 3.75(3H, s), 3.87(3H, s), 5.10(2H, s), 6.8–6.95(6H, m), 7.05–7.15 (3H, m), 7.22–7.30(3H, m), 7.48(1H, s) ppm. |
| I | 378 | 400 | 3.60(3H, s), 3.75(3H, s), 5.14(2H, s), 6.90–7.04 (5H, m), 7.13–7.19(2H, m), 7.24–7.32(3H, m), 7.47 (1H, s), 7.48–7.60(2H, m) ppm. |
| I | 381 | 270 | 3.59(3H, s), 3.75(3H, s), 5.17(2H, s), 6.75(1H, d), 6.88–7.35(11H, m), 7.48 (1H, s), 7.50(1H, m), 7.85 (1H, d) ppm. |
| I | 382 | 400 | 3.60(3H, s), 3.77(3H, s), 5.10(2H, s) 6.94(2H, d), 7.50(1H, s), 7.10–7.18 (2H, m), 7.40–7.33(4H, m), 7.42(1H, t), 7.48(1H, s), 7.78(1H, s), 7.84(1H, d) ppm. |
| I | 383 | 270 | 3.60(3H, s), 3.72(3H, s), 4.97(2H, s), 6.84–7.36 (12H, m), 7.47(1H, s) ppm. |
| I | 384 | 400 | 3.53(3H, s), 3.68(3H, s), 4.91(2H, s), 6.73–7.26 (12H, m), 7.40(1H, s), ppm. |
| I | 385 | 270 | 3.58(3H, s), 3.73(3H, s), 4.95(2H, m), 6.58(2H, m), 6.66(1H, d), 6.86–7.35 (14H, m) ppm. |

| TABLE NO. | COMPOUND NO. | FREQUENCY (MHz) | |
|---|---|---|---|
| I | 386 | 270 | 3.59(3H, s), 3.73(3H, s), 4.97(2H, s), 6.80–6.92 (4H, m), 7.0–7.32(8H, m), 7.47(1H, s) ppm |
| I | 387 | 270 | 3.60(3H, s), 3.77(3H, d), 3.96(2H, s), 6.60(1H, s), 6.70–6.90(3H, m), 7.18 (2H, q), 7.24–7.36(3H, m), 7.27(1H, s), 7.40–7.48 (3H, m) ppm |
| I | 388 | 400 | 3.60(3H, s), 3.78(3H, s), 4.25(2H, d), 6.68(1H, s), 6.75(1H, s), 6.82(1H, d), 6.90(1H, d), 7.13(4H, m), 7.27(1H, s), 7.42–7.48 (3H, m), 7.57(2H, d) ppm |
| I | 389 | 270 | 3.58(3H, s), 3.72(3H, s), 5.08(2H, s), 6.80–6.96(4H, m), 7.08–7.32(7H, m), 7.46 (1H, s), 7.54(1H, d) ppm. |
| I | 391 | 250 | 2.22(6H, s), 3.65(3H, s), 3.75(3H, s), 6.60–7.30 (11H, m), 7.50(1H, s), ppm |
| I | 392 | 90 | 2.17(3H, s), 2.34(3H, s), 3.55(3H, s) 3.70(3H s), 6.50–7.24(11H, m), 7.51 (1H, s) ppm. |
| I | 393 | 90 | 2.14(3H, s), 2.27(3H, s), 3.59(3h, s), 3.76(3H, s), 6.53–7.28(11H, m), 7.50 (1H, s) ppm. |
| I | 394 | 250 | 2.08(6H, s), 3.52(3H, s), 3.75(3H, s), 6.40–7.20 (11H, m), 7.50(1H, s) ppm. |
| I | 395 | 90 | 2.24(6H, s), 3.61(3H, s), 3.77(3H s), 6.63–7.30 (11H, m) 7.50(1H, s) ppm |
| I | 396 | 90 | 2.28(6H, s), 3.60(3H, s), 3.77(3H, s), 6.63–7.24 (11H, m) 7.51(1H s), ppm. |
| I | 397 | 270 | 3.58(3H, s), 3.73(3H, s), 4.96(2H, s), 6.80(2H, d), 6.86–6.92(2H, m), 7.0–7.16 (3H, m), 7.20–7.38(5H, m), 7.47(1H, s) ppm. |
| I | 399 | 270 | 3.60(3H, s), 3.76(3H, s), 4.08(2H, s), 6.80–7.58 (12H, m), 7.47(1H, s), ppm |
| I | 400 | 400 | 3.59(3H, s), 3.75(3H, s), 4.18(2H, s), 6.85(2H, d), 7.00(1H, s), 7.05(1H, d), 7.10–7.35(5H, m), 7.48 (1H, s), 8.10(2H, d) ppm. |
| I | 401 | 400 | 3.72(3H, s), 3.88(3H, s), 4.22(2H, q), 6.83(1H, s), 6.88–7.0(3H, m), 7.21–7.42 (4H, m), 7.50(3H, d), 7.60 (1H, s), 7.66(1H, m) ppm. |
| I | 402 | 400 | 3.70(3H, s), 3.87(3H, s), 4.70(2H, s) 6.80(1H, d), 6.95–7.05(3H, m), 7.22–7.48(5H, m), 7.59(1H, s), 7.65(2H, s), 7.92(1H, d) ppm |
| I | 405 | 60 | 1.21(9H, s), 3.42(3H, s), 3.46(3H, s), 4.80(2H, s), 6.3–7.3(12H, m), 7.31(1H, s) ppm. |
| I | 406 | 270 | 3.57(3H, s), 3.71(3H, s), 5.32(2H, s), 6.92(1H, d), 7.16(2H, t), 7.24–7.43(8H, m), 7.46(1H, s), 7.66(1H, d), 7.76(1H, d) ppm. |
| I | 407 | 270 | 3.51(3H, s), 3.73(3H, s), 4.59(2H, d), 6.70(1H, t), 6.96(1H, d), 7.08(1H, dd), 7.19(1H, d), 7.22–7.37(9H, m), 7.41(1H, s), 7.48(1H, d) ppm. |
| I | 408 | 270 | 3.59(3H, s), 3.71(3H, s), 4.29(2H, s), 6.94(1H, d) 7.13–7.38(10H, m), 7.45 (1H, s), 7.51(1H, t), 7.63 (1H, d) ppm. |
| I | 409 | 270 | 3.61(3H, s), 3.78(3H, s), 6.99(1H, d), 7.15–7.36 (4H, m), 7.44(1H, t), 7.50 (1H, s), 7.53–7.65(2H, m) 7.78(1H, t), 7.89(1H, d), 8.10–8.19(2H, m) ppm. |
| I | 410 | 400 | 3.60(3H, s), 3.75(3H, s), 5.63(2H, s), 6.6–7.3(12H, m), 7.47(1H, s) ppm. |
| I | 411 | 400 | 3.60(3H, s), 3.75(3H, s), 4.8(1H, d), 4.94(1H, d), 6.6–7.7(13H, m), 7.47(1H, s) ppm. |
| I | 412 | 270 | 1.67(3H, d), 3.55(3H, s), 3.70(3H, s), 5.45(1H, q), 6.5–8.1(13H, m), 7.45(1H, s) ppm. |
| I | 413 | 270 | 3.59(3H, s), 3.73(3H, s), 5.17(2H, s), 6.90–6.99 (2H, m), 7.12–7.43(1H, m), 7.49(1H, s), 8.08(1H, s) ppm. |
| I | 414 | 270 | 3.55(3H, s), 3.70(3H, s), 5.21(2H, s), 6.91–7.0(2H, m), 7.10–7.19(1H, m), 7.21–7.38(9H, m), 7.46 (1H, s), 7.53–7.60(2H, m) ppm. |
| I | 415 | 270 | 2.05(2H, m), 2.78(2H, t), 3.60(3H, s), 3.75(3H, s), 3.90(2H, t), 6.5–7.3(13H, m), 7.48(1H, s) ppm. |
| I | 416 | 270 | 1.78(4H, m), 2.65(2H, m), 3.60(3H, s), 3.75(3H, s), 3.9(2H, m), 6.5–7.3(13H, m), 7.47(1H, s) ppm. |
| I | 417 | 270 | 1.44–1.85(6H, m), 2.62 (2H, t), 3.60(3H, s), 3.75 (3H, s), 3.87(2H, t), 6.48–7.31(13H, m), 7.48 (1H, s) ppm. |
| I | 418 | 270 | 3.61(3H, s), 3.76(3H, s), 5.68(1H, s), 6.8–7.6(10H, m), 7.50(1H, s), 7.8(2H, m) ppm. |
| I | 419 | 270 | 3.60(3H, s), 3.74(3H, s), 3.89(3H, s), 6.9–7.6(10H, m), 7.49(1H, s), 7.9(2H, m) ppm. |
| I | 420 | 270 | 3.62(3H, s), 3.78(3H, s), 6.72–7.67(13H, m), 7.49 (1H, s) ppm. |
| I | 422 | 270 | 3.62(3H, s), 3.80(3H, s), 3.87(3H, s), 6.72–7.48 (12H, m), 7.48(1H, s), 7.78(1H, s) ppm. |
| I | 423 | 270 | 3.60(3H, s), 3.70(3H, s), 4.23(4H, m), 6.53–7.3 (13H, m), 7.45(1H, s) ppm. |
| I | 424 | 60 | 3.40(3H, s), 3.50(3H, s), 6.40–8.4(15H, m), 8.95 (1H, s) ppm. |
| I | 425 | 270 | 3.60(3H, s), 3.75(3H, s), 5.40(2H, s), 6.55–7.5 (13H, m), 7.47(1H, s) ppm. |

-continued

| TABLE NO. | COMPOUND NO. | FREQUENCY (MHz) | |
|---|---|---|---|
| I | 426 | 90 | 3.53(3H, s), 3.61(3H, s), 3.63(3H, s), 3.66(3H, s), 4.90(2H, s), 6.40–7.6 (14H, m) ppm. |
| I | 427 | 90 | 3.43(3H, s), 3.61(3H, s), 6.4–7.4(10H, m), 7.32(1H, s), 7.77(2H, d) ppm. |
| I | 428 | 90 | 3.55(3H, s), 3.65(3H, s), 3.85(3H, s), 6.7–8.0(13H, m) ppm. |
| I | 443 | 270 | 3.59(3H, s), 3.74(3H, s), 5.17(2H, s), 6.6–7.4(14H, m), 7.47(1H, s) ppm. |
| II | 23 | 270 | 3.63(3H, s), 3.74(3H, s), 6.97–7.05(3H, m), 7.10 (1H, d), 7.22–7.33(4H, m), 7.48(1H, d), 7.49(1H, s), 8.54(2H, d) ppm. |
| II | 30 | 270 | 3.60(3H, s), 3.74(3H, s), 6.73–7.35(8H, m), 7.49 (1H, s), 8.10(1H, m), 8.25 (1H, m), 8.38(1H, m) ppm. |
| II | 47 | 270 | 3.60(3H, s), 3.75(3H, s), 5.52(2H, s), 6.96(2H, d), 7.07–7.40(8H, m), 7.49 (1H, s), 7.61–7.71(2H, q) ppm. |
| II | 52 | 60 | 3.51(3H, s), 3.64(3H, s), 7.40(1H, s), 6.5–7.8(11H, m) ppm. |
| II | 53 | 270 | 3.60(3H, s), 3.75(3H, s), 6.74–7.35(9H, m), 7.49 (1H, s), 7.88(1H, m), 8.43 (1H, m) ppm. |
| II | 69 | 270 | 3.60(3H, s), 3.75(3H, s), 6.73–7.36(9H, m), 7.49 (1H, s), 7.89(1H, m), 8.45 (1H, m). |
| II | 81 | 270 | 3.63(3H, s), 3.78(3H, s), 5.32(2H, s), 6.84–6.92 (4H, m), 7.10–7.30(4H, m), 7.48(1H, s), 7.98(1H, s), 8.08(1H, s) ppm. |
| II | 83 | 90 | 3.54(3H, s), 3.65(3H, s), 6.76–7.68(12H, m), 7.38 (1H, s) ppm. |
| II | 86 | 90 | 3.62(3H, s), 3.79(3H, s), 6.8–7.5(8H, m), 7.52(1H, s) ppm. |
| II | 87 | 270 | 3.61(3H, s), 3.76(3H, s), 6.66–6.74(2H, m), 6.79 (1H, dd), 7.00(1H, d), 7.16(1H, m), 7.24–7.34 (3H, m), 7.47(1H, s), 8.47 (2H, s), 8.96(1H, s) ppm. |
| II | 88 | 90 | 3.62(3H, s), 3.76(3H, s), 4.30(3H, s), 6.80–7.42 (8H, m), 7.50(1H, s) ppm. |
| II | 90 | 270 | 3.61(3H, s), 3.76(3H, s), 6.77(1H, t), 6.86(2H, m), 7.04(1H, d), 7.15(1H, m), 7.29(3H, m), 7.48(1H, s), 8.55(2H, s) ppm. |
| II | 91 | 270 | 3.61(3H, s), 3.75(3H, s), 6.77(1H, t), 6.83–6.89 (2H, m), 7.04(1H, d), 7.15 (1H, t), 7.25–7.35(3H, m), 7.48(1H, s), 8.47(2H, s) ppm. |
| II | 93 | 270 | 3.60(3H, s), 3.75(3H, s), 3.90(3H, s), 3.94(3H, s), 5.67(1H, t), 6.76(1H, t), 6.84(2H, m), 7.00(1H, d), 7.15(1H, m), 7.25–7.32 (2H, m), 7.48(1H, s) ppm. |
| II | 96 | 270 | 3.61(3H, s), 3.75(3H, s), 6.75(1H, t), 6.83(1H, dd), 6.95(1H, dd), 7.07 (1H, d), 7.18(1H, m), 7.29–7.37(3H, m), 7.49 (1H, s) ppm. |
| II | 97 | | Proton-decoupled Carbon-13 n.m.r. at 67.7 MHz: delta 51.25, 61.59, 106.54, 107.41, 110.85, 114.96, 115.45, 119.58, 123.72, 125.06, 128.90, 130.05, 132.41, 152.29, 153.57, 158.81, 160.03, 160.13, 160.22, 167.49, 169.95 ppm. |
| II | 98 | 270 | 2.72(3H, s), 3.60(3H, s), 3.77(3H, s), 5.08(2H, s), 6.5–7.4(9H, m), 7.48(1H, s) ppm. |
| II | 99 | 270 | 3.60(3H, s), 3.74(3H, s), 5.50(2H, s), 6.92–7.0(2H, m), 7.09–7.36(9H, m), 7.47 (1H, s), 7.50(1H, d) ppm. |
| II | 100 | 270 | 3.60(3H, s), 3.75(3H, s), 5.33(2H, s), 6.90–6.96 (2H, m), 7.06–7.18(3H, m), 7.24–7.34(3H, m), 7.49 (1H, s), 8.07(1H, d), 8.14 (1H, d), 8.28(1H, s) ppm. |
| II | 101 | 270 | 3.60(3H, s), 3.75(3H, s), 5.31(2H, s), 6.90–6.99 (2H, m), 7.06 (1H, s), 7.10–7.18(2H, m), 7.25–7.34(3H, m), 7.49(1H, s), 8.17(2H, s) ppm. |
| II | 102 | 270 | 3.60(3H, s), 3.75(3H, s), 5.50(2H, s), 6.89–6.99 (3H, m), 7.1–7.42(7H, m), 7.49(1H, s), 7.62(1H, t), 7.71(1H, d), 7.83(1H, d), 8.0(1H, d) ppm. |
| II | 103 | 270 | 3.60(3H, s), 3.77(3H, s), 5.49(2H, s), 6.90–6.98 (2H, m), 7.0(1H, d), 7.08–7.20(3H, m), 7.24–7.33 (3H, m), 7.39(1H, d), 7.49 (1H, s) ppm. |
| II | 104 | 270 | 3.44(3H, s), 3.70(3H, s), 5.09(2H, s), 6.82(2H, d), 6.90(1H, d), 7.0–7.14(4H, m), 7.16–7.36(3H, m), 7.49 (1H, s), 8.05(2H, d) ppm. |
| II | 105 | 270 | 3.60(3H, s), 3.75(3H, s), 5.38(2H, s), 6.82–6.98 (3H, m), 7.05–7.20(3H, m), 7.20–7.35(3H, m), 7.48 (1H, s), 7.78(1H, d), 8.43 (1H, s) ppm. |
| II | 106 | 270 | 3.60(3H, s), 3.76(3H, s), 6.74–7.38(9H, m), 7.48 (1H, s), 7.98(1H, m), 8.30 (1H, m) ppm. |
| II | 107 | 270 | 3.60(3H, s), 3.76(3H, s), 6.75–7.37(9H, m), 7.49 (1H, s), 8.45(1H, m), 9.03 (1H, m) ppm. |
| II | 270 | 270 | 3.61(3H, s), 3.78(3H, s), 6.28(1H, m), 6.70(2H, m), 6.9–7.5(9H, m), 7.48(1H, s), 9.55(1H, br, s) ppm. |
| II | 271 | 270 | 3.60(3H, s), 3.74(3H, s), 6.74–7.39(9H, m), 7.50 (1H, s), 8.32(1H, m) ppm. |
| II | 272 | 270 | 2.32(3H, s), 2.54(3H, s), 3.60(3H, s), 3.76(3H, s), |

-continued

| TABLE NO. | COMPOUND NO. | FREQUENCY (MHz) | |
|---|---|---|---|
| II | 273 | 270 | 6.72–7.35(8H, m), 7.49 (1H, s), 8.00(1H, s) ppm. 3.60(3H, s), 3.72(3H, s), 6.72–7.36(8H, m), 7.50 (1H, s), 8.26(2H, m) ppm. |
| II | 274 | 270 | 3.60(3H, s), 3.75(3H, s), 4.04(3H, s), 6.74–7.36 (10H, m), 7.50(1H, s) ppm. |
| II | 310 | 270 | 3.60(3H, s), 3.75(3H, s), 5.30(2H, s), 6.72(1H, d), 6.87–7.35(9H, m), 7.43 (1H, t), 7.49(1H, s) ppm. |
| II | 311 | 270 | Data in common for both regioisomers: 3.60(3H, s), 3.77(3H, s), 5.38(2H, s), 6.90–7.18(5H, m), 7.23–7.33(3H, m), 7.49 (1H, s) ppm. Data for major isomer: 6.70(1H, d), 8.32(1H, d) ppm. Data for minor isomer: 6.98 (1H, d), 8.38(1H, d) ppm. |
| II | 315 | 270 | 3.39(3H, s), 3.60(3H, s) 3.73(3H, s), 3.84(3H, s), 5.63(1H, m), 5.85(1H, m), 6.59(1H, m), 6.7–7.3(8H, m), 7.47(1H, m) ppm. |
| II | 8 | 270 | 3.60(3H, s), 3.75(3H, s), 6.62–7.36(10H, m), 7.48 (1H, s), 8.38(2H, m) ppm. |
| II | 15 | 270 | 3.60(3H, s), 3.74(3H, s), 6.66–7.37(10H, m), 7.48 (1H, s), 8.45(2H, m) ppm. |
| II | 35 | 270 | 3.60(3H, s), 3.74(3H, s), 6.70–7.50(10H, m), 7.49 (1H, s), 8.92(1H, m) ppm. |
| II | 313 | 270 | 2.38(3H, s), 2.41(3H, s), 3.59(3H, s), 3.75(3H, s), 6.29(1H, s), 6.75(1H, t), 6.84(2H, t of d), 6.98 (1H, d), 7.15(1H, t), 7.25–7.34(3H, m), 7.48 (1H, s) ppm. |
| II | 319 | 270 | 2.90(6H, s), 3.60(3H, s), 3.77(3H, s), 6.18(1H, d), 6.75–7.37(8H, m), 7.48 (1H, s), 8.22(1H, d) ppm. |
| II | 320 | 270 | Data in common for both regioisomers: 3.61(3H, s), 3.74(3H, s), 7.50(1H, s) ppm. Data for major isomer: 2.35(3H, s) ppm. Data for minor isomer: 2.38(3H, s) ppm. |
| III | 23 | 270 | 3.65(3H, s), 3.75(3H, s), 4.97(2H, s), 6.75–6.87(3H m), 7.14(1H, t), 7.21–7.40 (9H, m), 7.49(1H, s) ppm. |
| III | 51 | 270 | 3.61(3H, s), 3.73(3H, s), 6.75–6.82(2H, m), 7.02–7.17(2H, m), 7.22–7.38 (3H, m), 7.46(1H, s), 7.47–7.59(4H, m), 7.62–7.72(1H, m), 7.80(1H, d) ppm. |
| III | 131 | 270 | 3.63(3H, s), 3.74(3H, s), 6.80(1H, d), 6.86(1H, s), 6.99(2H, d), 7.15–7.37 (6H, m), 7.48(1H, s), 7.46 (1H, d), 7.93(1H, d) ppm. |
| III | 212 | 270 | 3.65(3H, s), 3.77(3H, s), 5.08(2H, s), 6.74–6.80 (2H, m), 6.85–6.89(1H, d), 7.16(1H, t), 7.20–7.38 (4H, m), 7.49(1H, s), 7.54 (2H, d), 8.21(2H, d) ppm. |
| IV | 87 | 270 | 3.64(3H, s), 3.75(3H, s), 6.80(1H, d), 6.86(1H, s), 7.03(1H, d), 7.21–7.38 (4H, m), 7.47(1H, d), 7.48 (1H, s), 8.44(2H, s), 8.95 (1H, s) ppm. |

The compounds of the invention of formula (I) can be made by a variety of methods, and some of these are illustrated in Schemes I to VIII. Throughout these Schemes, the terms Z, X, A, B, E, K, $R^1$, $R^2$, $R^3$, $R^4$ and $R^5$ are as defined above, $R^6$ is hydrogen or a metal (such as sodium or potassium), R is an alkyl group, and L is a leaving group such as a halide (chloride, bromide or iodide), a $CH_3SO_4$- anion, or a sulphonyloxy-anion. Each of the transformations described in Schemes I to VIII is performed at a suitable temperature and either in a suitable solvent or in the absence of a solvent.

Scheme I illustrates ways in which the methyl beta-methoxypropenoate group can be constructed in the final stages of the preparation of the compounds of the invention from precursors with a preformed framework of 3 aromatic rings. Alternatively, the methyl beta-methoxy-propenoate group may be constructed at an earlier stage of the preparation, in which case the final step or steps comprise elaboration of other parts of the compounds of the invention to form the framework of 3 aromatic rings. Examples of procedures of this kind are shown in Schemes III to VIII.

In whichever order the steps are carried out to prepare the compounds of the invention, the diphenyl ether or thioether linkage which is common to all the compounds of the invention can be prepared by one of the coupling reactions shown in Scheme II. For a review of the Ullmann ether synthesis see A. A. Moroz and M. S. Shrartsberg, *Russian Chem. Reviews*, 1974, 43, 679. See also D. Hands, H. Marley, S. J. Skittrall, S. H. B. Wright and T. R. Verhoeven, *J. Heterocyclic Chem.*, 1986, 23, 1333. These couplings are often performed in the presence of a catalyst which consists of a transition metal or a salt or compound of a transition metal, such as copper or a copper salt or compound, or a mixture thereof. In Scheme II, the term W represents either the group Z—X—, wherein Z and X are as defined above, or a group which can be converted by standard procedures described in the chemical literature into the group Z—X—; for example W can be —OH, —SH, or —NHR$_4$. The term Y represents either the alpha-linked methyl beta-methoxypropenoate group of the compounds of the invention or a group which can be converted into such a group by standard methods described in the chemical literature and/or described in Scheme I and the following d paragraphs. For example Y can be —$CH_2COOH$, —$CH_2COOMe$ or —CHO. In the context of Scheme II, the term L is preferably a halogen. Thus compounds of formula (XI) react with compounds of formula (XII) under the conditions of the Ullmann reaction already described to give the intermediates of formula (VIII). As an example of one of the coupling reactions shown in Scheme II, substituted 3-phenoxyphenols, as their salts, undergo coupling with 2-bromo- or 2-chlorophenylacetic acid salts to give, after acidification, substituted 2-(3-phenoxyphenoxy)phenylacetic acids (compare, for example, GB 2078-743, Ihara Chem. Ind., 27.06.80). Alternatively, intermediates of formula (VIII) can be made by reacting compounds of formula (IX) with compounds of formula (X) under the conditions of the Ullmann reaction already described.

In one particular aspect, the invention includes a process for the preparation of the compound of formula (I) which comprises reacting a compound of general formula (XIIa):

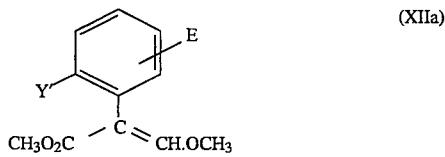

(XIIa)

wherein Y' is halogen with a phenol or thiophenol of general formula (XIa):

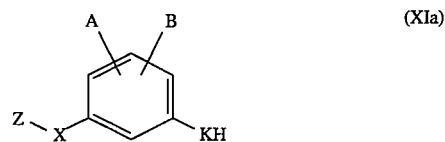

(XIa)

in the presence of a base, or with a salt of the phenol or thiophenol (XIa), preferably in the presence of a catalyst which comprises a suitable transition metal, a transition metal salt or compound or a mixture thereof.

The compounds of the invention of formula (I) can be prepared from the phenylacetates of formula (III) or the ketoesters of formula (VI) by the steps shown in Scheme I.

Thus compounds of formula (I) can be prepared by treatment of phenylacetates of formula (III) with a base (such as sodium hydride or sodium methoxide) and methyl formate. If a species of formula $CH_3L$, wherein L is as defined above, is then added to the reaction mixture, compounds of formula (I) may be obtained. If a protic acid is added to the reaction mixture, compounds of formula (II) wherein $R^6$ is hydrogen are obtained. Alternatively, the species of formula (II) wherein $R^6$ is a metal (such as sodium) may themselves be isolated from the reaction mixture.

Compounds of formula (II) wherein $R^6$ is a metal can be converted into compounds of formula (I) by treatment with a species of formula $CH_3L$, wherein L is as defined above. Compounds of formula (II) wherein $R^6$ is hydrogen can be converted into compounds of formula (I) by successive treatments with a base (such as potassium carbonate) and a species of general formula $CH_3L$.

Alternatively, compounds of formula (I) can be prepared from acetals of formula (IV) by elimination of methanol under either acidic or basic conditions. Examples of reagents or reagent mixtures which can be used for this transformation are lithium di-isopropylamide; potassium hydrogen sulphate (see, for example, T. Yamada, H. Hagiwara and H. Uda, *J. Chem. Soc., Chemical Communications*, 1980, 838, and references therein); and triethylamine, often in the presence of a Lewis acid such as titanium tetrachloride (see, for example, K. Nsunda and L. Heresi, *J. Chem. Soc., Chemical Communications*, 1985, 1000).

Acetals of formula (IV) can be prepared by treatment of methyl silyl ketene acetals of formula (V), wherein R is an alkyl group, with trimethyl orthoformate in the presence of a Lewis acid such as titanium tetrachloride (see, for example, K. Saigo, M. Osaki and T. Mukaiyama, *Chemistry Letters*, 1976, 769).

Methyl silyl ketene acetals of formula (V) can be prepared from phenylacetates of formula (III) by treatment with a base and a trialkylsilyl halide of formula $R_3SiCl$ or $R_3SiBr$, such as trimethylsilyl chloride, or a base (such as triethylamine) and a trialkylsilyl triflate of formula $R_3Si—OSO_2CF_3$ (see, for example, C. Ainsworth, F. Chen and Y. Kuo, *J. Organometallic Chemistry*, 1972, 46, 59).

It is not always necessary to isolate the intermediates (IV) and (V); under appropriate conditions, compounds of formula (I) may be prepared from phenylacetates of formula (III) in "one pot" by the successive addition of suitable reagents listed above.

Alternatively, compounds of formula (I) can be prepared by treatment of ketoesters of formula (VI) with a methoxymethylenating reagent, for example, methoxymethylenetriphenylphosphorane (see, for example, W. Steglich, G. Schramm, T. Anke and F. Oberwinkler, EP 0044448, 4.7.1980).

Ketoesters of formula (VI) may be prepared by methods described in the literature. Particularly useful methods include (i) the reaction of appropriate phenylmagnesium halides or phenyl-lithium species with dimethyl oxalate using the method described by L. M. Weinstock, R. B. Currie and A. V. Lovell, *Synth. Commun.*, 1981, 11, 943 and references therein; (ii) oxidation of phenylacetates of formula (III) using selenium dioxide, generally in the absence of a solvent, and generally at a temperature above 100° C.; and (iii) oxidation of mandelic acid esters using, for example, manganese oxide in a suitable solvent.

Phenylacetates of formula (III) and the corresponding phenylacetic acids of formula (VII) may also be prepared by numerous other methods described in the chemical literature. For example, several useful methods are described by D. C. Atkinson, K. E. Godfrey, B. Meek, J. F. Saville and M. R. Stillings, *J. Med. Chem.*, 1983, 26, 1353 and D. C. Atkinson, K. E. Godfrey, P. L. Meyers, N. C. Phillips, M. R. Stillings and A. P. Welbourn, *J. Med. Chem.*, 1983, 26, 1361. Furthermore, many of the methods described for the preparation of 2-arylpropionic esters and acids by J-P Rieu, A. Boucherle, H. Cousse and G. Mouzin, *Tetrahedron*, 1986, 42, 4095, are also applicable to the preparation of phenylacetates of formula (III) and phenylacetic acids of formula (VII) using appropriate precursors wherein the ortho substituted-phenoxy substituent and the substituent E are already present.

Scheme I
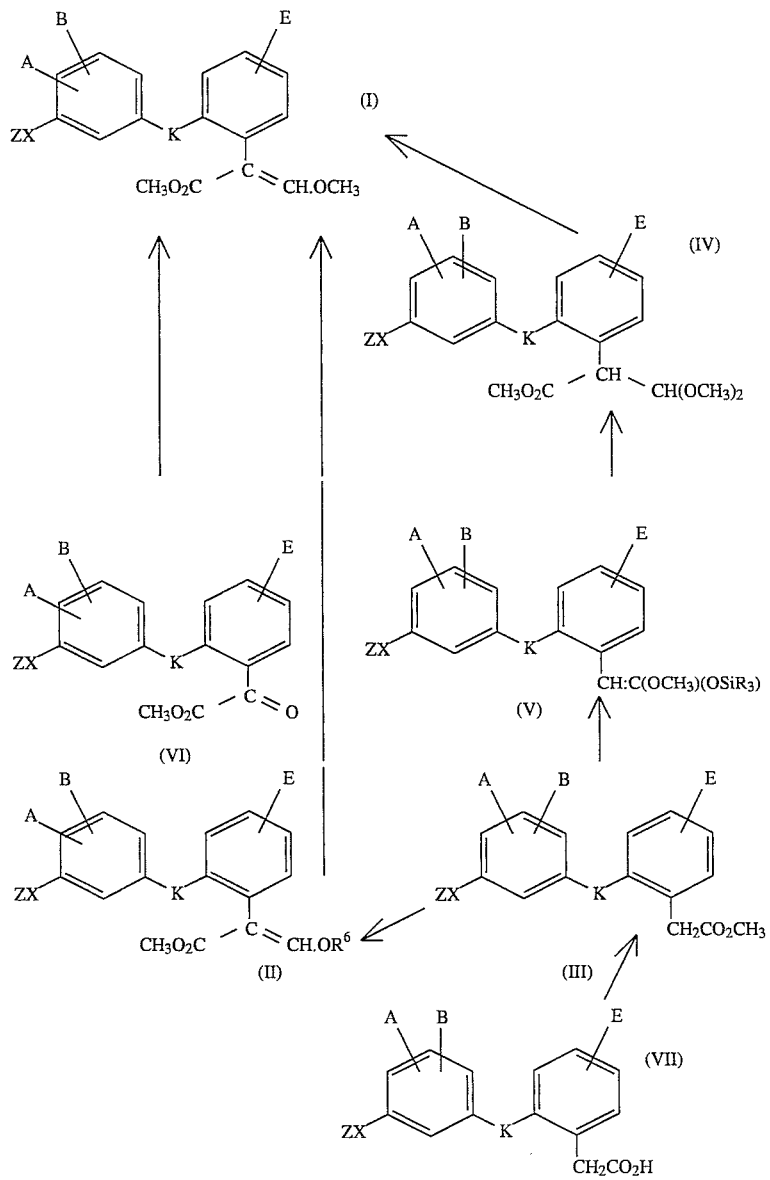

Scheme II

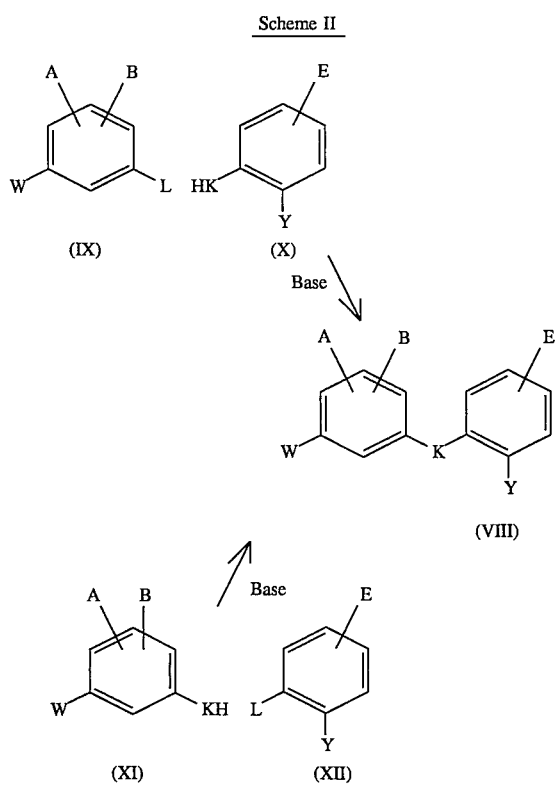

Schemes III, IV, V, VI and VII illustrate examples of intermediates containing the methyl beta-methoxypropenoate group and show how they may be converted into certain specific types of compound of the invention (I).

Thus, in scheme III, in the presence of a base, and sometimes in the presence of a transition metal or transition metal salt catalyst, such as a copper or copper salt catalyst, compounds of formula (XIII) react with aromatic or heteroaromatic compounds of formula ZL, wherein Z and L are as defined above, or with iodonium salts of formula $Z_2I^+T^-$, wherein Z is as defined as above and $T^-$ is a counter ion, such as a halide ion, or with aryl or heteroarylbismuth species, to give compounds of formula (XIV). In addition, in the presence of a base, compounds of formula (XIII) react with aryl- or heteroarylsulphonyl halides of formula $ZSO_2Q$, wherein Z is as defined above and Q is a halogen, to give compounds of formula (XV). Furthermore, and also in the presence of a base, compounds of formula (XIII) react with arylalkyl or heteroarylalkyl species of formula $ZCHR^1L$, wherein Z, $R^1$ and L are as defined above, to give compounds of formula (XVI).

In scheme IV, the thiols of formula (XVII), generally in the presence of a base, react with aromatic or heteroaromatic compounds of formulae ZL, or with iodonium salts of formula $Z_2I^+T^-$, or with aryl- or heteroarylbismuth species, to give compounds of formula (XVIII) in ways which are analogous to the reactions of the corresponding phenols of formula (XIII) shown in Scheme III. Similarly, and again in the presence of a base, the thiols of formula (XVII) react with arylalkyl or heteroarylalkyl species of formula $ZCHR^1L$ to give compounds of formula (XIX). The sulphides of formula (XVIII) and (XIX) can be oxidised to the corresponding sulphoxides and sulphones by standard methods described in the chemical literature.

In Scheme V, compounds of formula (XX) react with hydroxy-derivatives of aromatic or heteroaromatic compounds of formula ZOH, wherein Z is as defined above, often in the presence of a base, to form compounds of formula (XXI). Furthermore, compounds of formula (XX) react with trialkylphosphites of formula $P(OR)3$ or with species of formula $M^{+P-}(O)(OR)_2$, wherein R is as defined above in each case and M is a metal such as sodium or lithium, to give phosphonates of formula (XXII). Phosphonates of formula (XXII), in the presence of a base, react with aldehydes or ketones of formula $ZR^1C{:}O$, wherein Z and $R^1$ are as defined above, to give olefins of formula (XXIV). In addition, aldehydes or ketones of formula (XXIII), on treatment with phosphonate anions of formula $ZR^1C^-P(O)(OR)_2M^+$, wherein Z, R, $R^1$ and M are as defined above, or with the corresponding phosphoranes, also give olefins of formula (XXIV). The olefins of formula (XXIV) can be reduced to the compounds of formula (XXV) by, for example, hydrogenation over an appropriate catalyst.

In Scheme VI, compounds of formula (XXVI), in the presence of a base, react with acid halides of formula ZCOQ, wherein Z and Q are as defined above, or, in the presence of an appropriate dehydrating agent, react with acids of formula $ZCO_2H$, wherein Z is as defined above, to give compounds of formula (XXVII).

Intermediates of formula (XXVI) can also be converted into other types of compound of the invention of formula (I) by methods described in the chemical literature. For example, compounds of formula (XXVI) wherein $R^4$ is hydrogen can be converted, via diazotisation, into the corresponding sulphonyl chlorides (compare *Organic Syntheses*, 1981, 6D, 121) and then, by treatment with alcohols or phenols in the presence of a base, into sulphonic esters.

Compounds of the invention of formula (I) Wherein at least one of A and B is hydrogen may be converted into compounds of the invention of formula (I) wherein at least one of A and B are certain substituents (such as a halogen or a nitro or acyl group) by electrophilic substitution processes of the kind described in the chemical literature.

The intermediates of formulae (XIII), (XVII), (XX), (XXIII) and (XXVI) can be prepared by processes described in the chemical literature and by processes of the kinds described in Schemes I and II. For example, compounds of formula (XX) where L is bromine can be made from compounds of formula (XX) where L is H, by reaction with N-bromosuccinimide or N,N-dibromo-dimethylhydantoin, in the presence or absence of irradiation by light.

The intermediates of formulae (IX), (X), (XI), (XII), ZL,, $Z_2I^+T^-$, $ZCHR^1L$, $ZSO_2Q$, ZOH, $ZR^1C{:}O$, $ZR^1C^-P(O)(OR)_2$ $M^+$, ZCOQ and $ZCO_2H$ can be made by methods described in the chemical literature.

Scheme III
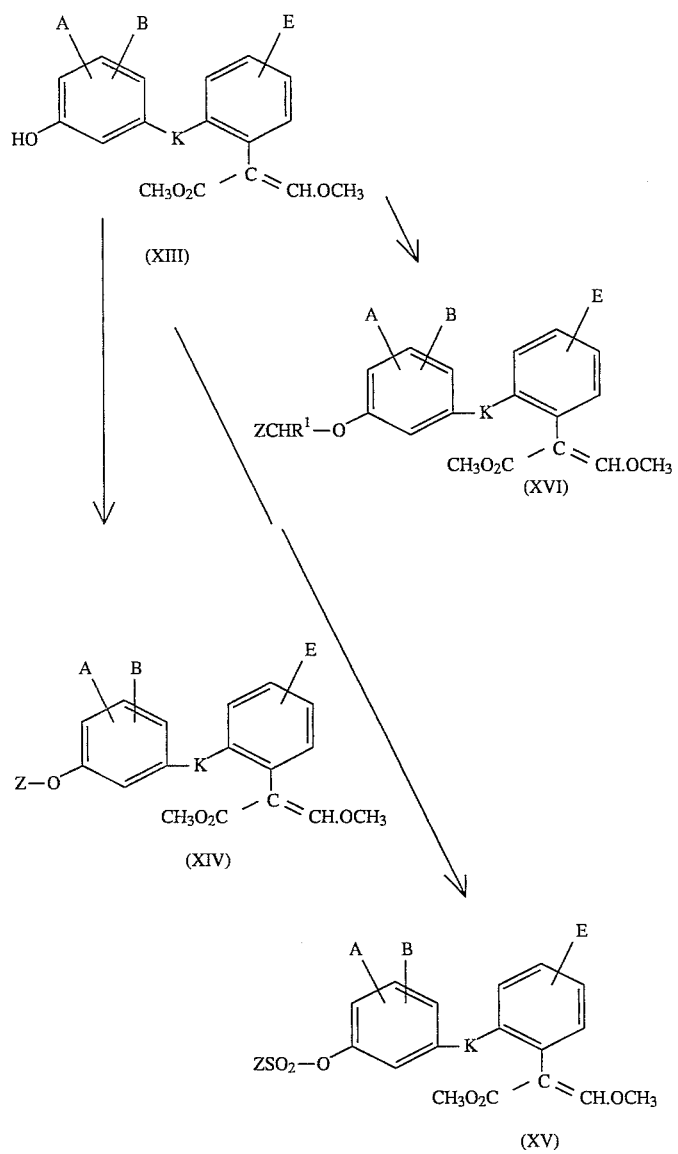
Scheme IV
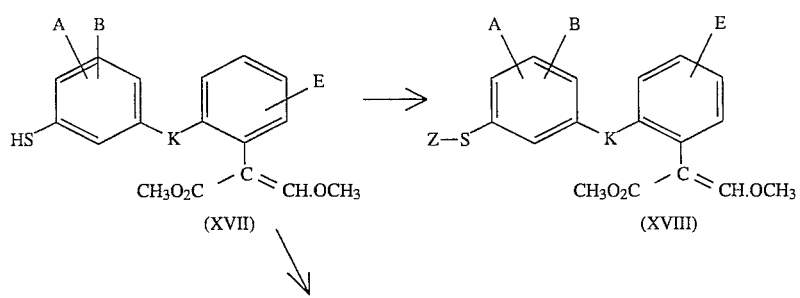

Scheme IV
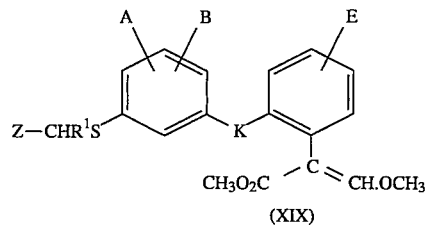
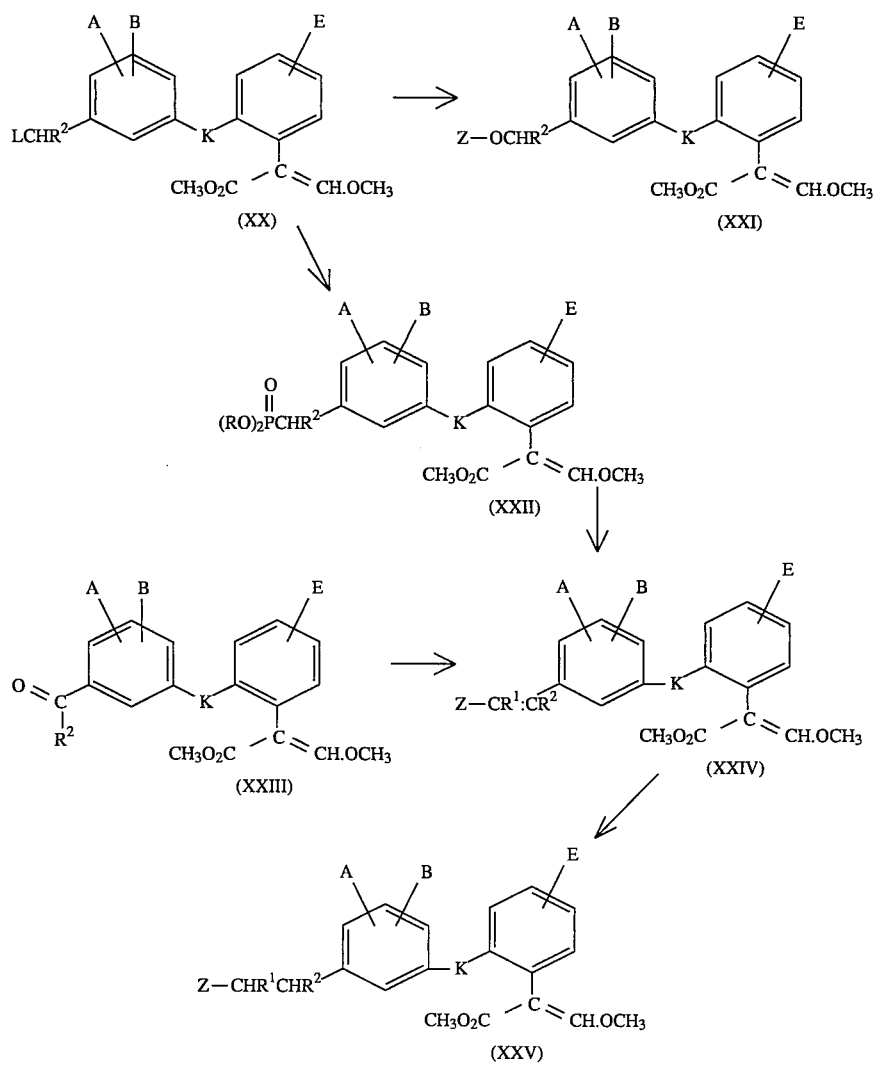

Scheme VI

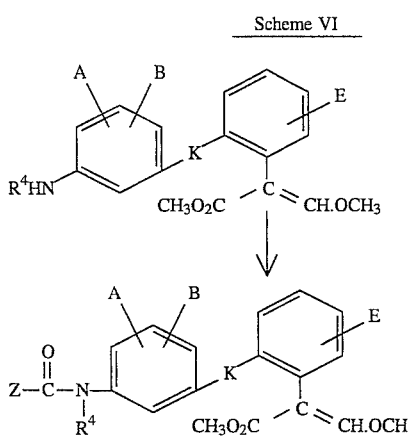

In Scheme VII compounds of formula (XXVIII) can be oxidised, for example using pyridinium dichromate in a suitable solvent (such as methylene chloride) or oxalyl chloride in dimethyl sulphoxide in the presence of a base (the Swern oxidation), to give aldehydes (where $R^2$ is H) or ketones (where $R^2$ is alkyl) of formula (XXIII). The aldehydes or ketones of formula (XXIII) can react with oxyamines of formula $ZONH_2$ or $ZCHR^1ONH_2$, or with hydrazines of formula $ZNR^1NH_2$, wherein Z and $R^1$ are as defined above, to give compounds of the invention of formula (I) where X is the group $ON=CR^2$, $CHR^1ON=CR^2$, or $NR^1N=CR^2$ respectively. Also, compounds of formula (XXIII) can react with Grignard reagents of formula ZMgHal or $ZCHR^1MgHal$, where Hal is chlorine, bromine or iodine and Z, and $R^1$ are as defined above, to give compounds of the invention of formula (I) where X is $CR^2(OH)$ or $CHR^1.CHOH$ respectively. Also, compounds of formula (XXIII) can react with anamine of formula $ZNHR^{10}$, wherein Z is as defined above and $R^{10}$ is hydrogen or $C_{1-4}$ alkyl in the presence of a reducing agent (such as sodium cyanoborohydride or hydrogen gas in the presence of a suitable metal catalyst) to give a compound of the invention of formula (I) where X is $NR^{10}CHR^2$, When the reducing agent is left out and when $R^{10}$ is H, then the immediately preceding procedure will give compounds of the invention of formula (I) where X is $N=CR^2$ or when an amine of the formula $ZCHR^1O.NH_2$ is used, $CHR^1O.N=CR^2$.

Compounds of formula (XXVIII) where $R^2$ is H, can also be oxidised to carboxylic acids of formula (XXIX), using for example Jones' reagent (chromium trioxide in sulphuric acid). The carboxylic acids (XXIX) can be converted directly into compounds of the invention of formula (I) where, for example, X is $O_2C$, $CHR^1OCO$, SCO, $CHR^1SCO$, $NR^4CO$ or $CHR^1NR^4CO$, using one of the standard coupling reagents well known in the literature, such as dicyclohexylcarbodiimide or carbonyldiimidazole, in a suitable solvent.

Alternatively, the carboxylic acids of formula (XXIX) can be converted into the acid chlorides of formula (XXX) by treatment with, for example, thionyl chloride or oxalyl chloride. The acid chlorides of formula (XXX) can then react, for example, with compounds of formula ZOH, $ZCHR^1OH$, ZSH, $ZCHR^1SH$, $ZNR^4H$ or $ZCHR^1NR^4H$ in a suitable solvent, in the presence of a base, to give compounds of the invention of formula (I) where X is $O_2C$, $CHR^1OCO$, SCO, $CHR^1SCO$, $NR^4CO$, or $CHR^1NR^4CO$ respectively.

Compounds of formula (XXVIII) can also react directly with compounds of formula ZL, optionally in the presence of a base, where Z is a reactive aromatic group (for example nitrophenyl) or heteroaromatic group (for example 2-pyridyl or 2-pyrimidinyl) to give compounds of the invention of formula (XXI). It may be necessary first to generate the oxygen anion of compounds of formula (XXVIII) with a strong base such as sodium hydride.

Additionally, compounds of formula (XXVIII) can be converted into compounds of formula (XX) by treatment, for example, with a halogenation agent such as thionyl chloride or phosphorus tribromide, where L is chlorine or bromine, or by treatment with a sulphonyl halide (such as p-toluenesulphonyl chloride) in the presence of an acid acceptor, where L is a sulphonyloxy group. Compounds of formula (XX) can then be used as shown in Scheme V. Additionally, where L is halogen, they can be converted by reaction with a phosphine of formula $Z(R^5)_2P$, wherein $R^5$ is as defined above, into compounds of the invention of formula (I), where X is the group $(R^5)_2P^+CHR^2Q^-$. These compounds can then react successively with a base and a carbonyl compound of formula $ZCOR^1$, wherein Z and $R^1$ are as defined above, to give olefins of formula.(XXIV).

Scheme VIII illustrates examples of intermediates of formula (VIII), shown in Scheme II, where W is any group that can be converted to ZX—, and Y is any group that can be converted to the methyl beta-methoxypropenoate group.

Compounds of formula (XXXI) can react with compounds of formula (XXXII) to give compounds of formula (XXXIII), using the general Ullmann coupling conditions described in detail for the reaction of compounds of formula (XI) and (XII) in Scheme II. The acids of formula (XXXIII) can be converted into methyl esters of formula (XXXIV) by reaction with methanol in the presence of acid (for example hydrochloric acid). Compounds of formula (XXXIV) can then be converted into methyl beta-methoxypropenoates of formula (XXVIII) by the methods described in detail in Scheme I.

Alternatively, the intermediates of formula (XXXIV) can be Converted into intermediates of formulae (XXXVIII), (XXXV), (XXXVI), (XXXVII) and (III) using the methods described in Scheme VII for the conversion of the propenoates of formula (XXVIII) into compounds of formula (XXIII), (XX), (XXIX), (XXX) and (I). Compounds of formula (III) can be converted into compounds of formula (I) as shown in Scheme I.

Scheme VII
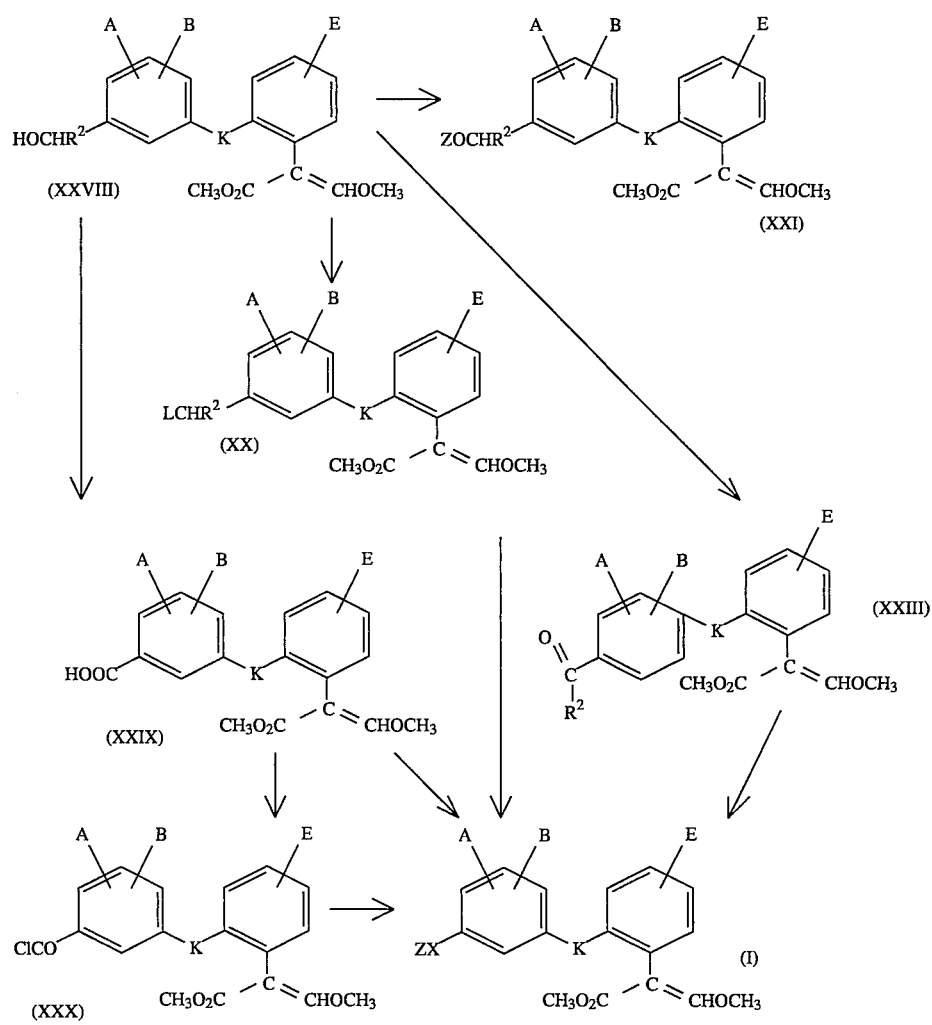
Scheme VIII
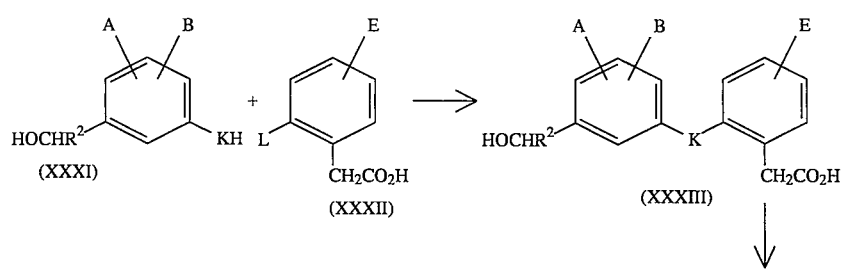

-continued
Scheme VIII

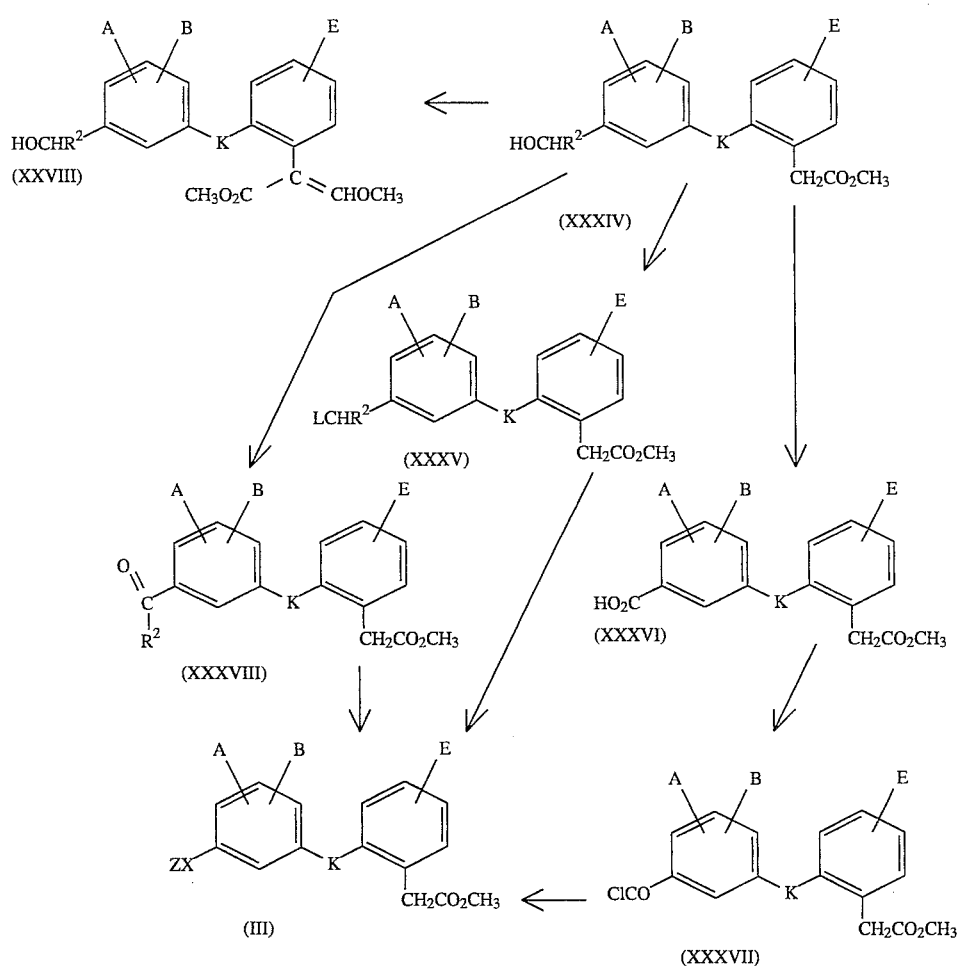

In a further aspect the invention provides processes as hereindescribed for preparing the compounds of formula (I). It also provides intermediate chemicals of formulae (II)–(VII), (XIII)–(XXX), and (XXXIII)–(XXXVIII).

The compounds are active fungicides and may be used to control one or more of the following pathogens:

*Pyricularia oryzae* on rice.

*Puccinia recondita, Puccinia striiformis* and other rusts on wheat, *Puccinia hordei, Puccinia striiformis* and other rusts on barley, and rusts on other hosts, e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

Helminthosporium spp., Rhynchosporium spp., Septoria spp., *Pseudocercosporella herepotrichoides* and *Gaeumannomyces graminis* on cereals. *Cercospora arachidicola* and *Cercosporidium personata* on peanuts and other Cercospora species on other hosts, for example, sugar beet, bananas, soya beans and rice.

*Botrytis cinerea* (grey mould) on tomatoes, strawberries, vegetables, vines and other hosts.

*Alternaria* species on vegetables (e.g. cucumber), oil-seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soya beans, tobacco, onions and other hosts and *Pseudoperonospora humuli* on hops and *Pseudoperonospora cubensis* on cucurbits.

*Phytophthora infestans* on potatoes and tomatoes and other Phytophthora spp. on vegetables, strawberries, avocado, pepper, ornamentals, tobacco, cocoa and other hosts.

*Thanatephorus cucumeris* on rice and other Rhizoctonia species on various host such as wheat and barley, vegetables, cotton and turf.

Some of the compounds show a broad range of activities against fungi in vitro. They may also have activity against various post-harvest diseases of fruit (e.g. *Penicillium digitatum* and *italicum* and *Trichoderma viride* on oranges, *Gloeosporium musarum* on bananas and *Botrytis cinerea* on grapes).

Further, some of the compounds may be active as seed dressings against Fusarium spp., Septoria spp., Tilletia spp., (bunt, a seed borne disease of wheat), Ustilago spp., Helminthosporium spp. on cereals, *Rhizoctonia solani* on cotton and *Pyricularia oryzae* on rice.

The compounds may have systemic movement in plants. Moreover, the compounds may be volatile enough to be active in the vapour phase against fungi on the plant.

Many of the compounds of formula (I), including those in which X is O, are safer on certain crops (e.g. vines) than known structurally related compounds.

The invention therefore provides a method of combating fungi, which comprises applying to a plant, to seed of a plant, or to the locus of the plant or seed, an effective amount of a compound as hereinbefore defined, or a composition containing the same.

The compounds may also be useful as industrial (as opposed to agricultural) fungicides, e.g. in the prevention of fungal attack on wood, hides, leather and especially paint films.

The compounds may be used directly for fungicidal purposes but are more conveniently formulated into compositions using a carrier or diluent. The invention thus provides a fungicidal composition comprising a compound of general formula (I) as hereinbefore defined, and a fungicidally acceptable carrier or diluent.

Used as fungicides, the compounds can be applied in a number of ways. For example they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules. Application can be to any part of the plant including the foliage, stems, branches or roots, or to soil surrounding the roots, or to the seed before it is planted; or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. the type of composition used in any instance will depend upon the particular purpose envisaged.

The compositions may be in the form of dustable powders or granules comprising the active ingredient (invention compound) and a solid diluent or carrier, for example fillers such as kaolin, bentonite, kiesselguhr, dolomite, calcium carbonate, talc, powdered magnesia, Fuller's earth, gypsum, diatomaceous earth and China clay. Such granules can be performed granules suitable for application to the soil without further treatment. These granules can be made either by impregnating pellets of filler with the active ingredient or by pelleting a mixture of the active ingredient and powdered filler. Compositions for dressing seed may include an agent (for example a mineral oil) for assisting the adhesion of the composition to the seed; alternatively the active ingredient can be formulated for seed dressing purposes using an organic solvent (for example N-methylpyrrolidone, propylene glycol or dimethylformamide). The compositions may also be in the form of wettable powders of water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally controlling a wetting or emulsifying agent and then adding the mixture to water which may also contain a wetting or emulsifying agent. Suitable organic solvents are aromatic solvents such as alkylbenzenes and alkylnaphthalenes, ketones such as isophorone, cyclohexanone, and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent and including a suspending agent to stop the solid settling.

Compositions to be used as sprays may be in the form of aerosols wherein the formulation is held in a container under pressure in the presence of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium-, or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants e.g. wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preperations which remain homogeneous for a sufficient time to enable them to be applied by conventional spray equipment. The concentrates may conveniently contain up to 95% suitably 10–85%, for example 25–60%, by weight of the active ingredient. After dilution to form aqueous preparations, suitable preparations may contain varying amounts of the active ingredient depending upon the intended purpose, but an aqueous preparation containing 0.00055 or 0.01% to 10% by weight of active ingredient may be used.

The compositions of this invention may contain other compounds having biological activity, e.g. compounds having similar or complementary fungicidal activity or which plant possess plant growth regulating, herbicidal or insecticidal activity.

A fungicidal compound which may be present in the composition of the invention may be one which is capable of combating ear disease of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are carbendazim, benomyl, thiophanate-methyl, thiabendazole, fuberidazole, etridazole, dichlofluanid, cymoxanil, oxadixyl, ofurace, metalaxyl, furalaxyl, benalaxyl, fosetyl-aluminium, fenarimol, iprodione, prothiocarb, procymidone, vinclozolin, penconazole, myclobutanil, propamocarb, diniconazole, pyrazophos, ethirimol, ditalimfos, tridemorph, triforine, nuarimol, triazbutyl, guazatine, triacetate salt of 1,1'-iminodi(octamethylene)diguanidine, buthiobate, propiconazole, prochloraz, flutriafol, hexaconazole, (2RS, 5RS)-5-(2,4-dichlorophenyl)tetrahydro-5-(1H-1,2,4-triazol-1-ylmethyl)-2-furyl-2,2,2-trifluoroethyl ether, cyproconazole, terbuconazole, pyrrolnitrin, 1-[(2RS, 4RS; 2RS, 4RS)-4-bromo-2-(2,4-dichlorophenyl)tetrahydrofurfuryl] -1H-1,2,4-triazole, 5-ethyl-5,8-dihydro-8-oxo(1,3)-dioxolo ( 4,5-g)quinoline-7-carboxylic acid, (RS)-1-aminopropylphosphonic acid, 3-(2,4-dichlorophenyl)-2-(1H-1,2,4-triazol-1-yl)quinazolin-4(3H)-one, fluzilazole, triadimefon, triadimenol, diclobutrazol, fenpropimorph, pyrifenox, fenpropidin, chlorozolinate, imazalil, fenfuram, carboxin, oxycarboxin, methfuroxam, dodemorph, BAS 454, blasticidin S, kasugamycin, edifenphos, Kitazin P, cycloheximide, phthalide, probenazole, isoprothiolane, tricyclazole, 4-chloro-N-(cyano(ethoxy)methyl)benzamide, pyroquilon, chlorbenzthiazone, neoasozin, polyoxin D, validamycin A, mepronil, flutolanil, pencycuron, diclomezine, phenazin oxide, nickel dimethyldithiocarbamate, techlofthalam, bitertanol, bupirimate, etaconazole, hydroxyisoxazole, streptomycin, cyprofuram, biloxazol, quinomethionate, dimethirimol, 1-(2-cyano-2-methoxyiminoacetyl)-3-ethyl urea, fenapanil, tolclofosmethyl, pyroxyfur, polyram, maneb, mancozeb, captafol, chlorothalonil, anilazine, thiram, captan, folpet, zineb, propineb, sulphur, dinocap, dichlone, chloroneb, binapacryl, nitrothal-isopropyl, dodine, dithianon, fentin hydroxide, fentin acetate, tecnazene, quintozene, dicloran, copper containing compounds such as copper oxychloride, copper sulphate and Bordeaux mixture, and organomercury compounds.

The compounds of general formula (I) can be mixed with soil, peat or other rooting media for the protection of plants against seed-borne, soil-borne or foliar fungal diseases.

Suitable insecticides which may be incorporated in the composition of the invention include pirimicarb, dimethoate, demeton-s-methyl, formothion, carbaryl, isoprocarb, XMC, BPMC, carbofuran, carbosulfan, diazinon, fenthion, fenitrothion, phenthoate, chlorpyrifos, isoxathion, propaphos, monocrotophas, buprofezin, ethroproxyfen and cycloprothrin.

Plant growth regulating compounds are compounds which control weeds or seedhead formation, or selectively control the growth of less desirable plants (e.g. grasses).

Examples of suitable plant growth regulating compounds for use with the invention compounds are the gibberellins (e.g. $GA_3$, $GA_4$ or $GA_7$), the auxins (e.g. indoleacetic acid, indolebutyric acid, naphthoxyacetic acid or naphthylacetic acid), the cytokinins (e.g. kinetin, diphenylurea, benzimidazole, benzyladenine or benzylaminopurine), phenoxyacetic acids (e.g. 2,4-D or MCPA), substituted benzoic acid (e.g. triiodobenzoic acid), morphactins (e.g. chlorfluoroecol), maleic hydrazide, glyphosate, glyphosine, long chain fatty alcohols and acids, dikegulac, paclobutrazol, fluoridamid, mefluidide, substituted quaternary ammonium and phosphonium compounds (e.g. chloromequat chlorphonium or mepiquatchloride), ethephon, carbetamide, methyl-3,6- dichloroanisate, daminozide, asulam, abscisic acid, isopyrimol, 1-(4-chlorophenyl)-4,6-dimethyl-2-oxo-1,2-dihydropyridine-3-carboxylic acid, hydroxybenzonitriles (e.g. bromoxynil), difenzoquat, benzoylprop-ethyl 3,6-dichloropicolinic acid, fenpentezol, inabenfide, triapenthenol and tecnazene.

The following Examples illustrate the invention. Throughout the Examples, the term 'ether' refers to diethyl ether, magnesium sulphate was used to dry solutions, and solutions were concentrated under reduced pressure. Reactions involving water-sensitive intermediates were performed under an atmosphere of nitrogen and solvents were dried before use, where appropriate. Unless otherwise stated, chromatography was performed on a column of silica gel as the stationary phase. Where shown, infrared and n.m.r. data are selective; no attempt is made to list every absorption in all cases. $^1$H n.m.r. spectra were recorded using $CDCl_3$— solutions unless otherwise stated. The following abbreviations are used throughout:

| DME = | dimethoxyethane | | |
|---|---|---|---|
| THF = | tetrahydrofuran | s = | singlet |
| DMF = | N,N-dimethylformamide | d = | doublet |
| n.m.r. = | nuclear magnetic resonance | t = | triplet |
| IR = | infrared | m = | multiplet |
| m.p. = | melting point | br = | broad |
| GC = | gas chromatography | ppm = | parts per million |
| TLC = | thin layer chromatography | | |
| HPLC = | high performance liquid chromatography | | |

EXAMPLE 1

This Example illustrates the preparation of (E)-methyl 2-[2-(3-benzyloxyphenoxy)phenyl]-3 -methoxypropenoate (Compound No. 23 of Table I).

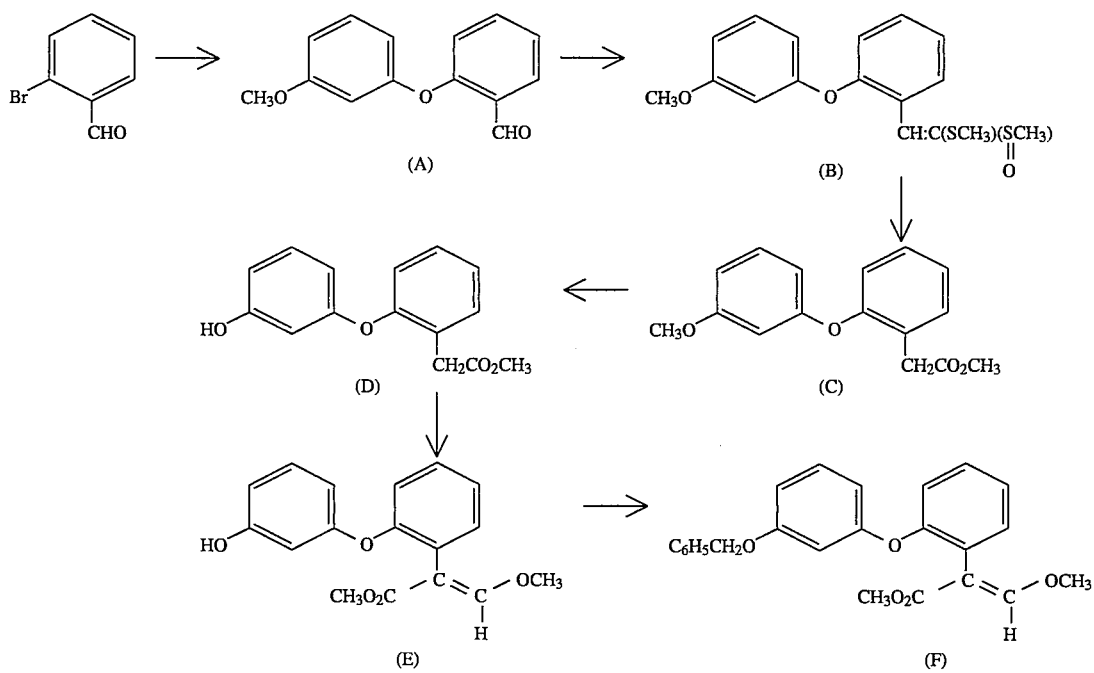

A mixture of 2-bromobenzaldehyde (100 g; 0.54 mol), ethylene glycol (67.03 g; 1.08 mol), p-toluenesulphonic acid (0.5 g) and toluene was heated to and maintained at reflux temperature for 6 hours. During this period, water/ethylene glycol (23 ml) was removed by azeotropic distillation. The mixture was cooled and ether (1 l) was added. The ether solution was washed with saturated sodium bicarbonate solution (200 ml) water (3×150 ml) and saturated brine (1×150 ml). After drying and filtration, evaporation of the ether solution gave 2-(2 -bromophenyl)-1,3-dioxolane (121.96 g, 98.6% yield) as an oil.

$^1$H n.m.r.: (60 MHz) delta: 3.4 (4H, m), 6.0 (1H, s), 6.9–7.6 (4H, m), ppm.

This material was used without further purification for the following step.

Potassium hydroxide pellets (35.2 g; 0.63 mol) were dissolved in water (50 ml) and 3-methoxyphenol (78 g; 0.63 mol) was added together with toluene (250 ml). The mixture was heated to and maintained at reflux temperature until water ceased to distil over (a total of 65 ml of water was collected). The mixture was cooled to 80° C. and 2-(2-bromophenyl)-1,3,-dioxolane (120 g; 0.524 mol), DMF (200 ml) and cuprous chloride (0.2 g) were added. The mixture was slowly heated to 150°–155° C. and toluene was distilled off. The mixture was maintained at 150°–155° C. for 6 hours then cooled to 25° C. and water (500 ml) was added. The mixture was filtered and the residue was washed with ether (200 ml ). The filtrate was extracted with ether (3×150 ml). The combined ether extracts were washed with 2N sodium hydroxide solution (2×150 ml), water (4×150 ml) and saturated brine (1×200 ml). After drying and filtration the ether solution on evaporation gave 2-[2-(3-methoxyphenoxy)phenyl]-1,3 -dioxolane (124.1 g, 87.1% yield) as an oil.

$^1$H n.m.r. (60 MHz) delta: 3.65 (3H, s), 3.95 (4H, d), 6.12 (1H, s), 6.6–7.6 (8H, m) ppm.

This material was used without further purification for the following step.

2-[2-(3-Methoxyphenoxy)phenyl]-1,3-dioxolane (32.7 g; 0.12 mol) was stirred in a mixture of water (95 ml) and concentrated hydrochloric acid (5 ml) at ambient temperature for 19 hours. The mixture was extracted with ether (2×60 ml) and the combined ether extracts were washed with saturated aqueous sodium bicarbonate solution (30 ml), water (3×30 ml) and saturated brine (30 ml). The resulting solution was dried, filtered and concentrated to give almost pure 2-(3-methoxyphenoxy)benzaldehyde (A) (26.17 g, 95.4% yield) as an oil. This material was used without purification for the following step. However, an analytical sample was prepared by chromatography using a mixture of ether and hexane as eluant to give an amber oil.

$^1$H n.m.r. (90 MHz) delta: 3.79 (3H, s), 6.58–7.97 (8H, m), 10.49 (1H, d) ppm. IR maxima (film): 1691, 1599 cm$^{-1}$.

A mixture of 2-(3-methoxyphenoxy)benzaldehyde (25.0 g, 0.109 mol), methyl methylthiomethylsulphoxide (13.64 g, 0.11 mol) benzyltrimethylammoniumhydroxide (8.0 ml of a 30% solution in methanol) and THF (150 ml), was stirred at reflux temperature for 45 minutes. The resulting solution was evaporated to dryness, and was then chromatographed using a mixture of ether and hexane as eluant to give the sulphoxide (B) (27.67 g, 75.3% yield) as an amber gum.

$^1$H n.m.r. (60 MHz) delta: 2.2 (3H, s), 2.55 (3H, s), 3.65 (3H, s), 6.35–8.15 (9H, m) ppm.

Acetyl chloride (20 ml) was added to absolute methanol (200 ml) dropwise over 15 minutes with water bath cooling to maintain the temperature at 20–25° C. A solution of the sulphoxide (B) (27.67 g; 0.083 mol) in methanol (40 ml) was added in one portion and the resulting solution was stirred at ambient temperature for 18 hours. The methanol solution was evaporated to dryness under reduced pressure to leave a brown gum (22.78 g) which was dissolved in ether (200 ml). The ether solution was washed with saturated aqueous sodium bicarbonate solution and, after filtering off a small quantity of insoluble material, the ether solution was evaporated to dryness and the residue was chromatographed using a mixture of ether and hexane as eluant to give methyl 2-(3-methoxyphenoxy)phenylacetate (C) (15.62 g, 69.3% yield) as a viscous oil.

¹H n.m.r. (60 MHz) delta: 3.5 (3H, s), 3.59 (2H, s), 3.63 (3H, s), 6.35–7.32 (8H, m) ppm.

Boron tribromide (12.89 g, 0.051 mol) was dissolved in dichloromethane (50 ml) and cooled to 0–5° C. A solution of methyl 2-(3-methoxyphenoxy)phenylacetate (7.0 g; 0.026 mol) in dichloromethane (80 ml) was added dropwise, with stirring over 1 hour. After stirring at 0°–5° C. for 20 minutes the mixture was added dropwise, with stirring to absolute methanol (100 ml) maintaining the temperature at 0°–5° C. The resulting solution was poured into water (250 ml) containing sodium bicarbonate (12 g), and the resulting mixture was extracted with ether (500 mls). The organic phase was washed with water (3×200 ml) and saturated brine (150 ml). After drying and filtration, evaporation of the ether solution gave methyl 2-(3-hydroxyphenoxy)phenylacetate (D) (6.12 g, 92.3% yield) as a brown gum. This material was suitable for use in subsequent steps without further purification. However, chromatography using mixtures of ether and hexane as eluant gave material of higher purity as a viscous golden oil which rapidly darkened on exposure to air.

In addition, methyl 2-(3-hydroxyphenoxy)phenylacetate (D) was prepared as follows:

A mixture of 2-chlorophenylacetic acid (30 g, 0.18 mol), potassium carbonate (48.6 g, 0.34 mol), and 3-methoxyphenol (43.5 g, 0.35 mol) was heated with stirring at 140° C. in the presence of a catalytic amount of copper(I) chloride. After 3 hours, GC and TLC analysis indicated the absence of the starting acid. The reaction mixture was allowed to cool (with the addition of dry DMF (5 ml) at 70° C. to prevent the mixture from becoming too viscous), poured into water and acidified with concentrated hydrochloric acid. The resulting mixture was extracted with ether and the combined ether extracts were washed with water until neutral. The ether extracts were dried and evaporated to afford a mixture of 3-methoxyphenol (49%) and 2-(3-methoxyphenoxy)phenylacetic acid (41%) as a brown mobile oil which was used in the next stage without further purification.

The brown oil was refluxed in methanol (70 ml) containing concentrated sulphuric acid (2 ml) for 2½ hours. The reaction mixture was allowed to cool to room temperature and was then poured into water. The resulting mixture was extracted (×2) with ether and the combined ether extracts were washed with dilute aqueous sodium hydroxide solution, and then with water until neutral and then dried. Evaporation gave crude methyl 2-(3-methoxyphenoxy)phenylacetate (34.9 g) as an orange-brown oil (86% pure by GC). The crude product was combined with another batch (8.2 g) which had been prepared by the same method. Repeated short-path distillation (50°–120° C. at 4×10⁻² mbar) then afforded methyl 2-(3-methoxyphenoxy)phenylacetate as an oil (37.1 g, 95% pure, ca. 60% yield from 2-chlorophenylacetic acid). Further amounts of product were obtained in subsequent preparations.

Methyl 2-(3-methoxyphenoxy)phenylacetate (97 g, 0.36 mol) was heated with concentrated hydrobromic acid (194 ml) in acetic acid (150 ml) at 110° C. for 8 hours. After standing at room temperature overnight, more concentrated hydrobromic acid (100 ml) was added and the reaction mixture was reheated to 110° C. After a further 7 hours, all of the starting material had been consumed. The reaction mixture was allowed to cool to room temperature, poured into brine and then extracted with dichloromethane (×2). The dichloromethane was evaporated to give an oil which was heated at 70° C. with methanol (400 ml) and concentrated sulphuric acid (2 ml) for 2 hours. The reaction mixture was allowed to cool to room temperature, poured into brine and extracted with dichloromethane (×2). The combined extracts were washed with water (until neutral) and then dried, filtered and evaporated to give a brown oil (92.8 g). Short-path distillation (150° C., 1×10⁻³ mbar) of a portion (72.8 g) afforded methyl 2-(3-hydroxyphenoxy)phenylacetate (D) (41.4 g, 57% yield from methyl 2-(3-methoxyphenoxy)phenylacetate) as a golden syrup.

¹H n.m.r. (60 MHz) delta: 3.57 (3H, s), 3.63 (2H, s), 5.82 5.82 (1H, s), 6.4–7.35 (8H, m) ppm. IR maxima (film): 3408, 1713 cm⁻¹.

To a suspension of sodium hydride (0.558 g, 0.023 moles in DMF (20 ml) was added dropwise a solution of methyl 2-(3-hydroxyphenoxy)phenylacetate (D) (2.0 g; 0.0077 mol) in DMF (10 ml) and methylformate (10 g; 0.167 mol) After stirring for 45 minutes, water (100 mls) was added and the mixture was extracted with ether (50 mls). The aqueous layer was acidified with hydrochloric acid to pH 3–4 and the mixture was extracted with ether (2×40 mls). The combined ether extracts were washed with water (3×30 mls) and saturated brine (1×30 ml), and then dried. The ether was evaporated off and the residue was dissolved in DMF (20 ml), and anhydrous potassium carbonate. (0.64 g; 0.0046 moles) and dimethyl sulphate (0.55 g; 0.0044 moles) was added. The mixture was stirred at ambient temperature for 1 hour, then water (100 ml) was added, and the mixture was extracted with ether (2×40 ml). The combined ether extracts were washed with water (3×20 ml) and saturated brine (20 ml), dried, filtered, evaporate to dryness, then chromatographed using a mixture of ether and hexane as eluant to give (E)-methyl 2-[2-(3-hydroxyphenoxy)phenyl]-3-methoxypropenoate (E) as an amber gum which, on trituration with a mixture of hexane and dichloromethane, gave a white solid, [0.7 g, 30% yield from methyl 2-(3-hydroxyphenoxy)phenylacetate (D)] m.p. 115°–116° C.

In addition, (E)-methyl 2-[2-(3-hydroxyphenoxy)phenyl] -3-methoxypropenoate (E) was prepared as follows:

A solution of methyl 2-(3-hydroxyphenoxy)phenylacetate (D) (12 g, 0.0465 mol) and methyl formate (55.8 g, 0.93 mol) in dry DMF (35 ml) was added dropwise over 45 minutes to a stirred suspension of sodium hydride (6.696 g of a 50% dispersionin oil, 0.1395 mol, pre-washed with 40–60 petroleum ether) in dry DMF (65 ml). The reaction mixture was stirred at room temperature for 2½ hours, poured into water (200 ml), acidified to pH3 with concentrated hydrochloric acid and then extracted with ether (2× 200 ml). The combined organic extracts were washed with brine (2×200 ml), dried, filtered and evaporated to give a yellow oil (12.5 g, 0.0433 mol). The oil (12.5 g, 0.0433 mol) was dissolved in dry DMF (100 ml) and potassium carbonate (5.98 g, 0.0433 mol) was added. After stirring for 10 minutes, a solution of dimethyl sulphate (5.19 g, 0.042 mol) in DMF (10 ml) was added in one portion. The resulting mixture was stirred at room temperature overnight, poured into water (200 ml) and extracted with ether (2×200 ml). The combined ether extracts were washed with brine (3×200 ml), dried, filtered and evaporated to give a sticky gum. Crystallisation from dichloromethane-hexane gave (E)-methyl 2-[2-(3-hydroxyphenoxy)phenyl]-3-methoxypropenoate (E) (9.54 g, 73%), m.p. 117°–118° C.

¹H n.m.r. (90 MHz) delta: 3.58 (3H, s), 3.75 (3H, s), 5.38 (1H, s), 6.39–7.33 (8H, m), 7.4 (1H, s) ppm. IR maxima (nujol): 3295, 1672, 1630 cm⁻¹.

A mixture of (E)-methyl 2-[2-(3-hydroxyphenoxy)phenyl] -3-methoxypropenoate (1.0 g; 0.0033 mol), benzyl bromide (0.57 g; 0.0033 mol) potassium carbonate (0.8 g; 0.0053 mol) and dry DMF (15 ml) was stirred at ambient temperature for 3 hours. Water (50 ml) was added and the mixture was extracted with ether (2×30 ml). The combined organic extracts were washed with water (2×20 ml) and after drying and filtration the ether solution was evaporated to dryness then chromatographed using a mixture of ether and hexane as eluant to give the title compound (F) as a colourless gum (1.11 g, 85% yield).

$^1$H n.m.r. (90 MHz) delta: 3.55 (3H, s), 3.7 (3H, s), 4.97 (2H, s), 6.5–7.32 (13H, m), 7.44 (1H, s) ppm. IR maxima (film): 1710, 1638 cm$^{-1}$.

EXAMPLE 2

This Example illustrates the preparation of (E)-methyl 3-methoxy-2-[2-(3-phenylsulphonyloxyphenoxy)phenyl] propenoate (Compound No. 51 of Table I).

A mixture of (E)-methyl 2-[2-(3-hydroxyphenoxy)phenyl] -3-methoxypropenoate (0.5; 0.00166 moles, prepared as described in Example 1), benzenesulphonylchloride (0.36 g; 0.002 mol) and pyridine (10 ml), was stirred at 60°–70° C. for 3 hours. The mixture was cooled to 25° C., water (60 ml) was added and the mixture was extracted with ether (2×30 ml). The combined ether extracts were washed with water (20 ml), dilute hydrochloric acid (20 mls), water (93×200 ml) and saturated brine (20 ml). The ether solution was dried, filtered, concentrated and chromatographed using a mixture of chloroform and hexane as eluant to give the title compound (0.21 g, 28.7% yield) as a colourless gum.

$^1$H n.m.r. (90 MHz) delta: 3.56 (3H, s0, 3.75 (3H, s), 6.52–7.96 (13H, m), 7.40 (1H, s) ppm.

EXAMPLE 3

This Example illustrates the preparation of (E)-methyl 3-methoxy-2-(2-[3-(4-nitrophenoxy)phenoxy]phenyl)propenoate (Compound No. 133 of Table I).

A mixture of E-methyl 2-[2-(3-hydroxyphenoxy)phenyl] -3-methoxypropenoate (1.2 g; 0.004 mol, prepared as described in Example 1), 4-nitrofluorobenzene (0.68 g; 0.008 mol), potassium carbonate (1.1 g; 0.008 mol) and DMF (15 ml) was stirred at ambient temperature for 16 hours then poured into water (80 mls) and extracted with ether (2×30 ml). The combined organic extracts were washed with water (3×25 ml) and then saturated brine (25 ml). They were then dried, filtered, concentrated and chromatographed using a mixture of chloroform and hexane as eluant to give the title compound as an amber-coloured gum (0.93 g, 55.2% yield).

$^1$H NMR (90 MHz) delta: 3.55 (3H, s), 3.72 (3H, s), 6.67–8.41 (12H, m), 7.44 (1H, s) ppm.

EXAMPLE 4

This Example illustrates the preparation of (E)-methyl 2-(2-[3-(4-fluorophenoxy)phenoxy]phenyl)-3 -methoxypropenoate (Compound No. 124 of Table I).

A mixture of (E)-methyl 2-[2-(3-(hydroxyphenoxy)phenyl] -3-methoxypropenoate (1.0 g, 0.0033 mols, prepared as described in Example 1), bis(4-fluorophenyl)iodonium bromide (2.63 g; 0.0069 mol), triethylamine (0.5 ml), copper powder (0.5 g) and absolute methanol (15 ml) was heated at reflux for 6 hours. Further bis(4-fluorophenyl)iodonium bromide (1 g; 0.0069 mol) was added and the mixture was stirred at reflux temperature for a further 3 hours. After cooling and filtration, water (80 ml) was added to the filtrate and the mixture was extracted with ether (2×30 ml). The combined ether extracts were washed with water (3×15 ml) and saturated brine (15 ml). After drying and filtration the ether solution was concentrated to give the title compound as an amber gum (0.16 g, 12.3% yield).

$^1$H n.m.r. (60 MHz) delta: 3.42 (3H, s), 3.51 (3H, s), 6.35–7.30 (12H, m), 7.35 (1H, s) ppm. IR maxima (film): 1710, 1641 cm$^{-1}$.

EXAMPLE 5

This Example illustrates the preparation of (E)-methyl 2-[2-(3-benzoyloxyphenoxy)phenyl]3-methoxypropenoate (Compound No. 49 of Table I).

A mixture of (E)-methyl 2-[2-(3-hydroxyphenoxy)phenyl] -3-methoxypropenoate (0.5 g, 0.00166 mol, prepared as described in Example 1, benzoyl chloride (0.26 g; 0.00185 mol), potassium carbonate (0.23 g; 0.00166 mol) and DMF (10 ml) was stirred at ambient temperature for 1½ hours. Further benzoyl chloride (0.26; 0.00166 mol) and potassium carbonate (0.23 g; 0.00166 mol) were added and the mixture was stirred at ambient temperature for 16 hours. Water (80 ml) was added and the mixture was extracted with ether (2×40 ml). The combined ether extracts were washed with water (3×20 ml) and saturated brine (20 ml), then dried, filtered, concentrated and chromatographed using a mixture of ether and hexane as eluant to give a white solid. Recrystallisation from aqueous methanol gave the pure title compound (0.32 g, 47.7% yield) as a white solid, m.p. 94°–95° C.

$^1$H n.m.r. (90 MHz) delta: 3.62 (3H, s); 3.74 (3H, s), 6.76–8.38 (13H, m), 7.46 (1H, s) ppm. IR maxima (nujol): 1741, 1698, 1627 cm$^{-1}$.

EXAMPLE 6

This Example illustrates the preparation of (E,E)-methyl 2-[2-(3-[4-chlorophenylazo]-4-hydroxyphenoxy)-phenyl] -3-methoxypropenoate (Compound No. 282 of Table I).

1M Hydrochloric acid (2.5 ml) was added to 3 -chloroaniline hydrochloride (6.64 ml of 0.25M aqueous solution) and the mixture was cooled to below 10° C. Sodium nitrite (3.32 ml of 0.5M aqueous solution) was added dropwise and the resulting mixture was stirred at below 10° C. for 10 minutes. The resulting solution of 3 -chlorobenzenediazonium chloride was added dropwise with stirring to a mixture of (E)-methyl 2-[2-(4-hydroxyphenoxy)phenyl] -3-methoxypropenoate (0.5 g, 0.00166 mol, prepared by a route analogous to that described in Example 1 for the preparation of the corresponding 3-hydroxy-compound) in sodium hydroxide (16.6 ml of 0.1M aqueous solution), and acetone (30 ml). Further aqueous sodium hydroxide solution was added simultaneously to maintain the pH between 8–10 and the temperature was maintained below 10° C. After stirring for 20 minutes the mixture was extracted with ether (2×40 ml). The combined ether extracts were washed with water (3×15 ml) and saturated brine (15 ml), then dried, filtered, concentrated, and chromatographed using a mixture of ether and hexane as eluant to give an orange solid. Recrystallisation from a mixture of hexane and dichloromethane gave the pure title compound (99.3 mg, 13.6% yield), m.p. 143°–144° C.

EXAMPLE 7

This Example illustrates the preparation of (E)-methyl 2-[2-(3-[3-methoxyphenoxy]phenoxy)phenyl]-3 -methoxypropenoate (Compound No. 129 of Table I).

To a stirred solution of sodium (0.61 g) in methanol (10 ml) was added resorcinol (4.34 g) in one portion. After stirring the resulting mixture for ½ hour at room temperature, the excess methanol was removed under reduced pressure. To the resulting orange oil was added pyridine (6.6 mls), 3-bromoanisole (14.74 g) and cuprous chloride (192 mg). The mixture was stirred at 125° C. for 66 hours. The reaction mixture was allowed to cool and was then poured into dilute hydrochloric acid and extracted with ether. The ether extracts were re-extracted with dilute aqueous sodium hydroxide and these aqueous extracts were acidified with dilute hydrochloric acid and extracted with ether. These ether extracts were washed successively with water and brine, then dried and concentrated to give 3.72 g of a red oil. Bulb-to-bulb distillation of this oil (170° C. oven temp./0.05 mmHg) gave 3-(3-methoxyphenoxy)phenol (1.71 g) as a thick pale yellow oil.

$^1$H n.m.r. delta: 3.78 (3H, s), 4.93 (1H, s) ppm.

To a stirred solution of sodium (0.18 g) in methanol (4 ml) was added 3-(3-methoxyphenoxy)phenol (1.70 g) in one portion. After stirring the resulting mixture for ½ hour at room temperature the excess methanol was removed under reduced pressure. To the resulting orange oil was added o-bromophenylacetic acid (0.85 g) and cuprous chloride (40mg), and the reaction mixture was stirred at 130° C. for 1 hour. Further o-bromophenylacetic acid (0.4 g) and sodium ethoxide (0.13 g) were added and the mixture was stirred at 130° C. for a further 3 hours, allowed to cool, then acidified with dilute hydrochloric acid and extracted with ether. The ether extracts were washed successively with water and brine, then dried and concentrated to give 3.12 g of a red oil containing 2-[3-(3-methoxyphenoxy)phenoxy] phenylacetic acid. To this crude acid (3.12 g) was added methanol (40 ml) and 3 drops of concentrated sulphuric acid. This reaction mixture was stirred at 90° C. for 1 hour, then allowed to cool, poured into water and extracted with ether. The ether extracts were washed successively with dilute aqueous sodium hydroxide, water and brine, then dried and concentrated to give 1.33 g of a yellow oil. Bulb-to-bulb distillation of this oil (160° C. oven temp./0.07 mmHg) gave methyl 2-[3-(3 -methoxyphenoxy)phenoxy]phenylacetate [1.03 g, 36% yield from 3-(3-methoxyphenoxy)phenol].

$^1$H N.m.r. delta: 3.62 (3H, s), 3.68 (2H, s), 3.78 (3H, s) ppm.

A mixture of methyl 2-[3-(3-methoxyphenoxy)phenoxy] phenylacetate (1.00 g) and methyl formate (3.34 ml) in DMF (1 ml) was added dropwise over 10 minutes to a stirred suspension of sodium hydride (0.13 g) in DMF (10 mls) cooled in ice to below 10° C. (effervescence). Following the addition, the reaction mixture was stirred at room temperature for 2 hours, poured into water, acidified with dilute hydrochloric acid, and then extracted with ether. The extracts were washed with water, dried and concentrated to give a yellow oil (1.09 g). Potassium carbonate (0.76 g) and dimethyl sulphate (0.33 g) were added successively to a stirred solution of this yellow oil in DMF (20 ml) and the resulting mixture was stirred at room temperature for 2½ hours, poured into water and then extracted with ether. The extracts were washed with water, dried, concentrated and chromatographed using a 1:1 mixture of ether and petrol as eluant to give the title compound [61 g, 55% yield from methyl 2-[3-(3 -methoxyphenoxy)-phenoxy]phenylacetate] as a colourless viscous oil.

$^1$H n.m.r. delta: 3.60 (3H, s), 3.75 (3H, s), 3.78 (3H,s) 6.55–6.72 (5H, m), 6.97 (1H, d), 7.10–7.30 (6H, m), 7.48 (1H, s) ppm. IR maxima (nujol) 1713, 1638 cm$^{-1}$.

EXAMPLE 8

This Example illustrates the preparation of (E)-methyl 3-methoxy-2-[2-(3-[phenoxymethyl]phenoxy)phenyl]propenoate (Compound No. 21 of Table I).

(E)-methyl 3-methoxy-2-[2-(3-methylphenoxy)phenyl] propenoate (0.50 g, prepared from 3-methylphenol and 2 -bromobenzaldehyde by the method described in Example 1) and N-bromosuccinimide (0.30 g) were refluxed in carbon tetrachloride (25 mls) with a trace of azobisisobutyronitrile (AIBN), for 4.5 hours, with further traces of AIBN being added at intervals of 1.5 hours. The reaction was monitored by GC. After standing at room temperature overnight a further trace of AIBN was added to the reaction mixture and refluxing was continued until GC analysis showed almost complete disappearance of the starting material (1 hour). The reaction mixture was filtered through celite, washed with water and evaporated to give a pale yellow gum (0.69 g). GC and NMR analysis showed that this gum consisted of (E)-methyl 2-[2-(3 -bromomethylphenoxy)phenyl]-3-methoxypropenoate (80%), the corresponding dibromomethyl compound (11%) and unreacted propenoate starting material (8%).

$^1$H n.m.r. data for the major component: delta 3.61 (3H, s), 3.77 (3H, s), 4.42 (2H, s), 6.90–7.40 (8H, m), 7.48 (1H, s), ppm.

This material was carried through without further purification.

Part of the crude material (0.42 g, 80% pure), was stirred with phenol (0.105 g) and potassium carbonate (0.077 g) in DMF (20 ml), and heated to 60° C. for 1 hour. After standing overnight at room temperature the mixture was heated to 60° C. for a further 1 hour, cooled, poured into water, and extracted with ethyl acetate. The organic fraction was washed with water, dried and evaporated to yield a pale yellow oil (0.42 g). Attempted purification by high performance liquid chromatography, eluting with a 3:1 mixture of petrol and ethyl acetate, gave the title compound (0.13 g) as a colourless gum containing as an impurity 20% of (E)-methyl 2-[2-(3-dibromomethylphenoxy)phenyl] -3-methoxypropenoate.

$^1$H n.m.r. data for the title compound: delta 3.58 (3H, 3.70 (3H, s), 4.98 (2H, s), 6.88–7.36 s), (13H, m), 7.46 (1H, s) ppm.

EXAMPLE 9

This Example illustrates the preparation of (E)-methyl 2-[2-(2-acetyl-5-phenoxyphenoxy)phenyl]-3-methoxypropenoate and (E)-methyl 2-[2-(4-acetyl-3-phenoxyphenoxy)phenyl] -3-methoxypropenoate (Compound Nos. 366 and 365 respectively of Table I).

Methyl 2-(3-phenoxyphenoxy)phenylacetate was prepared from 3-phenoxyphenol and 2-bromobenzaldehyde by the steps described in Example 1 for the preparation of methyl 2-(3 -methoxyphenoxy)phenylacetate. This was the converted into (E)-methyl 3-methoxy-2-[2-(3-phenoxyphenoxy) phenyl]propenoate [$^1$H n.m.r (250 MHz) 3.61 (3H, s), 3.78 (3H, s), 6.68–7.35 (13H, m), 7.48 (1H, s) ppm] using sodium hydride and methyl formate, and then potassium carbonate and dimethyl sulphate, using the procedure described in Example 1 for the preparation of (E)-methyl 2-[2-(3 -hydroxyphenoxy)phenyl]-3-methoxypropenoate, except that just 2 equivalents of sodium hydride were used in this case.

Powdered aluminium chloride (0.512 g, 3.84 mmol) was added to a stirred solution of (E)-methyl 3-methoxy-2-[2-(3-phenoxyphenoxy)phenyl]propenoate (0.722 g, 1.92 mmol) in dry dichloromethane (20 ml) at 0°–5° C. A solution of acetyl chloride (0.151 g, 1.92 mmol) in dry dichloromethane (3 ml) was then added dropwise over 10 minutes and the resulting mixture was stirred overnight, being allowed to warm to ambient temperature. The reaction mixture was diluted with ether (125 ml) and washed with 2N hydrochloric acid (×2), 10% aqueous sodium carbonate solution and finally with water. The residue obtained after removal of the solent was purified by flash chromatography using a mixture of ether and petrol as eluant to give an approximately 3:1 mixture of the two title compounds (individual identities not assigned) as a colourless gum (0.424 g). Part of this gum (0.400 g) was separated by high performance liquid chromatography on silica gel using a 70:25:5 mixture of hexane:dichloromethane:methyl t-butyl ether as eluant to give (i) Regioisomer A (0.179 g), eluted first, major component of the mixture, as a white crystalline solid, m.p. 90°–92° C.

$^1$H n.m.r. (250 MHz): delta 2.52 (3H, s), 3.56 (3H, s), 3.72 (3H, s), 6.48 (1H, d), 6.64 (1H, q), 6.9–7.4 (9H, m), 7.43 (1H, s), 7.84 (1H, d) ppm.

and (ii) Regioisomer B (0.061 g, containing ca. 5% of regioisomer A), eluted second, minor component of the mixture, as a white crystalline solid, m.p. 82°–85° C.

$^1$H n.m.r (250 MHz): delta 2.51 (3H, s), 3.60 (3H, s), 3.75 (3H, s), 6.45 (1H, d), 6.59 (1H, q), 6.9–7.4 (9H, m), 7.48 (1H, s), 7.82 (1H, d) ppm.

EXAMPLE 10

This Example illustrates the preparation of (E)-methyl 3-methoxy-2-[2-(3-pyrimidin-2-yloxyphenoxy)phenyl]propenoate (Compound No. 22 of Table II).

A mixture of (E)-Methyl 2-[2-(3-hydroxyphenoxy)phenyl] -3-methoxypropenoate (0.5 g, prepared as described in Example 1), potassium carbonate (0.46 g), 2-chloropyrimidine (0.23 g) and cuprous chloride (0.01 g) in DMF (0.01 g) in DMF (15 ml) was heated under reflux for 4 hours. After cooling, the mixture was poured into water and filtered. The filtrate was extracted with ether. The combined ether extracts were washed successively with water and brine, dried, concentrated and chromatographed using a mixture of ether and hexane as eluant to give the title compound as a gum (0.26 g, 41% yield).

IR (film): 1707, 1633 cm$^{-1}$. $^1$H n.m.r. (90 MHz): delta 3.54 (3H, s), 3.68 (3H, s), 6.74–7.34 (9H, m), 7.38 (1H, s), 8.28 (2H, d) ppm.

EXAMPLE 11

This Example describes the preparation of (E)-methyl 3-methoxy-2-[2-(3-phenoxyphenylthio)phenyl]propenoate (Compound No. 446 of Table III):

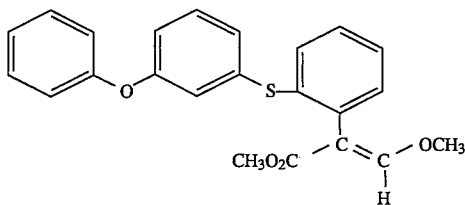

2-Mercaptophenylacetic acid was prepared by a method described in the chemical literature (see D. Papa et al, *J. Org. Chem.*, 1949, 24, 723, R. H. Glauert and F. G. Mann, *J. Chem. Soc.*, 1952, 2127 and references therein). 2-Mercaptophenylacetic acid (1.68 g) was added to a stirred solution of sodium hydroxide (0.8 g) in methanol (10 ml), (compare D. C. Atkinson et al, *J. Med. Chem.*, 1983, 26, 1361). The resulting orange solution was stirred at room temperature for 90 minutes then concentrated under reduced pressure, removing the final residues of methanol by azeotroping with toluene, to leave a yellow solid. Cuprous chloride (0.2 g) and a solution of 3-phenoxybromobenzene (2.49 g, prepared from 3-phenoxyphenol and triphenylphosphine dibromide by the method described by J. P. Schaefer et al, *Org. Synth., Coll.* Vol.5, 142) in DMF (10 ml) were added successively to a stirred solution of this yellow solid in DMF (20 ml). The resulting mixture was heated at 95° C. for 1½ hours, at 125° C. for 2 hours, and then at reflux for a further 2 hours. After cooling, the reaction mixture was poured into aqueous sodium hydroxide then washed with ether (×3). The aqueous solution was acidified with concentrated hydrochloric acid and extracted with ether (×3). These extracts were washed with water, dried and concentrated to give a purple oil (2.2 g) consisting mainly of 2-(3-phenoxyphenylthio)phenylacetic acid. A solution of this oil in methanol (20 ml) was added to acidic methanol [prepared by carefully treating methanol (30 ml) with acetyl chloride (3.5 ml)] and the resulting mixture was stirred for 90 minutes at room temperature. The reaction mixture was concentrated and the residue was partitioned between ether and aqueous sodium bicarbonate. The organic layer was separated and washed successively with aqueous sodium hydroxide (×2) and water (×3) then dried and concentrated to give crude methyl 2-(3-phenoxyphenylthio)phenylacetate (2.06 g) as a purple oil.

IR maximum (film): 1740 cm$^{-1}$, 94% pure by GC.

The crude methyl 2-(3-phenoxyphenylthio)phenylacetate was converted into the title compound in a yield of 53% by the 2 steps described in Example 7 for the conversion of methyl 2-[3-(3-methoxyphenoxy)phenoxy]phenylacetate into (E)-methyl 2-[2-(3-[3-methoxyphenoxy]phenoxy)phenyl]-3 -methoxypropenoate, that is by formulation with methyl formate and sodium hydride, followed by O-methylation with dimethyl sulphate and potassium carbonate. The product was an orange gum, 98% pure by GC, which crystallised on standing.

m.p. 48°–51.5° C. IR maxima (film): 1710 and 1632 cm$^{-1}$. $^1$H n.m.r. (270 MHz): delta 3.62 (3H, s), 3.73 (3H, s), 6.78 (1H, dd), 6.88–7.00 (4H, m), 7.05–7.36 (7H, m), 7.42 (1H, d), 7.48 (1H, s) ppm.

EXAMPLE 12

This example illustrates the preparation of (E)-methyl 2-[2-(3-pyrimidin-2-yloxyphenylthio)phenyl]-3 -methoxypropenoate (compound No 22 of Table IV).

A mixture of the sodium salt of 3-methoxythiophenol [prepared by treatment of 3-methoxythiophenol (2.8 g) with sodium hydroxide (0.8 g) in methanol (20 ml) followed by evaporation to dryness], 2-bromophenylacetic acid (4.3 g) and copper(I) chloride (0.4 g) in dry DMF (25 ml) was heated overnight at reflux. The reaction mixture was cooled, poured into water and acidified with dilute hydrochloric acid. The aqueous mixture was extracted with ether (×3) and the combined ether extracts were extracted in turn with dilute sodium hydroxide solution (×2). The combined aqueous hydroxide extracts were acidified with dilute hydrochloric acid and re-extracted with ether (×3). These combined ether extracts were washed with water (×3), dried and evaporated to give an orange oil (3.5 g, 96.8% by GC). The oil was treated with acidic methanol overnight at room temperature. Normal work-up afforded methyl 2-(3-methoxyphenylthio)phenylacetate (2.9 g, 91% by GC) as a yellow liquid which was used in the next stage without further purification.

$^1$H n.m.r. delta: 3.64 (3H, s), 3.74 (3H, s), 3.86 (2H, s) ppm. IR maxima (film): 1739 cm$^{-1}$ Methyl 2-(3-methoxyphenylthio)phenylacetate (0.86 g) and pyridinium hydrochloride (2.08 g, excess) were heated together at 200° C. under an atmosphere of nitrogen. After 3 hours, the reaction mixture was cooled and then partitioned between dilute hydrochloric acid and ethyl acetate. The acidic aqueous layer was extracted further (×2) with ethyl acetate and the combined organic layers were extracted with dilute sodium hydroxide (×3). The combined basic layers were acidified with concentrated hydrochloric acid and then extracted (×3) with ethyl acetate. These organic extracts were combined and washed with water (×3), dried and evaporated to give an off-white solid (0.64 g). The off-white solid was treated with methanolic hydrogen chloride to afford after standard work-up conditions methyl 2-(3-hydroxyphenylthio)phenylacetate (0.44 g) as a red oil (90.5% pure by GC) which was used in the next stage without further purification.

IR max.: 3384, 1738 cm$^{-1}$.

A solution of crude methyl 2-(3-hydroxyphenylthio)phenylacetate (0.44 g) and methyl formate (1.92 ml) in dry DMF (2 ml) was added dropwise to a stirred suspension of sodium hydride (0.21 g, 55% dispersion in oil, pre-washed with petroleum ether) in dry DMF (3 ml) at 0–5° C. After a total of 15 minutes, the temperature was allowed to rise to room temperature. After 2½ hours, the reaction mixture was poured into water, acidified with concentrated hydrochloric acid, and then extracted with ether (×3). The combined ether extracts were washed with water (×3), dried and evaporated to give a red gum (0.49 g). The red gum was dissolved in DMF (5 ml) and cooled to 0° C. Potassium carbonate (0.132 g) was added followed by the dropwise addition of a solution of dimethyl sulphate (0.111 g) in DMF. After stirring for 4½ hours, the reaction mixture was poured into water, and extracted with ether (×3). The combined ether extracts were washed with water (×3), dried and evaporated to give methyl 2-[2-(3-hydroxyphenylthio)phenyl]3-methoxypropenoate (0.45 g) as a red gum;

IR maxima 3240, 1709, 1665 cm$^{-1}$; M$^+$316 $^1$H n.m.r. delta: 3.65 (3H, s); 3.76 (3H, s), 7.47 (1H, s) ppm.

Crude (E)-methyl 2-[2-(3-hydroxyphenylthio)phenyl]3-methoxypropenoate (0.4 g) was treated with 2-chloropyrimidine (0.45 g) and potassium carbonate (0.17 g) in dry DMF (10 ml) at 80°–90° C. under nitrogen. After 4½ hours, GC analysis indicated complete formation of a single product. The reaction mixture was cooled, poured into water and then extracted with ether (×4). The combined yellow ether extracts were washed with water (×2), dried and evaporated to give an orange gum (0.39 g). Chromatography (eluant ether) afforded the title compound as an orange viscous gum (0.34 g);

IR maxima 1706, 1632cm$^{-1}$; $^1$H n.m.r. delta: 3.64 (3H, s),3.75 (3H, s); 6.97–7.06 (3H, m), 7.08–7.12 (1H, d), 7.25–7.35 (4H, m), 7.46–7.48 7.48 (1H, d), 7.49 (1H, s); 8.53–8.56 (2H, d) ppm.

EXAMPLE 13

This Example illustrates the preparation of (E)-methyl 2-[2-(3-phenylthiophenoxy)phenyl]-3-methoxypropenoate (Compound No 1 of Table I).

3-Hydroxydiphenylsulphide (2.02 g; 0.01 mol), (E)-methyl 2-(2-bromophenyl)-3-methoxypropenoate (1.35 g; 0.005 mol, prepared from methyl o-bromophenyl acetate, methyl formate and sodium hydride then potassium carbonate and dimethyl sulphate in the 2 steps described in Example 7 for a similar transformation), anhydrous potassium carbonate (0.69 g; 0.005 mol), and a catalytic quantity of cuprous chloride, were mixed and heated to 175° C. with stirring. After 10 hours, the mixture was cooled to ambient temperature and dissolved in DMF (50 ml). The solution thus obtained was poured into water (100 ml) and the resultant emulsion was extracted with ether (2×100 ml). The combined ether extracts were washed sequentially with water (2×100 ml), 2M sodium hydroxide solution (2×100 ml), and water (2×100 ml). The resulting ether solution was dried, filtered, and evaporated to dryness under reduced pressure. Chromatography using hexane and chloroform as eluants gave the title compound (0.83 g) as a viscous oil.

$^1$H n.m.r. (60 MHz) delta: 3.52 (3H, s), 3.64 (3H, s), 6.5–7.3 (13H, m), 7.42 (1H, s) ppm.

EXAMPLE 14

This Example illustrates the preparation of (E)-Methyl 2-[2-(3-phenylthiophenoxy)phenyl]-3 -methoxypropenoate-S,S-dioxide (compound No 3 of Table I).

3-Hydroxydiphenylsulphone (3.66 g; 0. 0156 mol), (E)-methyl 2-(2-bromophenyl)-3-methoxypropenoate (1.5 g; 0.0055 mol, prepared as described in Example 13), and anhydrous potassium carbonate (1.1 g; 0.0079 mol), were mixed with catalytic quantities of cuprous chloride and copper bronze. The mixture was heated to 170° C. under nitrogen for ten hours. After the melt had cooled to ambient temperature, the residue was dissolved in DMF (50 ml). The resultant solution was diluted with ether (100 ml), and the solution was filtered to remove inorganic salts. The solution was washed sequentially with water (100 ml), 2M sodium hydroxide solution (2×100 ml), water (100 ml), and saturated brine (100 ml). The ether solution was dried, filtered, and evaporated to dryness under reduced pressure. Chromatography of the residue using hexane and chloroform as eluants gave the title compound (0.66 g).

$^1$H n.m.r. (60 MHz) delta: 3.46 (3H, s), 3.57 (3H, s), 6.6–8.0 (14H, m) ppm.

EXAMPLE 15

This Example illustrates the preparation of (E)-methyl-2-[2-(3-anilinophenoxy)phenyl]-3-methoxypropenoate (Compound No. 4 of Table I).

3-Hydroxydiphenylamine (1.365 g; 0.0074 mol), (E)-methyl 2-(2-bromophenyl)-3-methoxypropenoate (1 g;

0.0037 mol, prepared as described in Example 13), and anhydrous potassium carbonate (0.517 g; 0.0037 mol), were combined with catalytic quantities of cuprous chloride and copper bronze. The mixture was heated to 170° C. for nine hours, and then cooled and dissolved in DMF (20 ml). This solution was then partitioned between ether and water. The ether layer was washed with water (2×100 ml), then with 1M sodium hydroxide solution (2×100 ml). The ether solution was then dried, filtered, and evaporated to dryness under reduced pressure. The residual gum was purified by chromatography using hexane and dichloromethane as eluants, to give the title compound (0.40 g).

$^1$H n.m.r. (60 MHz) delta: 3.57 (3H, s), 3.67 (3H, s), 5.75 (1H, brs), 6.3–7.4 (13H, m), 7.44 (1H, s) ppm.

EXAMPLE 16

This Example illustrates the preparation of (E)-methyl 2-[2-(3-N-methylanilinophenoxy)phenyl]-3-methoxypropenoate (Compound No 5 of Table I).

Sodium hydride (300 mg of an 80% dispersion in oil; 0.01 mol) was washed oil-free with hexane (2×50 ml). The hydride was then suspended in dry DMF (10 ml). To this suspension was added a solution of (E)-methyl 2-[2-(3-anilinophenoxy)phenyl]-3-methoxypropenoate (290 mg, prepared as described in Example 15) in dry DMF (10 ml), at such a rate as to maintain a steady effervescence. When effervescence had ceased, the mixture was stirred for a further 15 minutes and then iodomethane (2 ml; large excess) was added over a period of 5 minutes. Stirring was continued for a further 30 minutes before the suspension was cautiously diluted with water (50 ml). The aqueous emulsion was extracted with ether (2×50 ml). These ether extracts were washed with water (2×50 ml), dried, filtered, and evaporated to dryness under reduced pressure to give the title compound as a viscous oil (211 mg).

$^1$H NMR (60 MHz) delta: 3.20 (3H, s), 3.54 (3H, s), 3.65 (3H, s), 6.3–7.4 (13H, m), 7.44 (1H, s) ppm.

EXAMPLE 17

This Example illustrates the preparation of (E)-methyl 3-methoxy-2-(2-[3-(alpha-hydroxybenzyl)phenoxy]phenyl) propenoate (Compound No. 380 of Table I).

3-Hydroxybenzyl alcohol (31.0 g) was ground finely and stirred with potassium carbonate (34.6 g), 2-bromophenylacetic acid (26.9 g) and cuprous chloride (large spatula full) under nitrogen. The mixture was warmed to 140° C., and stirred vigorously for 3½ hours. DMF (60 ml) was then added to the stirred melt and the solution was allowed to cool, poured into water and acidified with dilute hydrochloric acid. The aqueous layer was extracted with ether, and the ether extracts were washed with water, dried and evaporated to give 2-(3-hydroxymethylphenoxy)phenylacetic acid as a brown oil (42.03 g) which was used without further purification.

The crude acid (41.0 g) was refluxed in methanol (600 ml) containing concentrated sulphuric acid (2.5 ml), for 3.5 hours. After evaporation of the methanol, the residue was dissolved in ethyl acetate, washed with dilute aqueous sodium hydroxide and then water, dried and evaporated to yield a brown oil (26.31 g). 1.31 g was purified by HPLC (eluant 1:1, ethyl acetate:hexane) to give pure methyl 2-(3-hydroxymethylphenoxy)phenylacetate as a pale yellow oil.

$^1$H n.m.r. (400 MHz) delta: 2.12(1H, s), 3.60 (3H, s), 3.69 (3H, s), 4.62 (2H, s), 6.95 (1H, s), 6.85–6.90 (2H, t), 7.04–7.14 (2H, m), 7.21–7.32 (3H, m) ppm. IR maxima (film): 3450, 1742 cm$^{-1}$.

A mixture of the crude methyl 2-(3-hydroxymethylphenoxy)phenylacetate (25.0 g) and methyl formate (56 ml) in dry DMF (50 ml) was added dropwise to sodium hydride (7.35 g of a 60% dispersion in oil, washed with hexane) in dry DMF (100 ml) over 30 minutes at 5° C. After stirring at 5° C. for another 30 minutes, the mixture was allowed to warm to room temperature over several hours and then stood overnight. The reaction mixture was then poured into water and extracted with ether. The aqueous layer was then acidified with dilute hydrochloric acid and extracted with ether. The ether extracts were dried and evaporated to give crude methyl 3-hydroxy-2-(2-[3-hydroxymethylphenoxy]phenyl-propenoate as an orange oil (32.19 g). The crude methyl ester (32.10 g) was stirred in DMF (80 ml) at 5°–10° C. with potassium carbonate (25.4 g) and a solution of dimethyl sulphate (11.6 g) in DMF (20 ml) was added dropwise over 10 minutes. The mixture was allowed to warm to room temperature over a few hours and then stood overnight. The reaction mixture was poured into water, acidified with dilute hydrochloric acid and extracted with ether. The ether extracts were washed with water, dried and evaporated to give an orange brown oil (14.38 g). Purification by HPLC yielded (E)-methyl 3-methoxy-2-(2-[3-hydroxymethylphenoxy]phenyl)propenoate as a slightly pinkish crystalline solid (7.8 g).

$^1$H n.m.r. (270 MHz) delta: 2.55 (1H, s), 3.58 (3H, s), 3.74 (3H, s), 4.55 (2H, s), 6.8–7.28 (8H, m), 7.44 (1H, s) ppm. IR maxima (nujol): 3515, 1705, 1625 cm$^{-1}$.

Part of this alcohol (0.314 g) was stirred in dry methylene chloride (5 ml) and pyridinium dichromate (0.564 g) was added, and the mixture was stirred for 4 hours at room temperature. The mixture was then filtered and the precipitate washed with ether. The combined methylene chloride and ether washings were evaporated to give (E)-methyl 3-methoxy-2-(2-[3-formylphenoxy]phenyl)propenoate as a brown oil (0.309 g).

$^1$H n.m.r. (270 MHz) delta: 3.59 (3h, s), 3.65 (3H, s), 6.98 (1H, d), 7.17–7.36 (4H, m), 7.40–7.47 (3H, m), 7.47 (1H, s), 7.55 (1H, d) ppm. IR maxima (film): 1710, 1640 cm$^{-1}$.

(E)-Methyl 3-methoxy-2-(2-[3-formylphenoxy]phenyl) propenoate (0.50 g) was stirred in dry THF (20 ml) at −20° C. under nitrogen. Phenylmagnesium bromide (0.53 ml of a 3M solution in ether) as a dilute solution in dry THF (5 ml) was added slowly dropwise. After completion of the addition the reaction was stirred at −20° C. for 30 minutes and then slowly warmed to room temperature over 1 hour, and then stood overnight. The mixture was then cooled to 5° C., water was added, and the resulting mixture was extracted with ethyl acetate. After washing with brine and drying, the ethyl acetate solution was evaporated to give a yellow oil. This was purified by HPLC (eluant 2:1, hexane:ether) to give the title compound as a colourless oil (0.340 g).

$^1$H n.m.r. (400MHz) delta: 2.30 (1H, d), 3.57 (3H, s), 3.72(3H, s), 5.78 (1H, d), 6.82 (1H, d), 6.91 (1H, d), 7.02–7.08 (2H, m), 7.10–7.16 (1H, m), 7.20–7.38 (8H, m), 7.45 (1H, s) ppm. IR maxima (film): 3460, 1715, 1635 cm$^{-1}$.

EXAMPLE 18

This Example illustrates the preparation of (E)-methyl 3-methoxy-2-(2-[3-(2-pyridyloxymethyl)phenoxy]phenyl) propenoate, (Compound No. 6 of Table II).

Silver carbonate (0.28 g) was added to (E)-methyl 3-methoxy-2-(2-[3-bromomethylphenoxy]phenyl)propenoate (0.75 g, 70% pure, prepared by the method described in Example 8) and 2-pyridone (0.19 g) in hexane. The mixture was refluxed and excluded from light by wrapping with foil, for 3 hours, and then stood overnight. The hexane was evaporated and the residue was taken up in methylene chloride and filtered through celite. The filtrate was washed with aqueous sodium bicarbonate and then water, dried and evaporated to yield an orange gum (0.72 g). This was purified by HPLC (eluant 1:1, ether:hexane) to give the title compound as a colourless gum (0.188 g).

$^1$H n.m.r. (270 MHz) delta: 3.60 (3H, s), 3.76 (3H, s), 5.32 (2H, s), 6.78 (1H, d), 6.84–6.96 (3H, m), 7.04–7.16 (3H, m), 7.21–7.31 (3H, m), 7.48 (1H,s), 7.52–7.60 (1H, m), 8.15 (1H, d) ppm. IR maxima (film): 1715, 1670, 1645, 1600 cm$^{-1}$.

EXAMPLE 19

This Example illustrates the preparation of (E)-methyl 3-methoxy-2-(2-[3-pyrimidin-2-yloxymethylphenoxy]phenyl)propenoate (Compound No 85 from Table II).

(E)-Methyl 3-methoxy-2-(2-[3-hydroxymethylphenoxy] phenyl)propenoate (0.5 g, prepared as described in Example 17) in dry DMF (a few ml) was added to sodium hydride (0.072 g of 60% dispersion in oil, washed with hexane) stirred in dry DMF (10 ml), at room temperature. After completion of the addition, the mixture was stirred for 5 minutes, and then 2-chloropyrimidine (0.92 g) was added, and then stood overnight. It was then poured into water, acidified and extracted with ether. The ether extracts were dried and evaporated to give a yellow oil (0.95 g). This was purified by HPLC (eluant 1:1, ethyl acetate: hexane) to give the pure title compound (0.104 g), as an oil.

$^1$H n.m.r. (270 MHz) delta: 3.60 (3H, s), 3.75 (3H, s), 5.39 (2H, s), 6.86–6.96 (3H, m), 7.03–7.31 (6H, m), 7.49 (1H, s), 8.50 (2H, d) ppm. IR maxima (film): 1713, 1640 cm$^{-1}$.

EXAMPLE 20

This Example illustrates the preparation of (E,E)- and (E,Z)-methyl 3-methoxy-2-(2-[3-(4-nitrostyryl)phenoxy] phenyl)propenoate (Compound mixture No. 403 of Table I).

Dimethyl phosphite (1.39 g) in dry DMF (5 ml) was added dropwise to a stirred suspension of sodium hydride (0.61 g of a 50% dispersion in oil, washed with hexane) in dry DMF (10 ml), at 20° C. After completion of the addition, and stirring for a further 20 minutes, (E)-methyl 3-methoxy-2-(2-[3-bromomethylphenoxy]phenyl)propenoate (7.0 g of 70% pure material, prepared as described in Example 8) was added dropwise. The reaction mixture stood for 60 hours, and was then heated to 55° C. for 10 hours, and then poured into water and extracted with ethyl acetate. The extract was dried and evaporated to give a viscous yellow gum, which was purified by flash chromatography (eluant 5% methanol in ethyl acetate) to give the phosphonate (E)-methyl 3-methoxy-2-[3-(dimethylphosphonomethyl)phenoxy]phenylpropenoate as a nearly colour less oil (1.50 g).

$^1$H n.m.r. (400 MHz) delta: 3.13 (2H, d), 3.62 (3H, s), 3.66 (3H, s), 3.68 (3H, s) 3.78 (3H, s), 6.85 (1H, d), 6.92 (2H, d), 7.00 (1H, d), 7.13 (1H, t), 7.20–7.31 (4H, m), 7.48 (1H, s) ppm. IR maxima (film): 1715, 1645 cm$^{-1}$.

This phosphonate (0.61 g) in dry DME (5 ml) was added dropwise to sodium hydride (0.072 g of a 50% dispersion in oil, washed with hexane) stirred in dry DME (10 ml) at 5° C. under nitrogen. After completion of the addition, the reaction mixture was warmed to room temperature and stirred for 15 minutes. 4-Nitrobenzaldehyde (0.227 g) in dry DME (5 ml) was slowly added dropwise to the reaction mixture which was then stirred overnight at room temperature. Water was then added and the mixture was extracted with ether. The ether layer was dried and evaporated to give a viscous yellow oil, which was purified by HPLC (eluent 3:1, hexane: ethyl acetate) to give the title compound as a 5:1 mixture of (Z):(E)-stilbene isomers (yellow gum, 0.20 g).

$^1$H n.m.r. (270 MHz) delta: [data for (Z)-isomer]3.57 (3H, s), 3.74 (3H, s), 6.58 (1H, d), 6.72 (1H, d), 6.72–6.98 (3H, m), 7.05–7.36 (7H, m), 7.45(1H, s) 8.06 (2H, d) ppm.

This mixture could be isomerised to an 85:15 (E): (Z)-stilbene isomer mixture by heating uner reflux with a trace of iodine in toluene.

$^1$H n.m.r. (400 MHz) delta (data for (E)-isomer): 3.62 (3H, s), 3.78 (3H, s), 6.92–7.35 (10H, m), 7.49 (1H, s), 7.61 (2H, d), 8.22 (2H, d) ppm.

EXAMPLE 21

This Example illustrates the preparation of (E)-methyl 3-methoxy-2-(2-[3-benzoyloxymethylphenoxy]phenyl)propenoate (Compound No. 398 of Table I).

(E)-Methyl 3-methoxy-2-(2-[3-bromomethylphenoxy] phenyl)propenoate (0.5 g of 75% pure material, prepared as described in Example 8), benzoic acid (0.13 g) and potassium carbonate (0.076 g) were stirred in dry DMF at room temperature overnight. Water was then added and the mixture was extracted with dilute aqueous bicarbonate, dried and evaporated to give a yellow viscous oil (0.49 g), which was purified by HPLC (eluent 5:2, hexane:ethyl acetate) to give the title compound (0.120 g).

$^1$H n.m.r. (400 MHz) delta: 3.60 (3H, s), 3.75 (3H, s), 5.31 (2H, s), 6.93 (1H, d), 6.96 (1H, d), 7.06 (1H, s), 7.12(1H, d), 7.16 (1H, d), 7.44 (2H, t), 7.25–7.32 (2H, m), 7.47 (1H, s), 7.55 (1H, d), 8.05 (2H, d) ppm.

EXAMPLE 22

This Example illustrates the preparation of (E)-methyl 3-methoxy-2-(2-[3-(triphenylphosphoniomethyl)phenoxy] phenyl)propenoate bromide salt (Compound No. 404 of Table I).

(E)-Methyl 3-methoxy-2-(2-[3-bromomethylphenoxy] phenyl)propenoate (4.58 g of 70% pure material, prepared as described in Example 8) and triphenylphosphine (2.33 g) were stirred in dry THF (40 ml) at room temperature, for 4 hours, and then stood overnight. The solvent was evaporated to give a sticky residue which was triturated with ether/ethyl acetate to give the title compound as a yellow-white solid (4.38 g), m.p. 176–177° C.

$^1$H n.m.r. (270 MHz) delta: 3.56 (3H, s), 3.74 (3H, s), 5.28 (2H, d), 6.48 (1H, s), 6.62 (1H, d), 6.77 (1H, d), 6.97 (1H, d), 7.04 (1H, t), 7.10–7.28 (3H, m), 7.40 (1H, s) 7.54–7.80 (15H, m) ppm.

EXAMPLE 23

This example illustrates the preparation of (E,E)-methyl 3-methoxy-2-(2-[3-styrylphenoxy]phenyl)propenoate (Compound No. 18 of Table I).

(E)-Methyl 3-methoxy-2-(2-[3-(triphenylphosphoniomethyl)phenoxy]phenyl)propenoate bromide salt (1.0 g, prepared as described in Example 22) in dry DMF (5 ml) was added dropwise to sodium hydride [0.075 g of a 50% dispersion in oil, washed with hexane] in dry DMF (5 ml) to give an orange solution. After completion of hydrogen evolution (2 hours), benzaldehyde (0.66 g) in dry DMF (5 ml) was added and the reaction mixture was stirred at room temperature for 20 hours and then heated to 60° C. for 2 hours. Water was then added and the mixture was extracted with ethyl acetate. The organic extract was dried and evaporated to give a yellow oil (1.3 g) which was purified by HPLC (eluent THF: hexane, 1:4) to give a 1:1 mixture of the title compound and the corresponding (Z)-styryl isomer (0.362 g).

This (Z):(E) mixture was isomerised to the (E)-isomer only by refluxing in toluene with a crystal of iodine for a few hours to give the (E)-isomer as a colourless gum.

$^1$H n.m.r. (270 MHz) delta: 3.64 (3H, s), 3.77 (3H, s), 6.88(1H, d), 6.96–7.40 (10H, m), 7.49(1H, s), 7.48 (2H, m) ppm. IR maxima (film): 1710, 1640 cm$^{-1}$.

EXAMPLE 24

This Example illustrates the preparation of (E)-methyl 3-methoxy-2-(2-[3-phenoxycarbonylphenoxy]phenyl)propenoate (Compound No. 50 of Table I).

To (E)-methyl 3-methoxy-2-(2-[3-hydroxymethylphenoxy]phenyl)propenoate (2.43 g, prepared as described in Example 17) stirred in acetone (100 ml) at 5°–10° C., was added chromic acid [made by dissolving chromium trioxide (6.5 g) in 18.5 ml water containing 5.5 ml of concentrated sulphuric acid] until a reddish brown colour persisted, and GC indicated the disappearance of all the starting alcohol. The mixture was then poured into water and extracted with ether. The ether extracts were washed with water, dried and evaporated to give (E)-methyl 3-methoxy -2-(2-[3-carboxyphenoxy]phenyl)propenoate as a pale yellow oil (2.495 g).

$^1$H n.m.r. (270 MHz) delta: 3.60 (3H, s), 3.76 (3H, s), 6.95 (1H, d), 7.14–7.40 (5H, m), 7.50 (1H, s), 7.66 (1H, s), 7.78 (1H, d), 9.35 (1H, br s) ppm. IR maxima (film): 3500–2500, 1725, 1640 cm$^{-1}$.

The carboxylic acid from the previous stage (0.33 g) stirred in dry THF (10 ml) was treated with oxalyl chloride (0.11 ml) and one drop of dry DMF. The reaction mixture was stirred for 45 minutes, stood overnight and then evaporated to give crude (E)-methyl 3-methoxy-2-(2 -[3-chlorocarbonylphenoxy]phenyl)propenoate as an orange-yellow oil.

IR maxima (film): 1760, 1715, 1640 cm$^{-1}$.

To the acid chloride from the previous stage in dry THF (15 ml) was added a mixture of phenol (0.090 g) and triethylamine (0.096 g) in dry THF (5 ml). The reaction mixture was stirred at room temperature for 1.5 hours and then poured into water and extracted with ether. The ether extracts were washed with dilute sodium hydroxide and then water, and were then dried and evaporated to give the title compound (136 mg) as an orange oil.

$^1$H n.m.r. (270 MHz) delta: 3.60 (3H, s), 3.77 (3H, s), 6.94(1H, d), 7.14 (2H, t), 7.23–7.38 (3H, m), 7.47 (1H, s), 7.61 (1H, t), 7.72 (1H, d) ppm. IR maxima (film): 1755, 1710, 1640 cm$^{-1}$.

EXAMPLE 25

This Example illustrates the preparation of (E)-methyl 2-[2-(3-[6-chloropyrimidin-4-yloxy]phenoxy)phenyl] -3-methoxypropenoate (Compound No. 89 of Table II).

Potassium carbonate (0.46 g), cuprous chloride (0.027 g) and 4,6-dichloropyrimidine (0.41 g) were added successively to a stirred solution of (E)-methyl 2-[2-(3 -hydroxyphenoxy)phenyl]-3-methoxypropenoate (1.0 g, prepared as described in Example 1) in DMF (10 ml) and the resulting mixture was stirred for 10 hours at room temperature. The mixture was diluted with water and extracted with ether. The extracts were washed successively with aqueous sodium bicarbonate and water, dried, concentrated and chromatographed using ether:hexane (1:1) as eluant to give the title compound (0.39 g, 28% yield) as a colourless oil.

$^1$H n.m.r. (270 MHz) delta: 3.60 (3H, s), 3.76 (3H, s), 6.74 (1H, t), 6.81 (1H, dd), 6.90 (2H, m), 7.03 (1H, m), 7.17 (1H, t), 7.26–7.36 (3H, m), 7.49 (1H, s), 8.59 (1H, s) ppm.

EXAMPLE 26

This Example illustrates the preparation of (E)-methyl 3-methoxy-2-[2-(3-pyrimidin-4-yloxyphenoxy)phenyl]propenoate (Compound No. 92 o f Table II).

A solution of sodium hypophosphite (0.27 g) in water (5 ml) was added dropwise with stirring to a mixture of (E)-methyl 2-[2-(3-[6-chloropyrimidin-4-yloxy]phenoxy)phenyl] -3-methoxypropenoate (0.4 g, prepared as described in Example 25), potassium carbonate (0.2 g) and 5% palladium on carbon (0.08 g) in THF (4 ml). The resulting mixture was stirred at room temperature for 2 hours, then filtered through 'Hyflo', rinsing with ethyl acetate and water. The combined filtrate and washings were separated into aqueous and organic layers. The latter was dried, concentrated and chromatographed using a 1:1 mixture of ether and hexane as eluant to give the title compound (0.19 g, 52% yield) as a colourless oil.

$^1$H n.m.r. (270 MHz) delta: 3.61 (3H, s), 3.75 (3H, s), 6.75 (1H, t), 7.48 (1H, s), 8.56 (1H, d), 8.76 (1H, s) ppm.

EXAMPLE 27

This Example illustrates the preparation of (E)-methyl 3-methoxy-2-[2-(3-[3-nitrophenoxy]phenoxy)phenyl]propenoate (Compound No. 132 of Table I).

A mixture of 3-(3-nitrophenoxy)phenol (1.7 g), (E)-methyl 2-(2-bromophenyl)-3-methoxypropenoate (2.0 g, prepared as described in Example 13), potassium carbonate (1.0 g) and cuprous chloride (1.0 g) was stirred at 170°–180° C. for 5 hours then allowed to cool. The mixture was diluted with water and extracted with ether. The extracts were washed successively with aqueous sodium hydroxide and brine, then dried and concentrated to give a brown oil (3.12 g). Chromatography using varying proportions of ether (up to 20%) in hexane as eluant gave the title compound (1.06 g, 34% yield) as a yellow oil.

$^1$H n.m.r. (270 MHz) delta: 3.60 (3H, s), 3.76 (3H, s), 6.66–6.83 (3H, m), 7.02 (1H, d), 7.18 (1H, d), 7.22–7.38 (3H, m), 7.45–7.52 (1H, m), 7.49 (1H, s), 7.78 (1H, m), 7.92–7.97 (1H, m) ppm.

EXAMPLE 28

This Example illustrates the preparation of (E)-methyl 3-methoxy-2-(2-[3-(3-methoxyphenoxymethyl)phenoxy] phenyl)propenoate (Compound No. 372 of Table I).

(E) -Methyl 3-methoxy-2-(2-[3-methylphenoxy]phenyl-)propenoate (0.50 g, prepared as described in Example 8), 1,3-dibromo-5,5-dimethylhydantoin (0.32 g ) and azoisobutyronitrile (0.033 g) were heated under reflux in carbon tetrachloride (40 ml), while being irradiated with a 400 watt tungsten lamp. After 1 hour the mixture was cooled and poured into water. The organic layer was separated, washed with water, dried and evaporated to give a yellow viscous oil (0.825 g), containing about 65% of (E)-methyl 3-methoxy-2-(2-[3-bromomethylphenoxy]phenyl)propenoate, which was used without further purification (see Example 8 for $^1$H n.m.r. data).

A solution of the crude bromide (0.41 g) in dry DMF (4 ml) was added to a solution of sodium 3-methoxyphenoxide (generated from 3-methoxyphenol and sodium hydride) in dry DMF (6 ml), and the mixture was stirred for 4 hours and then allowed to stand overnight. The reaction mixture was poured into dilute aqueous hydrochloric acid and extracted with ethyl acetate. The organic fractions were dried and evaporated to give a brown oil. This was purified by HPLC (eluant 7:3, 40/60 petroleum ether:ethyl acetate) to give the title compound (0.20 g) as a colourless gum.

IR maxima (film): 1715, 1640 cm$^{-1}$. $^1$H n.m.r. (400 MHz) delta: 3.60 (3H, s), 3.73 (3H, s), 3.77 (3H, s), 4.99 (2H, s), 6.50–6.55 (3H, m), 6.88–6.95 (2H, m), 7.05 (1H, s), 7.09–7.20 (3H, m), 7.24–7.31 (3H, m), 7.47 (1H, s) ppm.

EXAMPLE 29

This Example illustrates the preparation of (E)-methyl 3-methoxy-2-(2-[3-benzoylphenoxy]phenyl)propenoate, (Compound No. 12 of Table I).

Methyl 2-(3-hydroxymethylphenoxy)phenylacetate (10.0 g, preparared as described in Example 17) and celite (10 g) were mixed in methylene chloride (100 ml), and pyridinium chlorochromate (15.85 g) was added in one portion. After stirring at room temperature for 2.5 hours, the mixture was filtered and the filtrate was evaporated to give methyl 2-(3-formylphenoxy)phenylacetate as an orange oil (8.48 g), which was pure enough to use without further purification.

IR maxima (film): 1740, 1700 cm$^{-1}$. $^1$H n.m.r. (270 MHz) delta: 3.59 (3H, s), 3.69 (2H, s), 6.92 (1H, d), 7.14–7.20 (1H, t), 7.23–7.37 (3H, m), 7.43 (1H, m), 7.50 (1H, t), 7.60 (1H, dd), 9.95 (1H, s) ppm.

Phenylmagnesium bromide (2.84 ml of a 3M solution in ether) was added dropwise to a cooled and stirred solution of the aldehyde from the preceding stage (2.30 g) in THF so that the temperature did not rise above −30° C. After completion of the addition (35 minutes), the reaction mixture was slowly warmed to room temperature, stirred ovenight and then cooled in an ice bath while water was carefully added. Dilute hydrochloric acid was then added, and the mixture was extracted with ethyl acetate. The extracts were dried and evaporated to give a yellow oil which was purified by flash chromatography (eluant 2:1, hexane:ethyl acetate) to give methyl 2-[(3-(alpha-hydroxy)benzyl)phenoxy]phenylacetate as a pale yellow oil (1.69 g).

$^1$H n.m.r. (270 MHz) delta: 3.57 (3H, s), 3.68 (2H, s), 5.79 (1H, s), 6.79–6.90 (2H, m), 7.05–7.13 (3H, m), 7.18–7.40 (9H, m) ppm.

The hydroxy-ester from the preceding preparation (0.91 g) was stirred in methylene chloride (25 ml) at room temperature, with two spatula portions of celite. Pyridinium chlorochromate (0.65 g) was then added, and the reaction mixture was stirred for 3 hours. The mixture was filtered and the filtrate was evaporated and purified by HPLC (eluant 3:1, hexane:ethyl acetate) to give methyl 2 -(3-benzoylphenoxy)phenylacetate as a pale yellow gum (0.56 g).

$^1$H n.m.r. (270 MHz) delta: 3.60 (3H, s), 3.70 (2H, s), 6.93 (1H, d), 7.10–7.63 (10H, m), 7.81 (2H, d) ppm. IR maxima (film): 1740, 1660 cm$^{-1}$.

This material was converted into the title compound using sodium hydride and methyl formate and then potassium carbonate and dimethyl sulphate in the two steps described for a similar transformation in Example 7.

IR maxima (film): 1710, 1660, 1635 cm$^{-1}$.

$^1$H n.m.r. (270 MHz) delta: 3.60 (3H, s), 3.75 (3H, s), 6.98 (1H, d), 7.12–7.20 (2H, m), 7.26–7.52 (8H, m), 7.47 (1H, s), 7.55–7.63 (1H, m), 7.80 (2H, dd) ppm.

EXAMPLE 30

This Example illustrates the preparation of (E)-methyl 3-methoxy-2-(2-[3-benzylphenoxy]phenyl)propenoate, (Compound No. 9 of Table I).

Trifluoroacetic acid (3.28 g) was added dropwise with stirring to methyl 2-[(3-(alpha-hydroxy)benzyl)phenoxy] phenylacetate (1.68 g, prepared as described in Example 29) at 5° C. After completion of the addition, triethylsilane (2.24 g) was slowly added dropwise. The resultant clear solution was then stirred overnight, diluted with water and extracted with ether. The ether fraction was washed with aqueous sodium bicarbonate, dried, concentrated and purified by HPLC (eluant 4:1, hexane:ether) to give methyl 2-(3-benzylphenoxy)phenylacetate (1.03 g) as a colourless oil.

IR maximum (film): 1742 cm$^{-1}$.

This material was converted into the title compound using sodium hydride and methyl formate and then potassium carbonate and dimethyl sulphate in the two steps described for a similar transformation in Example 7.

IR maxima (film): 1708, 1635 cm$^{-1}$. $^1$H n.m.r. (270 MHz) delta: 3.56 (3H, s), 3.72 (3H, s), 3.93 (2H, s), 6.76–6.93 (4H, m), 7.08–7.31 (10H, m), 7.47 (1H, s) ppm.

EXAMPLE 31

This Example illustrates the preparation of (E)-methyl 3-methoxy-2-[2-(3-[N-phenylsulphonamido]phenoxy)phenyl]propenoate (Compound No. 78 of Table I).

A mixture of 2-bromophenylacetic acid (21.5 g), 3 -nitrophenol (29.2 g), potassium carbonate (27.6 g) and cuprous chloride (0.5 g) was heated with stirring at 130° C. for 6 hours. After cooling, the mixture was poured into water (500 ml), acidified with concentrated hydrochloric acid and extracted with ethyl acetate (3×200 ml). The extracts were dried, filtered and concentrated to give a dark oil. The oil was dissolved in methanol (400 ml) containing concentrated sulphuric acid (4 ml) and the resulting solution was heated at reflux for 3 hours. The reaction mixture was concentrated and the residue was dissolved in ethyl acetate (300 ml). This solution was washed successively with sodium hydroxide (2×100 ml of 1M aqueous solution) and brine, then dried, filtered and concentrated to give a dark oil. Bulb-to-bulb distillation of this oil (220° C. oven temperature, 0.2 mmHg) gave methyl 2-(3-nitrophenoxy)phenylacetate (16.74 g, 58% yield from 2-bromophenylacetic acid) as a clear pale oil.

1H n.m.r. (270 MHz) delta: 3.60 (3H, s), 3.70 (2H, s), 6.9–8.0 (8H, m) ppm. IR maximum (film): 1739 cm$^{-1}$.

A mixture of methyl 2-(3-nitrophenoxy)phenylacetate (15 g), methanol (100 ml), glacial acetic acid (100 ml), and iron powder (15.0 g) was gently heated with stirring to reflux. After 30 minutes the mixture was cooled and the excess iron powder was filtered off. This filtrate was poured into water (700 ml) and extracted with ether (2×200 ml). The ether extracts were neutralized by stirring with aqueous sodium bicarbonate then dried, filtered and concentrated to give methyl 2-(3-aminophenoxy)phenylacetate (13.0 g, 97% yield) as a pale yellow oil.

$^1$H n.m.r. (270 MHz) delta: 3.63 (3H, s), 3.68 (2H, s), 3.9 (1H, br s), 6.2–7.3 (8H, m) ppm. IR maxima (film): 3400, 3373, 1733 cm$^{-1}$.

A mixture of methyl 2-(3-aminophenoxy)phenylacetate (11.54 g) and methyl formate (27.7 ml) in DMF (25 ml) was added dropwise to a stirred suspension of sodium hydride (3.25 g) in DMF (50 ml) cooled in ice to below 10° C. (effervescence). Following the addition, the reaction mixture was stirred at room temperature for 3 hours, poured into water, acidified with concentrated hydrochloric acid and extracted with ethyl acetate. These extracts were washed with brine, dried and concentrated to give a viscous yellow oil. Potassium carbonate (12.4 g) and dimethyl sulphate (4.25 ml) were added successively to a stirred solution of this yellow oil in DMF (50 mls) and the resulting mixture was stirred at room temperature for 3 hours, poured into water and extracted with ethyl acetate. The extracts were washed with water, dried and concentrated to give (E)-methyl 2-[2-(3-formamidophenoxy)phenyl] -3-methoxypropenoate (13.67, 93% yield) as a clear green gum.

1H n.m.r. (270 MHz) delta: 3.60 (3H, s), 3.78 (3H, s), 7.47 (1H, s) ppm. IR maxima (film): 3309, 1702, 1606 cm$^{-1}$.

Phosphoryl chloride (7.8 ml) was added dropwise to a stirred solution of (E)-methyl 2-[2-(3-formamidophenoxy)phenyl] -3-methoxypropenoate (13.67 g) in methanol (100 ml), the temperature during the addition being kept below 50° C. with the aid of a cooling bath. After stirring for 20 minutes, the reaction mixture was poured into water (500 ml), neutralized with sodium bicarbonate and extracted with ether. The extracts were dried and concentrated to give a yellow oil which was chromatographed using ether as the eluant to give (E)-methyl 2-[2-(3-aminophenoxy)phenyl] -3-methoxypropenoate (8.57 g, 68% yield) as a yellow solid, m.p. 83°–85° C.

$^1$H n.m.r. (270 MHz) delta: 3.6 (2H, br s), 3.62 (3H, s), 3.77 (3H, s), 6.2–6.4 (3H, m), 6.9–7.3 (5H, m), 7.48 (1H, s) ppm. IR maxima (film): 3450, 3370, 1703, 1632 cm$^{-1}$.

A solution of (E)-methyl 2-[2-(3-aminophenoxy)phenyl] -3-methoxypropenoate (0.4 g) in glacial acetic acid (2 ml) was treated with 5.8M hydrochloric acid (1 ml), at −10° C. The stirred solution was then treated with sodium nitrite (0.1 g in 2 ml of water) still at −10° C. After 30 minutes, the resulting solution (containing the diazonium salt) was added to a stirred mixture of glacial acetic acid (0.5 ml) saturated with sulphur dioxide, containing 0.1 g of cuprous chloride (effervescence). After 30 minutes, the reaction mixture was poured into water and extracted with ether. The ether extracts were neutralized with a saturated aqueous solution of sodium bicarbonate, dried and concentrated to give (E)-methyl 2-[2-(3-chlorosulphonylphenoxy)phenyl] -3-methoxypropenoate (0.14 g) as a yellow oil.

IR maxima (film): 1710, 1636 cm$^{-1}$.

A solution of methyl 2-[2-(3-chlorosulphonylphenoxy)phenyl] -3-methoxypropenoate (0.14 g) in pyridine (0.5 ml) was treated dropwise with aniline (0.05 ml) at room temperature with stirring. After 3 hours the reaction mixture was poured into water. 2M Hydrochloric acid was added to the resulting mixture until it was slightly acidic and it was extracted with ether. The ether extracts were washed with brine, dried, concentrated and chromatographed using ether as the eluant to give the title compound (0.145 g) as a clear oil.

IR maxima (film): 3240, 1693, 1635, 1600 cm$^{-1}$. $^1$H n.m.r. (270 MHz) delta: 3.55 (3H, s), 3.69 (3H, s), 6.53 (1H, br s), 6.8 (1H, m), 7.0–7.4 (12H, m), 7.43 (1H, s) ppm.

EXAMPLE 32

This Example illustrates the preparation of (E)-methyl 2-[2-(3-[3-bromobenzoylamino]phenoxy)phenyl]-3 -methoxypropenoate (Compound No. 421 of Table I).

3-Bromobenzoyl chloride (0.37 g) was added to a stirred solution of (E)-methyl 2-[2-(3-aminophenoxy)phenyl] -3-methoxypropenoate (0.5 g, prepared as described in Example 31) in dichloromethane (20 ml) containing triethylamine (0.17 g). After 3 hours, the reaction mixture was poured into water and extracted with dichloromethane (2×50 ml). The extracts were dried, concentrated and chromatographed using ether as the eluant to give the title compound (0.61 g) as a pale yellow foam.

IR maxima (nujol): 1710, 1680, 1640, 1605 cm$^{-1}$. $^1$H n.m.r. (270 MHz) delta: 3.62 (3H, s), 3.78 (3H, s), 6.73–8.0 (13H, m), 7.47 (1H, s) ppm.

EXAMPLE 33

This Example illustrates the preparation of (E)-methyl 2-[2-(3-pyridin-2-yloxyphenoxy)phenyl]-3 -methoxypropenoate (Compound No. 1 of Table II).

Potassium carbonate (0.92 g), cuprous chloride (catalytic), copper bronze (catalytic) and 2-fluoropyridine (1.94 g) were added successively to a stirred solution of (E)-methyl 2-[2-(3-hydroxyphenoxy)phenyl]-3 -methoxypropenoate (2.0 g, prepared as described in Example 1) in DMF (15 ml). The resulting mixture was stirred for 3 hours at 130° C. After cooling, the mixture was diluted with water and extracted with ether (×2). The combined extracts were washed successively with aqueous sodium hydroxide, water and brine, then dried and concentrated. Chromatography using ether-hexane mixtures as eluant gave the title compound (1.68 g, 67% yield) as an orange-yellow gummy oil.

$^1$H n.m.r. (270 MHz) delta: 3.60 (3H, s), 3.73 (3H, s), 6.72–7.32 (10H, m), 7.48 (1H, s), 7.67 (1H, m), 8.19 (1H, m) ppm.

EXAMPLE 34

This Example illustrates the preparation of (E)-methyl 2-[2-(3-[6-chloropyridazin-3-yloxy]phenoxy)phenyl]

85

-3-methoxypropenoate (Compound No. 130 of Table II).

Potassium carbonate (0.93 g), cuprous chloride (catalytic) and 3,6-dichloropyridazine (1.0 g) were added successively to a stirred solution of (E)-methyl 2-[2-(3-hydroxyphenoxy)phenyl]-3-methoxypropenoate (2.01 g, prepared as in Example 1) in DMF (30 ml). The resulting mixture was stirred for 1½ hours at 95° C. After cooling, the mixture was diluted with water and extracted with ether (×2). The combined extracts were washed successively with aqueous sodium hydroxide, water and brine, then dried and concentrated. Chromatography using ether-hexane mixtures gave the title compound (1.71 g, 62% yield) as a yellow gum.

$^1$H n.m.r. (270 MHz) delta: 3.60 (3H, s), 3.73 (3H, s), 6.73–7.36 (9H, m), 7.46 (1H, m), 7.50 (1H, s) ppm.

The following are examples of compositions suitable for agricultural and horticultural purposes which can be formulated form the compounds of the invention. Such compositions from another aspect of the invention, Percentages are by weight.

EXAMPLE 35

An emulsifiable concentrate is made up by mixing and stirring the ingredients until all are dissolved.

| | |
|---|---|
| Compound No. 212 of Table I | 10% |
| Benzyl alcohol | 30% |
| Calcium dodecylbenzenesulphonate | 5% |
| Nonylphenolethoxylate (13 moles ethylene oxide) | 10% |
| Alkyl benzenes | 45% |

EXAMPLE 36

The active ingredient is dissolved in methylene dichloride and the resultant liquid sprayed on to the granules of attapulgite clay. The solvent is then allowed to evaporate to produce a granular composition.

| | |
|---|---|
| Compound No. 212 of Table I | 5% |
| Attapulgite granules | 95% |

EXAMPLE 37

A composition suitable for use as a seed dressing is prepared by grinding and mixing the three ingredients.

| | |
|---|---|
| Compound No. 212 of Table I | 50% |
| Mineral oil | 2% |
| China clay | 48% |

EXAMPLE 38

A dustable powder is prepared by grinding and mixing the active ingredient with talc.

| | |
|---|---|
| Compound No. 212 of Table I | 5% |

86

| -continued | |
|---|---|
| Talc | 95% |

EXAMPLE 39

A suspension concentrate is prepared by ball milling the ingredients to form an aqueous suspension of the ground mixture with water.

| | |
|---|---|
| Compound No. 212 of Table I | 40% |
| Sodium lignosulphonate | 10% |
| Bentonite clay | 1% |
| Water | 49% |

This formulation can be used as a spray by diluting into water or applied directly to seed.

EXAMPLE 40

A wettable powder formulation is made by mixing together and grinding the ingredients until all are thoroughly mixed.

| | |
|---|---|
| Compound No. 212 of Table I | 25% |
| Sodium lauryl sulphate | 2% |
| Sodium lignosulphonate | 5% |
| Silica | 25% |
| China clay | 43% |

EXAMPLE 41

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient except where otherwise indicated) were sprayed onto the foliage and applied to the roots of the plants in the soil. The sprays were applied to maximum retention and the root drenches to a final concentration equivalent to approximately 40 ppm a.i./dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4=no disease
3=trace –5% of disease on untreated plants
2=6–25% of disease on untreated plants
1=26–59% of disease on untreated plants
0=60–100% of disease on untreated plants The results are shown in Table VI.

Table VI

| COMPOUND NO | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 1 | I | 4 | 4 | 4 | 4 | 4 | 4 | 3 |
| 2 | I | 4 | 2 | 4 | 4 | 4 | 4 | 0 |
| 3 | I | 3 | 0 | 4 | 2 | 4 | 4 | 0 |
| 4 | I | 4 | 4 | 4 | 3 | 4 | 4 | 3 |
| 5 | I | 4 | 4 | 4 | 3 | 4 | 4 | 2 |
| 6 | II | 4 | 4 | 4 | 4 | 4 | 4 | 4 |
| 7 | I | 3 | 4 | 4 | 3 | 4 | 4 | 0 |
| 12 | I | 4 | 3 | 4 | 4 | 4 | 4 | 4 |
| 18 | I | 4 | 3 | 4 | 4 | — | 4 | 0 |
| 21 | I | 4 | 4 | 0 | 0 | 4 | 4 | 4 |
| 22 | II | 4 | 4 | 4 | 3 | 4 | 4 | 4 |
| 22 | IV | 4 | 0 | 4 | 4 | 4 | 4 | 3 |
| 23 | I | 4 | 3 | 4 | 4 | 4 | 4 | 4 |
| 24 | I | 4 | 4 | 4 | 3 | 4 | 4 | 2 |
| 25 | I | 4 | 3 | 4 | 3 | 4 | 4 | 3 |
| 27 | I | 4 | 0 | 4 | 4 | 3 | 4 | 3 |
| 29 | I | 4 | 3 | 4 | 0 | 4 | 4 | 3 |
| 38 | I | 4 | 3 | 3 | 4 | 4 | 4 | 4 |
| 38 | II | 4 | 4 | 4 | 4 | 2 | 4 | 3 |
| 47 | II | 0 | 4 | 4 | 3 | 4 | 4 | 3 |
| 49 | I | 4 | 2 | 4 | 3 | 4 | 4 | 3 |
| 50 | I | 3 | 0 | 3 | 2 | 0 | 4 | 2 |
| 51 | I | 4 | 4 | 3 | 4 | 4 | 4 | 4 |
| 52 | II | 4 | 4 | 4 | 4 | 4a | — | 0 |
| 53 | II | 4 | 3 | 4 | 4 | 4 | 4 | 4 |
| 62 | I | 4 | 3 | 4 | 4 | 4 | 3 | 4 |
| 67 | I | 3 | 4 | 4 | 3 | 3 | 4 | 3 |
| 81 | II | 4 | 4 | 0 | 3 | 1 | 4 | 3 |
| 83 | II | 3 | 4 | 4 | 4 | 2 | 4 | 3 |
| 84 | I | 3 | 0 | 4 | 0 | 0 | 4 | 0 |
| 84 | II | 4 | 4 | 4 | 3 | 4 | 4 | 1 |
| 85 | II | 4 | 4 | 4 | 4 | 4 | 4 | 4 |
| 86 | I | 1 | 0 | 4 | 1 | 4 | 4 | 0 |
| 86 | II | 0 | 0 | 0 | 0 | 0 | 2 | 0 |
| 87 | II | 3 | 4 | 4 | 4 | 2 | 4 | 3 |
| 87 | IV | 3a | 0a | 4a | 3a | 4a | 4a | 0a |
| 89 | II | 4 | 4 | 4 | 3 | 4 | 4 | 3 |
| 90 | II | 4 | 4 | 4 | 4 | 4 | 4 | 3 |
| 93 | II | 4 | 3 | 4 | 3 | 2 | 4 | 0 |
| 94 | II | 4 | 3 | 4 | 4 | 4 | 4 | 4 |
| 95 | II | 1 | 0 | 4 | 0 | 1 | 4 | 0 |
| 96 | I | 4 | 4 | 4 | 2 | 4 | 4 | 2 |
| 96 | II | 4 | 0 | 3 | 1 | 0 | 4 | 3 |
| 98 | II | 4 | 4 | 4 | 4 | 4 | 4 | 4 |
| 99 | II | 3 | 4 | 4 | 3 | 1 | 4 | 0 |
| 100 | II | 4 | 4 | 4 | 4 | 4 | 4 | 3 |
| 105 | II | 3 | 4 | 4 | 4 | 4 | 4 | 3 |
| 111 | I | 3 | 0 | 4 | 3 | 2 | 4 | 0 |
| 115 | I | 4 | 3 | 4 | 4 | 4 | 4 | 3 |
| 119 | I | 4 | 4 | 4 | 4 | 4 | 4 | 4 |
| 120 | I | 4 | 3 | 4 | 3 | 4 | 4 | 4 |
| 122 | I | 4 | 4 | 4 | 3 | 4 | 4 | 4 |
| 124 | I | 4 | 4 | 4 | 4 | 4 | 4a | 4 |
| 125 | I | 4 | 4 | 4 | 3 | 4 | 4 | 4 |
| 126 | I | 4 | 3 | 4 | 3 | 4 | 4 | 3 |
| 127 | I | 4 | 3 | 4 | 4 | 4 | 4 | 2 |
| 128 | I | 4 | 4 | 4 | 3 | 4 | 4 | 4 |
| 129 | I | 4 | 2 | 4 | 4 | 4 | 4 | 4 |
| 130 | I | 4 | 3 | 4 | — | 4 | 4 | 4 |
| 131 | I | 4a | 4a | 4a | 4a | — | 4a | 4a |
| 131 | III | 0a | 0a | 4c | 4a | 4a | 0c | 0c |
| 132 | I | 4 | 4 | 4 | 4 | 4 | 4 | 3 |
| 133 | I | 4 | 2 | 4 | 4 | 4 | 4 | 2 |
| 134 | I | 4 | 4 | 4 | 4 | 4 | 4 | 4 |
| 135 | I | 4 | 4 | 4 | 4 | 4 | 4 | 3 |
| 138 | I | 4 | 4 | 4 | 3 | 4 | 4 | 4 |
| 141 | I | 4 | 4 | 4 | 3 | 4 | 4 | 0 |
| 143 | I | 4 | 4 | 4 | 3 | 4 | 3 | 3 |

Table VI-continued

| COMPOUND NO | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 144 | I | 4 | 4 | 4 | 3 | 4 | 4 | 0 |
| 145 | I | 4 | 3 | 4 | 3 | 4 | 4 | 1 |
| 150 | I | 3 | 3 | 4 | 4 | 3a | — | 0 |
| 157 | I | 3 | 3 | 4 | 3 | 4 | 0 | 0 |
| 171 | I | 4 | 4 | 4 | 4 | 3a | — | 0 |
| 175 | I | 4 | 4 | 4 | 4 | 3 | 4 | 0 |
| 177 | I | 4 | 4 | 4 | 3 | — | 4 | 0 |
| 179 | I | 1 | 1 | 0 | 0 | 2 | 4 | 0 |
| 204 | I | 4 | 4 | 4 | 4 | 4a | — | 0 |
| 205 | I | 4 | 4 | 4 | 4 | 3a | — | 1 |
| 206 | I | 4 | 4 | 4 | 4 | 4 | 4 | 3 |
| 208 | I | 4 | 4 | 4 | — | 3 | 4 | 3 |
| 212 | I | 4 | 4 | 4 | 4 | 4 | 4 | 0 |
| 214 | I | 4 | 4 | 4 | — | 4 | 4 | 4 |
| 216 | I | 4 | 3 | 4 | — | 4 | 4 | 4 |
| 217 | I | 4 | 4 | 4 | 3 | 3a | — | 0 |
| 218 | I | 4 | 3 | 3 | — | 4 | 4 | 4 |
| 220 | I | 4 | 3 | 4 | 2 | 4 | 4 | 0 |
| 230 | I | 4 | 2 | 4 | 4 | 4 | 4 | 0 |
| 247 | I | 4 | 4 | 4 | 0 | 3 | 4 | 3 |
| 248 | I | 4 | 3 | 4 | — | 4 | 4 | 2 |
| 282 | I | 4 | 2 | 4 | 0 | 4 | 4 | 2 |
| 283 | I | 4 | 3 | 4 | 4 | 3 | 4 | 0 |
| 284 | I | 4 | 4 | 4 | 4 | 3 | 4 | 0 |
| 285 | I | 4 | 4 | 4 | 4 | 3 | 4 | 2 |
| 288 | I | 4 | 3 | 4 | 4 | 4 | 4 | 0 |
| 290 | I | 4 | 1 | 4 | 3 | 4 | 4 | 0 |
| 291 | I | 4 | 0 | 0 | 3 | — | 4 | 1 |
| 294 | I | 3 | 4 | 4 | 4 | 4 | 4 | 1 |
| 295 | I | 4 | 0 | 4 | 1 | 4 | 4 | 0 |
| 296 | I | 4 | 0 | 4 | 4 | — | 4 | 0 |
| 332 | I | 0a | 0a | — | 2a | — | 4a | 2a |
| 333 | I | 4 | 1 | 2 | 3 | — | 4 | 0 |
| 360 | I | 4 | 4 | 4 | 4 | 4 | 4 | 1 |
| 365 | I | 4 | 3 | 4 | 3 | — | 4 | 3 |
| 366 | I | 0a | 4a | 3a | 0a | — | 4a | 0a |
| 367 | I | 3a | 1a | 0a | 1a | 4a | 3a | 3a |
| 368 | I | 1 | 0 | 0 | 0 | — | 0 | 0 |
| 369 | I | 4 | 0 | 3 | 2 | — | 4 | 0 |
| 370 | I | 4 | 2 | 4 | 4 | — | 4 | 4 |
| 371 | I | 4 | 4 | 4 | 3 | 4 | 4 | 3 |
| 372 | I | 4 | 4 | 4 | 3 | 4 | 4 | 2 |
| 373 | I | 3 | 4 | 4 | 3 | 4 | 4 | 3 |
| 374 | I | 3 | 4 | 4 | 4 | 3 | 4 | 3 |
| 375 | I | 4 | 4 | 4 | 3 | 1 | 4 | 2 |
| 376 | I | 4 | 3 | 0 | 4 | 1 | 4 | 3 |
| 377 | I | 4 | 4 | 0 | 4 | 3 | 4 | 3 |
| 378 | I | 3 | 4 | 0 | 4 | 4 | 4 | 4 |
| 380 | I | 3 | 4 | 0 | 4 | 4 | 4 | 3 |
| 381 | I | 3 | 4 | 0 | 4 | 4 | 4 | 4 |
| 382 | I | 4 | 4 | 4 | 3 | 4 | 4 | 2 |
| 383 | I | 4 | 3 | 4 | 4 | 4 | 4 | 0 |
| 384 | I | 4 | 4 | 4 | 4 | 4 | 0 | 0 |
| 385 | I | 4 | 1 | 4 | 4 | 4 | 4 | 0 |
| 386 | I | 4 | 4 | 4 | 3 | 4 | 4 | 2 |
| 387 | I | 4 | 1 | 0 | 4 | 4 | 4 | 3 |
| 388 | I | 3a | 4a | 4a | 4a | 4a | 3a | 0a |
| 389 | I | 4 | 3 | 4 | 3 | 4 | 4 | 4 |
| 390 | I | 4 | 4 | 4 | 2 | 4 | 4 | 2 |
| 391 | I | 4 | 3 | 4 | 4 | 4 | 4 | 2 |
| 392 | I | 4 | 2 | 4 | 4 | 4 | 4 | 0 |
| 393 | I | 4 | 4 | 4 | 4 | 4 | 4 | 0 |
| 394 | I | 4 | 3 | 4 | 4 | 4 | 4 | 0 |
| 395 | I | 3a | 1a | 4b | 4a | 4a | 4b | 3b |
| 396 | I | 4 | 3 | 4 | 3 | 4 | 4 | 3 |
| 397 | I | 4 | 4 | 4 | 4 | 4 | 4 | 0 |
| 398 | I | 3 | 0 | 3 | 2 | 2 | 4 | 2 |
| 399 | I | 4a | 3a | 4a | 4a | 4a | 4a | 2a |
| 400 | I | 2 | 0 | 4 | 4 | 2 | 4 | 0 |
| 401 | I | 4a | 3a | 4a | 4a | 4a | — | 0a |
| 402 | I | 4 | 2 | 2 | 3 | 4 | 4 | 3 |
| 403 | I | 4 | 4 | 4 | 3 | 3 | 3 | 0 |
| 404 | I | 4 | 3 | 3 | 0 | 4 | 3 | 0 |
| 405 | I | 4 | 4 | 4 | 4 | 4a | — | 0 |

Table VI-continued

| COMPOUND NO | TABLE NO. | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PHYTOPHTHORA INFESTANS (TOMATO) |
|---|---|---|---|---|---|---|---|---|
| 406 | I | 3 | 0 | 4 | 0 | 0 | 4 | 0 |
| 407 | I | 4 | 4 | 4 | 0 | — | 4 | 0 |
| 408 | I | 3 | 0 | 4 | 1 | 4 | 4 | 0 |
| 409 | I | 4 | 0 | 3 | 0 | 4 | 4 | 0 |
| 410 | I | 4 | 2 | 4 | 3 | 4 | 4 | 1 |
| 410 | III | 4 | 2 | 3 | 3 | — | 4 | 1 |
| 411 | I | 4 | 3 | 4 | 4 | 4 | 4 | 3 |
| 411 | III | 4 | 2 | 3 | 0 | 0 | 3 | 0 |
| 412 | I | 4 | 3 | 4 | 4 | 4 | 4 | 2 |
| 413 | I | 4 | 2 | 4 | 4 | 4 | 4 | 0 |
| 414 | I | 4 | 1 | 4 | 3 | 4 | 4 | 0 |
| 423 | I | 4 | 4 | 4 | 4 | 4 | 4 | 3 |
| 424 | I | 4 | 3 | 4 | 4 | 4 | 3 | 4 | a = 25 ppm foliar spray
b = 15 ppm foliar spray
c = 10 ppm foliar spray
— = test failed/missing

We claim:

1. A fungicidal compound of the formula (I):

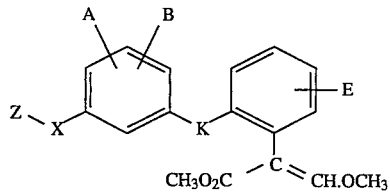

or a stereoisomer thereof, wherein K is oxygen or sulphur; Z is optionally substituted heteroaryl; X is O, $S(O)_n$, $NR^4$, $CR^1R^2$, $CHR^9$, CO, $CR^1(OR^2)$, $C=CR^1R^2$, $CHR^1CHR^2$, $CR^1=CR^2$, $CHR^1CR^2=CH$, $C=C$, $OCHR^1$, $CHR^1O$, $OCHR^1O$, $S(O)_nCHR^1$, $S(O)_nCHR^1O$, $CHR^1S(O)_n$, $CHR^1OSO_2$, $NR^4CHR^1$, $CHR^1NR^4$, $CO_2$, $O_2C$, $SO_2O$, $OSO_2$, CO.CO, $COCHR^1$, $COCHR^1O$, $CHR^1CO$, $CHOH.CHR^1$, $CHR^1.CHOH$.

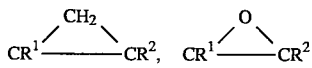

$CONR^4$, $OCONR^4$, $NR^4CO$, $CSNR^4$, $OCS.NR^4$, $SCO.NR^4$, $NR^4CO_2$, $NR^4CSO$, $NR^4COS$, $NR^4CS$, $NR^4CONR^4$, $S(O)_nNR^4$, $NR^4S(O)_n$, $CS_2$, $S_2C$, CO.S, SCO, N=N, $N=CR^1$, $CR^1=H$, $CHR^1CHR^2CH(OH)$, $CHR^1OCO$, $CHR^1SCO$, $CHR^1NR^4CO$, $CHR^1NR^4CONR^4$, $CHR^1CHR^2CO$, $O.N=CR^1$, $CHR^1O.N=CR^2$, $COOCR^1R^2$, $CHR^1CHR^2CHR^3$, $OCHR^1CHR^2$, $(CH_2)_mO$, $CHR^1OCHR^2$, $CHR^1CHR^2O$, $OCHR^1$, $CHR^2O$, $S(O)CHR^1CHR^2$, $CHR^1S(O)_nCHR^2$, $CHR^1CHR^2S(O)_n$, $CR^1=NNR^4$, $NR^4N=CR^1$, $CHR^1CONR^2$, $CHR^1OCO.NR^2$, $CH=CHCH_2O$, $COCHR^1CHR^2O$, or $(R^5)_2P^+CHR^2Q^-$, A, B and E, which may be the same or different, are H, halo, hydroxy, $C_{1-4}$ alkyl, $C_{1-4}$ alkoxy, $C_{1-4}$ haloalkyl, $C_{1-4}$ haloalkoxy, $C_{1-4}$ alkylcarbonyl, $C_{1-4}$ alkoxycarbonyl, phenoxy, nitro or cyano; $R^1$, $R^2$ and $R^3$, which may be the same or different, are H, $C_{1-4}$ alkyl or phenyl; $R^4$ is H, $C_{1-4}$ alkyl or $COR^1$; $R^5$ is optionally substituted phenyl; is substituted phenyl; $Q^-$ is a halide anion; n is 0, 1 or 2 and m is 3, 4 or 5.

2. A compound according to claim 1 wherein X is O.

3. A compound according to claim 1 wherein Z is an optionally substituted 5- or 6-membered heterocyclic ring containing one or more heteroatoms selected from O, S and N and optionally a fused benzene ring, or, when the heterocyclic ring contains a N atom, a N-oxide thereof.

4. A compound according to claim 1 wherein Z is an optionally substituted heteroaryl group selected from pyridinyl, pyrimidinyl, pyrazinyl, pyridazinyl, 1,2,3-, 1,2,4-, and 1,3,5-triazinyl, 1,2,4,5-tetrazinyl, 1,2,3- and 1,2,4-triazol, thienyl, furyl, pyrrolyl, thiazolyl, oxadiazolyl, quinolinyl, isoquinolinyl, quinoxalinyl, benzothienyl, benzoxazolyl and benzthiazolyl and, where appropriate, the corresponding N-oxides.

5. A compound according to claim 1 wherein Z is heteroaryl optionally substituted with one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$ alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, optionally substituted phenyl, optionally substituted pyridinyl or pyrimidinyl, optionally substituted phenoxy, optionally substituted pyridinyloxy or pyrimidinyloxy, optionally substituted phenyl($C_{1-4}$)alkyl in which the alkyl moiety is optionally substituted with hydroxy, optionally substituted pyridinyl- or pyrimidinyl($C_{1-4}$)alkyl, optionally substituted phenyl($C_{2-4}$)alkenyl, optionally substituted pyridinyl- or pyrimidinylethenyl, optionally substituted phenyl($C_{1-4}$)alkoxy, optionally substituted phenoxy($C_{1-4}$)alkyl, optionally substituted pyridinyloxy- or pyrimidinyloxy($C_{1-4}$)alkyl, $C_{1-4}$ alkanoyloxy, benzoyloxy, cyano, thiocyanato, nitro, —NR'R", —NHCOR', —NHCONR'R", —CONR'R", —COOR', —OSO$_2$R', —SO$_2$R', —COR', —CR'=NR" or —N=CR'R" in which R' and R" are independently hydrogen, $C_{1-4}$ alkyl, $C_{1-4}$ alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy, and the aryl or heteroaryl rings of any of the foregoing substituents being optionally substituted with one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo($C_{1-4}$)alkyl, halo($C_{1-4}$)alkoxy, $C_{1-4}$alkylthio, hydroxy($C_{1-4}$)alkyl, $C_{1-4}$ alkoxy($C_{1-4}$)alkyl, $C_{3-6}$ cycloalkyl, $C_{3-6}$ cycloalkyl($C_{1-4}$)alkyl, alkanoyloxy, benzyloxy, cyano, thiocyanato, nitro, —NR'R", —NHCOR', —NHCONR'R", —CONR'R", —COOR', —OSO$_2$R', —SO$_2$R', —COR', —CR'=NR" or N=CR'R" in which R' and R" have the meanings given above.

6. A fungicidal compound of the formula (Ic):

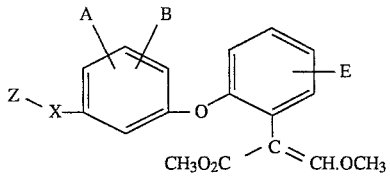

(Ie)

wherein Z is pyridinyl, pyrimidinyl, triazinyl, pyrazinyl, pyridazinyl, quinolinyl, benzoxazolyl, benzthiazolyl, thienyl, quinoxalinyl, thiazolyl, isoquinolinyl, quinazolinyl, purinyl, oxazolyl, thiadiazolyl, oxadiazolyl, furyl, pyrrolyl or thienopyrimidinyl, each optionally substituted with halo, $C_{1-4}$ alkyl, $C_{1-4}$ alkoxy, $C_{1-4}$ alkylthio, halo($C_{1-4}$)alkyl, cyano, nitro, COOR$^7$, phenyl, phenoxy $C_{1-4}$ alkanoyl and CONR$^7$R$^8$ in which R$^7$ and R$^8$ are independently H or $C_{1-4}$ alkyl; or a N-oxide thereof; X is O, S, NH, N(CH$_3$), SO$_2$O, CH$_2$, CH$_2$CH$_2$, OCH$_2$, CH$_2$O, CH(OH), CONH or CO; A and B are independently H, halo, $C_{1-4}$ alkyl, $C_{1-4}$ alkoxy, cyano, nitro, halo($C_{1-4}$)alkyl or halo($C_{1-4}$)alkoxy; and E is H or halo.

7. A compound according to claim 6 wherein X is O, S, OCH$_2$, SO$_2$O, CH$_2$, CH$_2$O, CONH or CON(CH$_3$); Z is pyridin-2-yl, pyrimidin-2-yl, pyrimidin-4-yl, pyrimidin-5-yl, pyrazin-2-yl, pyridazin-3-yl, 1,3,5-triazin-2-yl, thien-2-yl, pyrrol-2-yl, quinolin-2-yl, quinoxalin-2-yl, 1,2,4-triazol-1-yl, thiazol-4-yl, benzthiazol-2-yl, or benzoxazol-2-yl, each optionally substituted with halogen, trifluoromethyl, $C_{1-4}$ alkyl, $C_{1-4}$ alkoxy, cyano or nitro, or a N-oxide thereof and A, B and E are all H.

8. A fungicidal compound of the formula (Ie):

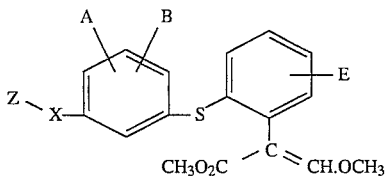

(Ie)

wherein Z is pyridinyl, pyrimidinyl, triazinyl, pyrazinyl, pyridazinyl, quinolinyl, benzoxazolyl, benzthiazolyl, thienyl, quinoxalinyl, thiazolyl, isoquinolinyl, quinazolinyl, purinyl, oxazolyl, thiadiazolyl, oxadiazolyl, furyl, pyrrolyl or thienopyrimidinyl, each optionally substituted with halo, $C_{1-4}$ alkyl, $C_{1-4}$ alkoxy, $C_{1-4}$ alkylthio, halo($C_{1-4}$)alkyl, cyano, nitro, COOR$^7$, phenyl phenoxy $C_{1-4}$ alkanoyl and CONR$^7$R$^8$ in which R$^7$ and R$^8$ are independently H or $C_{1-4}$ alkyl; or a N-oxide thereof; X is O, S, NH, N(CH$_3$), SO$_2$O, CH$_2$, CH$_2$CH$_2$, OCH$_2$, CH$_2$O, CH(OH), CONH or CO; A and B are independently H, halo, $C_{1-4}$ alkyl, $C_{1-4}$ alkoxy, cyano, nitro, halo($C_{1-4}$)alkyl or halo($C_{1-4}$)alkoxy; and E is H or halo.

9. A compound according to claim 8 wherein Z is pyrimidin-2 yl or pyrimidin-5-yl, X is O and A, B and E are all H.

10. The (E)-isomer of a compound according to any one of the preceding claims.

11. A fungicidal composition comprising a fungicidally effective amount of a compound according to claim 1 and a fungicidally acceptable carrier or diluent therefor.

12. A method of combating fungi which comprises applying to plants, to the seeds of plants or to the locus of the plants or seeds, a compound according to claim 10.

13. A compound according to claim 8 wherein Z is pyrimidin-2 yl, X is O and A, B and E are all H.

* * * * *

UNITED STATES PATENT AND TRADEMARK OFFICE
CERTIFICATE OF CORRECTION

PATENT NO.     : 5,468,857

DATED          : November 21, 1995

INVENTOR(S)    : ANTHONY et al.

It is certified that error appears in the above-identified patent and that said Letters Patent is hereby corrected as shown below:

Column 1, line 28, change "C=C" to --C≡C--;

Claim 1, Column 91, line 38, change "C=C" to --C≡C--;

Claim 1, Column 91, line 42, after "CHR$^1$.CHOH" change the period to a comma;

Claim 1, Column 91, line 51, change "CR$^1$=H" to --CR$^1$=N--;

Claim 1, Column 91, line 64, following "phenyl;" insert --R$^9$---; and

Claim 4, Column 92, line 31, change "1,2,4-triazol" to --1,2,4-triazolyl-.

Signed and Sealed this

Twenty-fifth Day of March, 1997

Attest:

BRUCE LEHMAN

Attesting Officer

Commissioner of Patents and Trademarks